US010918618B2

(12) United States Patent
Scholz et al.

(10) Patent No.: US 10,918,618 B2
(45) Date of Patent: Feb. 16, 2021

(54) METHODS OF REDUCING MICROBIAL CONTAMINATION

(75) Inventors: Matthew T. Scholz, Woodbury, MN (US); Terry R. Hobbs, St. Paul, MN (US); Danli Wang, Shoreview, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 11/908,237

(22) PCT Filed: Mar. 10, 2006

(86) PCT No.: PCT/US2006/009009
§ 371 (c)(1),
(2), (4) Date: May 19, 2008

(87) PCT Pub. No.: WO2006/099359
PCT Pub. Date: Sep. 21, 2006

(65) Prior Publication Data
US 2009/0226541 A1 Sep. 10, 2009

Related U.S. Application Data

(60) Provisional application No. 60/660,830, filed on Mar. 10, 2005.

(51) Int. Cl.
| *A61K 33/18* | (2006.01) |
| *A61P 31/04* | (2006.01) |
| *A61K 31/23* | (2006.01) |
| *A61K 9/00* | (2006.01) |
| *A61K 31/00* | (2006.01) |
| *A61K 33/42* | (2006.01) |
| *A61K 45/06* | (2006.01) |
| *A61K 31/155* | (2006.01) |

(52) U.S. Cl.
CPC ............ *A61K 31/23* (2013.01); *A61K 9/0034* (2013.01); *A61K 9/0043* (2013.01); *A61K 31/00* (2013.01); *A61K 31/155* (2013.01); *A61K 33/42* (2013.01); *A61K 45/06* (2013.01); *Y02A 50/30* (2018.01)

(58) Field of Classification Search
CPC ...... A61K 31/23; A61K 31/00; A61K 31/155; A61K 9/0034; A61K 9/0043; A61K 33/42; A61K 45/06; Y02A 50/30
See application file for complete search history.

(56) References Cited

U.S. PATENT DOCUMENTS

| 2,818,390 A | 12/1957 | Beaver et al. |
| 3,048,266 A | 8/1962 | Hackhel et al. |
| 3,489,148 A | 1/1970 | Duncan et al. ............... 128/284 |
| 3,806,615 A | 4/1974 | Frankenfeld et al. |
| 3,817,248 A * | 6/1974 | Buckles .................... A61F 6/14 128/DIG. 12 |
| 3,983,214 A | 9/1976 | Misato et al. |
| 3,985,903 A | 10/1976 | Hasegawa |
| 4,002,775 A | 1/1977 | Kabara |
| 4,010,252 A | 3/1977 | Hewitt |
| 4,067,997 A | 1/1978 | Kabara |
| 4,113,854 A | 9/1978 | Andrews et al. |
| 4,160,820 A | 7/1979 | Wagenknecht |
| 4,189,481 A | 2/1980 | Kabara |
| 4,252,834 A | 2/1981 | Inamine et al. |
| 4,284,653 A | 8/1981 | Shigeoka et al. |
| 4,299,852 A | 11/1981 | Ueno et al. |
| 4,338,342 A | 7/1982 | Tan et al. |
| 4,364,929 A * | 12/1982 | Sasmor et al. ............. 424/78.07 |
| 4,485,029 A | 11/1984 | Kato et al. |
| 4,493,439 A | 1/1985 | Ledewitz |
| 4,512,987 A | 4/1985 | Schindlery et al. |
| 4,557,935 A | 12/1985 | af Ekenstam et al. |
| 4,597,975 A | 7/1986 | Woodward et al. |
| 4,599,233 A | 7/1986 | Misato et al. |
| 4,648,876 A | 3/1987 | Becker et al. |
| 4,722,941 A | 2/1988 | Eckert et al. |
| 4,724,149 A | 2/1988 | Gul et al. |
| 4,728,509 A | 3/1988 | Shimizu |
| 4,840,738 A | 6/1989 | Hardy et al. |
| 4,894,220 A | 1/1990 | Nabi et al. |
| 4,931,282 A | 6/1990 | Asmus et al. |
| 4,962,093 A | 10/1990 | Ohkawa et al. |
| 4,963,555 A | 10/1990 | Jones et al. |
| 4,980,163 A | 12/1990 | Blackburn et al. |
| 4,980,374 A | 12/1990 | Steudle et al. |
| 4,983,394 A | 1/1991 | Hussein et al. |
| 4,983,595 A | 1/1991 | Benjamin et al. |
| 4,985,242 A | 1/1991 | Sekine et al. |
| 4,997,851 A | 3/1991 | Isaacs et al. |
| 5,017,617 A | 5/1991 | Kihara et al. |
| 5,084,096 A | 1/1992 | Stovicek |
| 5,093,140 A | 3/1992 | Watanabe |
| 5,098,694 A | 3/1992 | Komp et al. |
| 5,135,910 A | 8/1992 | Blackburn et al. |
| 5,145,685 A | 9/1992 | Carmody |
| 5,188,822 A | 2/1993 | Viccaro et al. |
| 5,192,802 A | 3/1993 | Rencher |
| 5,208,257 A | 5/1993 | Kabara |
| 5,217,950 A | 6/1993 | Blackburn et al. |
| 5,219,887 A | 6/1993 | Andrews et al. |

(Continued)

FOREIGN PATENT DOCUMENTS

| AU | 16317/95 | 11/1995 |
| AU | 2000 49587 | 12/2000 |

(Continued)

OTHER PUBLICATIONS

"Urinary tract infection in hospitalized patients" Morgan, Dorothy M., Canadian Hospital, 1973, p. 27-30.*

(Continued)

*Primary Examiner* — Hong Yu
(74) *Attorney, Agent, or Firm* — 3M IPC

(57) ABSTRACT

Methods of delaying the onset of an infection or preventing an infection caused by a microbial organism in an internal cavity of a subject are provided. Methods of killing or inactivating microorganisms in at least a portion of the urethra of a subject are provided.

21 Claims, No Drawings

(56) References Cited

U.S. PATENT DOCUMENTS

| | | | |
|---|---|---|---|
| 5,225,473 A | 7/1993 | Duan | |
| 5,231,087 A | 7/1993 | Thornfeldt | |
| 5,234,719 A | 8/1993 | Richter et al. | |
| 5,236,703 A * | 8/1993 | Usala | 424/78.36 |
| 5,256,701 A | 10/1993 | Tamura | |
| 5,260,271 A | 11/1993 | Blackburn et al. | |
| 5,261,896 A * | 11/1993 | Conway et al. | 604/265 |
| 5,270,188 A | 12/1993 | Yamaguchi et al. | |
| 5,284,833 A * | 2/1994 | McAnalley et al. | 514/23 |
| 5,288,492 A | 2/1994 | Morris | |
| 5,304,540 A | 4/1994 | Blackburn et al. | |
| 5,314,915 A | 5/1994 | Rencher | |
| 5,318,955 A | 6/1994 | Mueller et al. | |
| 5,320,772 A | 6/1994 | Tricca | |
| 5,326,567 A | 7/1994 | Capelli | |
| 5,334,582 A | 8/1994 | Blackburn et al. | |
| 5,346,724 A | 9/1994 | Ohgake et al. | |
| 5,362,555 A | 11/1994 | Lal | |
| 5,364,650 A | 11/1994 | Guthery | |
| 5,378,731 A | 1/1995 | Andrews et al. | |
| 5,380,756 A | 1/1995 | Andrews et al. | |
| 5,389,374 A | 2/1995 | Brown-Skrobot | |
| 5,408,022 A | 4/1995 | Imazato et al. | |
| 5,429,819 A | 7/1995 | Oka et al. | |
| 5,434,182 A | 7/1995 | Isaacs et al. | |
| 5,460,802 A | 10/1995 | Asami et al. | |
| 5,460,833 A | 10/1995 | Andrews et al. | |
| 5,462,749 A | 10/1995 | Rencher | |
| 5,466,685 A | 11/1995 | Brown-Skrobot et al. | |
| 5,482,931 A | 1/1996 | Harris et al. | |
| 5,490,992 A | 2/1996 | Andrews et al. | |
| 5,516,510 A | 5/1996 | Beilfuss | |
| 5,516,536 A | 5/1996 | Mikkelsen et al. | |
| 5,547,677 A | 8/1996 | Wright | |
| 5,549,901 A | 8/1996 | Wright | |
| 5,550,145 A | 8/1996 | Olund et al. | |
| 5,569,461 A | 10/1996 | Andrews | |
| 5,624,962 A | 4/1997 | Takeuchi | |
| 5,629,019 A | 5/1997 | Lee et al. | |
| 5,656,591 A | 8/1997 | Tomita | |
| 5,660,842 A | 8/1997 | Petschow | |
| 5,665,776 A | 9/1997 | Yu et al. | |
| 5,705,182 A | 1/1998 | Brown-Skrobot | |
| 5,708,023 A * | 1/1998 | Modak et al. | 514/494 |
| 5,728,756 A | 3/1998 | Gaffar et al. | |
| 5,736,178 A | 4/1998 | Cook et al. | |
| 5,736,574 A | 4/1998 | Burnier et al. | |
| 5,738,643 A | 4/1998 | Stredic, III | |
| 5,747,069 A | 5/1998 | Asakura et al. | |
| 5,753,252 A | 5/1998 | Brown-Skrobot | |
| 5,753,270 A | 5/1998 | Beauchamp | |
| 5,759,584 A | 6/1998 | Traupe et al. | |
| 5,762,948 A | 6/1998 | Blackburn | |
| 5,804,549 A | 9/1998 | Blackburn et al. | |
| 5,817,325 A | 10/1998 | Sawan et al. | |
| 5,862,949 A | 1/1999 | Markey et al. | |
| 5,906,814 A | 5/1999 | Epstein | |
| 5,945,110 A | 8/1999 | Vianen et al. | |
| 5,951,993 A | 9/1999 | Scholz et al. | |
| 5,955,502 A | 9/1999 | Hansen et al. | |
| 5,965,088 A | 10/1999 | Lever et al. | |
| 5,965,610 A | 10/1999 | Modak et al. | |
| 5,968,498 A | 10/1999 | Beerse et al. | |
| 5,968,539 A | 10/1999 | Beerse et al. | |
| 5,989,229 A | 11/1999 | Chiappetta | |
| 5,994,383 A * | 11/1999 | Dyer | A61Q 17/005 424/54 |
| 6,008,261 A | 12/1999 | Genova et al. | 516/58 |
| 6,017,869 A * | 1/2000 | Lu et al. | 510/384 |
| 6,022,551 A | 2/2000 | Jampani et al. | |
| 6,033,705 A | 3/2000 | Isaacs | |
| 6,045,254 A | 4/2000 | Inbar et al. | |
| 6,054,139 A | 4/2000 | Lambert et al. | |
| 6,054,143 A | 4/2000 | Jones | |
| 6,057,274 A | 5/2000 | Bator | |
| 6,071,866 A | 6/2000 | Fujiwara et al. | |
| 6,089,389 A | 7/2000 | Sharon et al. | |
| 6,090,075 A * | 7/2000 | House | 604/172 |
| 6,093,417 A | 7/2000 | Petrus | |
| 6,094,414 A | 7/2000 | Taira et al. | |
| 6,106,851 A | 8/2000 | Beerse et al. | |
| 6,110,516 A | 8/2000 | Hoover et al. | |
| 6,110,908 A | 8/2000 | Eugene | |
| 6,113,933 A | 9/2000 | Beerse et al. | |
| 6,121,327 A | 9/2000 | Tsuzuki et al. | |
| 6,121,329 A | 9/2000 | Fujii et al. | |
| 6,123,933 A | 9/2000 | Hayama et al. | |
| 6,165,494 A | 12/2000 | Picciano | |
| 6,171,611 B1 | 1/2001 | Picciano | |
| 6,177,071 B1 | 1/2001 | Lin et al. | |
| 6,183,757 B1 | 2/2001 | Beerse et al. | |
| 6,183,763 B1 | 2/2001 | Beerse et al. | |
| 6,187,327 B1 | 2/2001 | Stack | |
| 6,187,332 B1 | 2/2001 | Gern et al. | |
| 6,190,674 B1 | 2/2001 | Beerse et al. | |
| 6,190,675 B1 | 2/2001 | Beerse et al. | |
| 6,197,315 B1 | 3/2001 | Beerse et al. | |
| 6,210,695 B1 | 4/2001 | Beerse et al. | |
| 6,211,243 B1 | 4/2001 | Johnson | |
| 6,214,866 B1 | 4/2001 | Drogemoller et al. | |
| 6,217,877 B1 | 4/2001 | Weidner | |
| 6,224,898 B1 | 5/2001 | Balogh et al. | |
| 6,228,383 B1 | 5/2001 | Hansen et al. | |
| 6,238,682 B1 | 5/2001 | Klofta et al. | |
| 6,258,368 B1 | 7/2001 | Beerse et al. | |
| 6,278,008 B1 | 8/2001 | Endo et al. | |
| 6,287,577 B1 | 9/2001 | Beerse et al. | |
| 6,294,186 B1 | 9/2001 | Beerse et al. | |
| 6,319,895 B1 | 11/2001 | Tomita et al. | |
| 6,352,727 B1 | 3/2002 | Takahashi | |
| 6,375,984 B1 | 4/2002 | Kim | |
| 6,383,523 B1 | 5/2002 | Murad | |
| 6,403,069 B1 | 6/2002 | Chopra | |
| 6,414,023 B1 | 7/2002 | Brandsborg | |
| 6,436,430 B1 | 8/2002 | Mulye | |
| 6,440,405 B1 | 8/2002 | Cooper et al. | |
| 6,468,521 B1 | 10/2002 | Pedersen et al. | |
| 6,494,856 B1 | 12/2002 | Zygmont | |
| 6,500,861 B1 | 12/2002 | Wider | |
| 6,506,873 B1 | 1/2003 | Ryan et al. | |
| 6,534,075 B1 | 3/2003 | Hei et al. | |
| 6,548,552 B1 | 4/2003 | Deresiewicz et al. | |
| 6,555,566 B2 | 4/2003 | Ponikau | |
| 6,559,189 B2 | 5/2003 | Baker, Jr. et al. | |
| 6,579,906 B2 | 6/2003 | Cooper et al. | |
| 6,590,051 B1 | 7/2003 | Carter et al. | |
| 6,596,763 B1 | 7/2003 | Thormar et al. | |
| 6,635,676 B2 | 10/2003 | Baker, Jr. et al. | |
| 6,746,635 B2 | 6/2004 | Mathoiwitz et al. | |
| 6,758,857 B2 * | 7/2004 | Cioanta et al. | 607/105 |
| 6,846,846 B2 | 1/2005 | Modak et al. | |
| 6,943,197 B2 | 9/2005 | Maibach et al. | |
| 6,951,642 B2 | 10/2005 | Scholz et al. | |
| 7,030,203 B2 | 4/2006 | Mosbey et al. | |
| 7,569,530 B1 | 8/2009 | Pan | |
| 7,678,389 B1 | 3/2010 | Cordray | |
| 7,858,662 B2 | 12/2010 | Chang | |
| 8,808,722 B2 | 8/2014 | Scholz | |
| 8,840,932 B2 | 9/2014 | Scholz | |
| 9,277,750 B2 | 3/2016 | Scholz | |
| 2002/0013305 A1 | 1/2002 | Calvin | |
| 2002/0025344 A1 | 2/2002 | Newman et al. | |
| 2002/0031556 A1 | 3/2002 | Lindahl | |
| 2002/0037268 A1 | 3/2002 | Stack | |
| 2002/0058010 A1 | 5/2002 | Picard-Lesboueyries | |
| 2002/0086039 A1 | 7/2002 | Lee et al. | |
| 2002/0193417 A1 | 12/2002 | Seidel et al. | |
| 2003/0018306 A1 * | 1/2003 | Bucay-Couto et al. | 604/265 |
| 2003/0147925 A1 | 8/2003 | Sawan et al. | |
| 2003/0152644 A1 | 8/2003 | Modak et al. | |
| 2003/0180380 A1 | 9/2003 | Hansen | |
| 2003/0194447 A1 | 10/2003 | Scholz et al. | |
| 2003/0203915 A1 | 10/2003 | Fang et al. | |
| 2003/0228376 A1 * | 12/2003 | Mody et al. | 424/672 |

(56) References Cited

U.S. PATENT DOCUMENTS

| | | | |
|---|---|---|---|
| 2003/0235626 A1 | 12/2003 | Maibach et al. | |
| 2004/0009130 A1 | 1/2004 | Detore et al. | 424/59 |
| 2004/0052834 A1 | 3/2004 | West | |
| 2004/0091428 A1 | 5/2004 | Libin | |
| 2004/0101557 A1 | 5/2004 | Gibson et al. | |
| 2004/0126414 A1 | 7/2004 | Michaelis | |
| 2004/0186183 A1 | 9/2004 | Johnson | |
| 2004/0247685 A1 | 12/2004 | Modak et al. | |
| 2004/0253139 A1 | 12/2004 | Denton | 422/28 |
| 2004/0265345 A1 | 12/2004 | Perricone | |
| 2005/0019355 A1 | 1/2005 | Denton | 425/401 |
| 2005/0020678 A1 | 1/2005 | Denton | |
| 2005/0031547 A1* | 2/2005 | Tamarkin et al. | 424/45 |
| 2005/0053593 A1 | 3/2005 | Wang | |
| 2005/0058673 A1 | 3/2005 | Scholz et al. | |
| 2005/0089539 A1* | 4/2005 | Scholz et al. | 424/401 |
| 2005/0112188 A1 | 5/2005 | Eliaz et al. | |
| 2005/0118124 A1 | 6/2005 | Reinhart et al. | |
| 2005/0084471 A1 | 11/2005 | Andrews et al. | |
| 2006/0029569 A1 | 2/2006 | Scholz et al. | |
| 2006/0034798 A1 | 2/2006 | Mosbey et al. | |
| 2006/0051384 A1* | 3/2006 | Scholz et al. | 424/405 |
| 2006/0051385 A1* | 3/2006 | Scholz | 424/405 |
| 2006/0052452 A1* | 3/2006 | Scholz | 514/557 |
| 2006/0099237 A1 | 5/2006 | Modak et al. | |
| 2006/0205838 A1 | 9/2006 | Velamakanni | |
| 2006/0275349 A1 | 12/2006 | Andrews | |
| 2006/0276541 A1 | 12/2006 | Tautvydas et al. | |
| 2007/0020029 A1* | 1/2007 | Baumann et al. | 401/135 |
| 2007/0253911 A1* | 11/2007 | Tamarkin et al. | 424/43 |
| 2007/0299409 A1 | 12/2007 | Whitbourne et al. | |
| 2008/0142023 A1 | 6/2008 | Schmid | |
| 2008/0287538 A1 | 11/2008 | Scholz | |
| 2009/0005339 A1 | 1/2009 | Scholz | |
| 2009/0186943 A1 | 7/2009 | Ikeda et al. | |
| 2010/0022654 A1 | 1/2010 | Asmus et al. | |
| 2016/0184346 A1 | 6/2016 | Scholz | |

FOREIGN PATENT DOCUMENTS

| | | | | |
|---|---|---|---|---|
| CH | 634 749 | | 2/1983 | |
| DE | 43 02 812 | | 8/1994 | |
| DE | 43 19 546 | | 12/1994 | |
| DE | 196 42 127 | | 4/1998 | |
| DE | 10156794 | | 6/2003 | |
| DE | 101 61 885 | | 7/2003 | |
| DE | 10 2004 03469 | | 2/2005 | |
| EP | 0 104 346 | | 4/1984 | |
| EP | 0 131 393 | | 1/1985 | |
| EP | 0 156 563 | | 10/1985 | |
| EP | 0 172 724 | | 2/1986 | |
| EP | 0 191 217 | | 8/1986 | |
| EP | 0 243 145 | | 10/1987 | |
| EP | 0 244 144 | | 11/1987 | |
| EP | 0 245 928 | | 11/1987 | |
| EP | 0 253 535 | | 1/1988 | |
| EP | 0 272 149 | | 6/1988 | |
| EP | 0 312 519 | | 4/1989 | |
| EP | 0 375 827 | | 4/1990 | |
| EP | 0 375 827 | A2 | 7/1990 | |
| EP | 0 455 370 | | 11/1991 | |
| EP | 0 465 423 | | 1/1992 | |
| EP | 0 483 835 | | 5/1992 | |
| EP | 0 489 967 | | 6/1992 | |
| EP | 0 497 607 | | 8/1992 | |
| EP | 0 530 861 | | 3/1993 | |
| EP | 0 547 727 | | 6/1993 | |
| EP | 0 567 704 | | 11/1993 | |
| EP | 0 608 433 | | 8/1994 | |
| EP | 0 629 347 | | 12/1994 | |
| EP | 0 876 768 | | 11/1998 | |
| EP | 0 937 812 | | 8/1999 | |
| EP | 1 157 685 | | 11/2001 | |
| EP | 1 449 909 | A1 | 8/2004 | |
| ES | 2 095 183 | | 1/1997 | |
| FR | 2 729 050 | | 7/1996 | |
| GB | 2 053 195 | | 2/1981 | |
| GB | 2 193 892 | | 2/1988 | |
| GB | 2 323 784 | | 10/1989 | |
| GB | 2 338 649 | | 12/1999 | |
| JP | 72022252 | | 9/1968 | |
| JP | 51-15669 | | 2/1976 | |
| JP | 51-139645 | | 2/1976 | |
| JP | 76-84022 | | 9/1976 | |
| JP | 51106731 | | 9/1976 | |
| JP | 52-07428 | | 1/1977 | |
| JP | 52003859 | | 1/1977 | |
| JP | 77-22781 | | 2/1977 | |
| JP | 52-33181 | | 8/1977 | |
| JP | 77-73621 | | 9/1977 | |
| JP | 53 066415 | | 6/1978 | |
| JP | 53-091126 | | 8/1978 | |
| JP | 79032058 | | 10/1979 | |
| JP | 56-43211 | | 4/1981 | |
| JP | 83018050 | | 11/1981 | |
| JP | 57176903 | | 10/1982 | |
| JP | Sho 59-163477 | | 9/1984 | |
| JP | 359196816 | A * | 11/1984 | A61K 99/10 |
| JP | 60-44539 | | 3/1985 | |
| JP | 85043111 | | 9/1985 | |
| JP | 61-152269 | | 10/1986 | |
| JP | 63-0166837 | | 2/1987 | |
| JP | 62-48612 | | 3/1987 | |
| JP | 63-130541 | | 6/1988 | |
| JP | 1-256343 | | 10/1989 | |
| JP | 2-46255 | | 2/1990 | |
| JP | 02-116302 | | 5/1990 | |
| JP | 3067573 | | 3/1991 | |
| JP | 4016173 | | 1/1992 | |
| JP | 4018003 | | 1/1992 | |
| JP | 05 229915 | | 9/1993 | |
| JP | 05-320067 | | 12/1993 | |
| JP | 6022730 | | 1/1994 | |
| JP | 8-151326 | | 11/1994 | |
| JP | 07-039356 | | 2/1995 | |
| JP | 8-40861 | | 2/1996 | |
| JP | 08-056631 | | 3/1996 | |
| JP | 8099878 | | 4/1996 | |
| JP | 8099887 | | 4/1996 | |
| JP | 08-175989 | | 7/1996 | |
| JP | 8-187070 | | 7/1996 | |
| JP | 8205771 | | 8/1996 | |
| JP | 9067593 | | 3/1997 | |
| JP | 9-510976 | | 11/1997 | |
| JP | 10508337 | | 8/1998 | |
| JP | 11113780 | | 4/1999 | |
| JP | Hei 11-113779 | | 4/1999 | |
| JP | 11302462 | | 11/1999 | |
| JP | 11-349418 | | 12/1999 | |
| JP | 3040282 | | 5/2000 | |
| JP | 2000-295976 | | 10/2000 | |
| JP | 2001 226205 | | 8/2001 | |
| JP | 2001 323298 | | 11/2001 | |
| JP | 2002-145736 | | 5/2002 | |
| JP | 2001-53564 | | 9/2002 | |
| JP | 2002-255711 | | 9/2002 | |
| JP | 2002-322090 | | 11/2002 | |
| KR | 9105620 | | 8/1991 | |
| WO | WO 82/03173 | | 9/1982 | |
| WO | WO 89/02754 | | 4/1989 | |
| WO | WO 89/12399 | | 12/1989 | |
| WO | WO 92/21320 | | 12/1992 | |
| WO | WO 93/15018 | | 8/1993 | |
| WO | WO 93/20812 | | 10/1993 | |
| WO | WO 93/21906 | | 11/1993 | |
| WO | WO 94/18943 | | 9/1994 | |
| WO | 94/27440 | | 12/1994 | |
| WO | WO 95/07616 | | 3/1995 | |
| WO | WO 95/24179 | | 9/1995 | |
| WO | 95-26134 | | 10/1995 | |
| WO | WO 95/31956 | | 11/1995 | |
| WO | WO 96/02228 | | 2/1996 | |
| WO | WO 96/25469 | | 8/1996 | |
| WO | WO 96/29867 | | 10/1996 | |

(56) References Cited

FOREIGN PATENT DOCUMENTS

| | | | |
|---|---|---|---|
| WO | 97/000076 | 1/1997 | |
| WO | WO 97/00076 | 1/1997 | |
| WO | WO 97/00163 | 1/1997 | |
| WO | WO 97/11912 | 4/1997 | |
| WO | WO 97/16168 | 5/1997 | |
| WO | WO 97/23577 | 7/1997 | |
| WO | WO 97/25032 | 7/1997 | |
| WO | WO 98/09520 | 3/1998 | |
| WO | WO 98/14189 | 4/1998 | |
| WO | WO 99/11237 | 3/1999 | |
| WO | 99/24036 A1 | 5/1999 | |
| WO | WO 99/22703 | 5/1999 | |
| WO | WO 99/37172 | 7/1999 | |
| WO | WO 99/44444 | 9/1999 | |
| WO | WO 99/59538 | 11/1999 | |
| WO | WO 99/60998 | 12/1999 | |
| WO | WO 99/66793 | 12/1999 | |
| WO | WO 00/01351 | 1/2000 | |
| WO | WO 00/03612 | 1/2000 | ............... A23L 3/00 |
| WO | WO 00/04118 | 1/2000 | |
| WO | WO 00/69267 | 11/2000 | |
| WO | WO 00/71183 | 11/2000 | |
| WO | WO 00/71789 | 11/2000 | |
| WO | WO 00/78141 | 12/2000 | |
| WO | WO 01/12155 | 2/2001 | |
| WO | 01/28552 | 4/2001 | |
| WO | WO 01/24839 | 4/2001 | |
| WO | WO 01/43549 | 6/2001 | |
| WO | WO 02/26261 | 4/2002 | |
| WO | WO 02/47637 | 6/2002 | |
| WO | WO 02/089849 | 11/2002 | |
| WO | WO 02/100244 | 12/2002 | |
| WO | WO 02/102244 A1 | 12/2002 | |
| WO | WO 03/022211 | 3/2003 | |
| WO | 03-032948 | 4/2003 | |
| WO | WO 03/028767 | 4/2003 | |
| WO | WO 03/037293 | 5/2003 | |
| WO | WO 03/047636 | 6/2003 | |
| WO | 03/089007 A1 | 10/2003 | |
| WO | WO 04/032927 | 4/2004 | |
| WO | 04-052308 | 6/2004 | |
| WO | WO 04/062643 | 7/2004 | |
| WO | WO 2005/002482 A1 | 1/2005 | |
| WO | WO 05/022998 | 3/2005 | |
| WO | WO 05/023233 | 3/2005 | |
| WO | WO 2005/009353 | 3/2005 | |
| WO | WO 05/102287 | 11/2005 | |
| WO | WO 2006/026876 | 3/2006 | ............ C07C 69/675 |
| WO | WO 2006/029351 | 3/2006 | ............. A01N 59/00 |
| WO | 2007-094332 | 8/2007 | |
| WO | 2008-057773 | 5/2008 | |

OTHER PUBLICATIONS

"Indwelling catheter infection", Canadian Medical Association Journal, 1973/vol. 109, Oct. 20, p. 711-713.*
Schiøtz : Antiseptic catheter gel and urinary tract infection after short-term postoperative cauterization in women, Archives of Gynecology and Obstetrics, 1996, 258: 97-100.*
Klaus et al.: Analysis of the antimicrobial activity of local anaesthetics used for dental analgesia, Journal of Medical Microbiology, 2008, 57, 88-94.*
Your Urinary System and How It Works: retrieved from internet: http://kidney.niddk.nih.gov/kudiseases/pubs/yoururinary/.Retrieved on Jul. 2, 2013.*
Schiøtz: Antiseptic catheter gel and urinary tract infection after short-term postoperative catheterization in women, Arch Gynecol Obstet, 1996, 258, pp. 97-100.*
Lucinda: retrieved from internet: www.fda.gov/ohrms/dockets/ac/03/slides/3926S1_11_Buhse.ppt. Retrived on May 11, 2015.*
Urethroplasty: retrieved from internet: https://www.centerforreconstructiveurology.org/urethral-stricture/open-repair-urethroplasty/#.Vio4PU2FPbo. Retrieved on Oct. 23, 2015.*
Cystoscopy: retrieved from internet: https://www.nlm.nih.gov/medlineplus/ency/article/003903.htm. Retrieved on Apr. 13, 2016.*
Cocodimonium hydroxypropyl silk amino acids: retrived frominternet: http://www.saapedia.org/en/saa/?type=detail&id=4166. Retrieved on Apr. 13, 2016.*
Liquid gels: retrieved from internet: https://www.walgreens.com/q/liquid+gels. Retrieved on Nov. 28, 2016.*
Surgical skin preparation and Foley catherization & quick check; retrieved from internet: https://quizlet.com/45137717/surgical-skin-preparation-and-foley-catherization-quick-check-flash-cards/. retrieved on Nov. 29, 2017.*
Behaviours and rituals in the operating theatre: A Report from the Hospital Infection Society Working Party on Infection Control in Operating Theatres: https://ac.els-cdn.com/S019567010291220X/1-s2.0-S019567010291220X-main.pdf?_tid=060f97dc-d47c-11e7-9105-00000aacb35d&acdnat=1511901660_92e05cb8995531ab601fa90d038fb4fa. retrieved on Nov. 29, 2017.*
The ABCs of Infection Control: retrieved form internet: http://www.infectioncontroltoday.com/articles/2003/05/the-abcs-of-infection-control.aspx. retrieved on Nov. 29, 2017.*
Overview of catheter-related infections with special emphasis on prevention based on educational programs: retrieved from Internet: http://www.sciencedirect.com/science/article/pii/S1198743X1462797X. retrieved on Nov. 29, 2017.*
Mannose may be useful for treating uterine infections [retrieved from the internet on Apr. 9, 2003], URL http://www.equinescienceupdate.co.uk/mannos.htm.
NutritionalTest.com, 10105 E Via Linda #103-192, Scottsdale, AZ 85258. Take the guess work out of taking nutrients, D. Mannose [retrieved from the internet on Apr. 9, 2003], URL <http://www.nutritionaltest.com/dmannose.html>.
Rutala et al.Susceptibility of Antibiotic-Auaceptibke and Antibiotic-Resistant Hospital Bacteria to Disinfectants. Infection Control and Hospital Epidemiology Jun. 1997, vol. 18, No. 6, pp. 417-421.
Gokalp et al. "Antimicrobial Screening of Mentha piperita Essential Oils, J. Agric", Food Chem. 2002, 50, 3943-3946.
ABDA: Rezepturhinweise: Triclosan in Dermatika"NRF—Neues Rezeptur Formularium" pp. 1-4 XP002391034, (Apr. 16, 2004).
Ahvenainen, "New approaches in improving the shelf life of minimally processed fruit and vegetables," *Trends in Food Science & Technology*, vol. 7, pp. 179-187 (Jun. 1996).
Baker et al., "Antimicrobial Properties of Lauricidin in Mechanically Deboned Chicken, Minced Fish and Chicken Sausage" *J. of Food Safety*, vol. 4, pp. 177-184 (1982).
Bell et al, "The Efficacy of Nisin, Sorbic Acid and Monolaurin as Perservatives in Pasteurized Cured Meat Products" *Food Microbiology*, vol. 4, pp. 277-283 (1987).
Block, S., "Acid-Anionic Surfactant Sanitizers", Disinfection, Sterilization and Preservation, Chapter 16, Lea & Febiger, Philidelphia PA, pp. 319-323 (1977).
Boddie, R.L., "Evaluation of postmilking teat germicides containing Lauricidin, saturated fatty acids and lactic acid", *Stn Caplus*, vol. 6, No. 117, XP002030991 (1992).
Branen, J.K., et al., "Enhancement of nisin, lysozyme, and monolaurin antimicrobial activities by ethylenediaminetetraacetic acid and lactoferrin", *Intl Journal of Food & Microbiology*, vol. 90, No. 1, pp. 63-74 XP002316393 (Jan. 1, 2004).
Chavigny, K.H., "The Use of polymixin B as a urethral lubricant to reduce the post-instrumental incidence of bacteiuria in females", *Int. J. Nurs. Stud.*, vol. 12, pp. 33-42, (1975).
Federal Register, 21 CFR Parts 333 and 369, Tentative Final Monograph for Healthcare Antiseptic Drug Products; Proposed Rule (1994).
Flournoy, et al., "The Role of Lauricidin as an Antimicrobil Agent" *Drugs of Today*, vol. 21 No. 8, pp. 373-377 (1985).
Gillespie, W.A., et al., "Prevention of Catheter Infection of Urine in Female Patients", *British Medical Journal*, pp. 13-16 (1962).
Gloor, M., et al., "Triclosan, ein dermatologishes Lokaltherapeutikum" Hautarzt, vol. 53, pp. 724-729, XP002391035, (Nov. 2002).
Hall et al., "Spice Extracts, Lauricidin, and Propylene Glycol as Inhibitors of Clostridium Botulinum in Turkey Frankfurter Slurries", *Poultry Science*, vol. 65, No. 6, pp. 1167-1171 (1986).

(56) References Cited

OTHER PUBLICATIONS

Hill, R.L. and M.W. Casewell, "The in-vitro activity of povidone-iodine cream against *Staphylococus aureas* and its bioavailability in nasal secretions", *Journal of Hospital Infection*, vol. 45, pp. 198-205 (2000).
Izat et al., "The Use of Propylene Glycol and/or Lactic Acid in Chill Water for Reducing Salmoneallae on Broilers" *J. of Food Processing and Preservation*, vol. 14, pp. 369-374 (1990).
Kabara, J.J., et al. "Antimicrobial Lipids: Natural and Synthetic Fatty Acids and Monoglycerides", *Lipids*, Champaign, IL, vol. 12, No. 9, pp. 753-759 XP000563038 (Sep. 1, 1977).
Kabara, "GRAS Antimicrobial Agents for Cosmetic Products", *J. Soc. Cosmet. Chem.* vol. 31, pp. 1-10 (1980).
Kabara, "Food-Grade Chemicals for Use in Designing Food Preservative Systems", *J. of Food Protection*, vol. 44, pp. 633-647 (1981).
Kabara, A New Preservative System for Food, *J. of Food Safety*, vol. 4, pp. 13-25 (1982).
Kabara, "Medium-Chain Fatty Acids and Esters as Antimicrobial Agents" *Cosmetic and Drug Preservation*, vol. 16, pp. 275-304 (1984).
Kato et al., "Combined Effect on Different Drugs on the Antibacterial Activity of Fatty Acids and their Esters", vol. 4, pp. 355-363 (1975).
Kato, et al., "Combined Effect of Citric and Polyphosphoric Acid on the Antibacterial Activity of Monoglycerides", vol. 4, No. 6 pp. 254-261 (1976).
Kiser, K. et al., "Development and Characterization of *Staphylococcus aureus* Nasal Colonization Model in Mice," *Infect and Immunity*, vol. 67, No. 10, pp. 5001-5006 (1999).
Kostiala, A.A.I., et al., "Effect of nitrofurantoin and methenamine hippurate prophylaxis on bacteria and yeasts in the urine of patients with an indwelling catheter", *J. of Hospital Infection*, vol. 3, pp. 347-364 (1982).
Macfarlane, D.E., "Prevention and treatment of catheter-associated urinary tract invections", *J. of Infection*, vol. 10, pp. 96-106 (1985).
May, et al., "Time-kill studies of tea tree oils on clinical isolates", *J. of Antimicrobial Chemotherapy*, vol. 45, pp. 639-643 (2000).
Mead et al., "Food-Related Illness and Death in the United States", *Emerg. Infect. Dis.*, vol. 5, No. 5, pp. 607-625 (1999).
Merianos, "Chapter 13, Quaternary Ammonium Antimicrobial Compounds," in Disinfection, Sterilization, and Preservation, 4th Ed., Block, Ed., Philadelphia, PA, Title page, Publication page, and Chapter 13 (pp. 225-255), (1991).
Morgan, D. M., "Urinary tract infection in hospitalized patients", *Canadian Hospital*, pp. 27-30 (1973).
Nakagaki, et al., "Solubility & Hydrolysis Rate of I-Monolaurin in Aqueous Solutions", *Yakugaku Zasshi*, vol. 90, No. 10, pp. 1310-1315 (1970).
Nicoletti, G. et al., The Antimicrobial Activity in vitro of chlorhexidine, a mixture of isothiazolinones (Kathon CG) and cetyl trimethyl ammonium bromide (CTAB), *Journal of Hospital Infection*, vol. 23, pp. 87-111 (1993).
Oh, et al., "Enhanced Inhibition of Listeria monocytogenes by Glycerol Monolaurate with Organic Acids", *Journal of Food Science*, vol. 59, No. 6, pp. 1258-1261 (1994).
Perez-Roth, E. et al. "Mupirocin resistance in methicillin-resistant *Staphylococcus aureus* clinical isolates in a Spanish hospital. Co-application of multiplex PCR assay and conventional microbiology methods", *Diag. Micro. Infect. Dis.*, vol. 43, pp. 123-128 (2002).
Perl, T. et al., "New Approaches to Reduce *Staphylococcus aureua* Nosocomial Infection Rates: Treating *S. aureus* Nasal Carriage", *Ann. Pharmacother.*, vol. 32, pp. S7-S16 (1998).
Physician's Desk Reference, definition of the composition of Aquaphor, p. 685, Edition (1993).
Product Information Brochure, Sensive SC 50 a multifunctional additive, Schuelke & Mayer (16 pgs.) (Nov. 2006).

Projan, et al., "Glycerol Monolaurate Inhibits the Production of β-Lactamase, Toxic Shock Syndrom Toxin-1, and Other Staphylococal Exoproteins by Interfering with Signal Transduction" *Journal of Bacteriology*, vol. 176, No. 14, pp. 4204-4209 (Jul. 1994).
Remington's Pharmaceutical Services, definition of absorption base, 14th Ed., p. 1600 (1970).
Respiratory mucosa: the core of infection and inflammation, Title page, Editorial page, pp. 1-32, Product information page, and Publication page (36 pgs. Total).
Rice, J. "Organic acid sprays," *Food Processing*, pp. 45, 47-48, 50 (Apr. 1994).
Sawhney, A.S. et al., "Bioerodible Hydrogels Based on Photopolymerized Poly(ethylene glycol)-co-poly(a-hydroxy acid) Diacrylate Macromers", *Macromolecules*, vol. 26, pp. 581-587 (1993).
Schemmel et al., "Monolaurin As an Anticaries Agent", Chapter 4, *Symposium on the Pharmacological Effect of Lipds*, pp. 37-43 (1983).
Sciarra and Cutie, "Aersols," Chapter 92 in Remington's Pharmaceutical Sciences, 18th edition, pp. 1694-1712 (1990).
Silverman, Chapter 44 in *Disinfection, Sterilization, and Preservation*, First addition, C. A. Lawrence and S.S. Block (1968).
Stecker, Ph.D., "Chapter 14, The Salicylanilides and Carbanilides," in Disinfection, Sterilization, and Preservation, 2nd Ed., Block, Ed., Philadelphia, PA, Title page, Publication page, and Chapter 14 (pp. 282-300) (1977).
United States Pharmacopeia Official Monographs for Povidone-Iodine, Assay for Available Iodine (pp. 1600-1602).
Vadehra et al., "Comparison of Antibacterial Properties of Lauricidin® and BHA against Antibotic Resistant and Sensitive Strains of *Staphylococcus aureus* and *Pseudomonos aeruginosa*" *AOCS Monograph* vol. 13, No. 2, pp. 77-87, XP000560207 (1985).
Venkitanarayanan et al., "Inactivation of *Escherichia coli* 0157:H7 by combinations of GRAS chemicals and temperature", *Food Microbiology*, vol. 16, pp. 75-82 (1999).
Vorum, H. et al., "Solubility of Long-Chain Fatty Acids in Phosphate Buffer at pH 7.4," *Biochimica et. Biophysica Acta*, vol. 1126, pp. 135-142 (1992).
Wakabayashi, et al., Increased Staphylococcus-killing Activity of an Antimicrobial Peptide, Lactoferricin B, with Minocycline and Monoacylglyserol, *Bioscience Biotechnology and Biochemistry* vol. 66, No. 10, pp. 2161-2167 (Oct. 2002).
Wang et al., "Inhibition of *Listeria monocytogenes* by Monoacylglycerols Synthesized from Coconut Oil and Milkfat by Lipase-Catalzed Glycerolysis"*J. of Agric. Food Chem.*, vol. 41, pp. 1000-1005 (1993).
Watanabe, H. et al., "Low Concentrations of Mupirocin in the Pharynx following Intranasal Application May Conrtibute to Mupirocin Resistance in Methicillin-Resistant *Staphylococcus aureus,"* *J. Clin. Micro.*, vol. 39, No. 10 pp. 3775-3777 (2001).
Whitley, et al., "Herpes zoster: focus on treatment in older adults", *Antiviral Research* vol. 44, pp. 145-154 (1999).
Williams, J.D., et al., "Trials of Five Antibacterial Creams in the Control of Nasal Carriage of Staphylococcus Aureus", *The Lancet*, vol. 290, Issue 7512, pp. 390-392 (Aug. 1967).
Williamson et al., "A New Method for the Quantitative Investigation of Cutaneous Bacteria," J. Invest. Derm., vol. 45, pp. 498-503 (1965).
Wooley, "EDTA-tris Potentiation of Antimicrobial Agents", *Modern Veterinary Practice*, pp. 113-116 (1983).
http://www.lungusa.org/site/pp.asp?c=dvLUK9O0E&b=35873.
http://www.merck.com/mmhe/sec06/ch089/ch089d.html.
Database Medline—US National Library of Medicine (NLM) Jul. 1992, Kida N. etal. "Effect of pH on preferential antibacterial-activity of ethylenediaminetetraacetic acid (EDTA)" XP002400661 Database accession No. NLM1433911.
Van Putten, P.L.; "Mandelic acid and urinary tract infections"; Antonie van Leeuwenhoek, International Journal of General and Molecular Microbiology 1979 NL; vol. 45, No. 4, 1979 pp. 622.
Merck Manual of Diagnosis and Therapy, Seventeenth Edition, Published 1999 by Merck Research Laboratories, pp. 673-677.
Merriam-Webster's Collegiate Dictionary, published 1998 by Merriam-Webster, incorporated, p. 924.

(56) References Cited

OTHER PUBLICATIONS

Physicians Desk Reference, to Pharmaceutical Specialties and Biologicals, 26th Edition, 1972, Publisher Charles E Baker.
Elliott et al., "Bladder Irrigation or Irritation?" *British Journal of Urology*, 1989;64:391-394.
Schneeberger et al., "A randomized study on the effect of bladder irrigation with povidone-iodine before removal of an indwelling catheter," *J. of Hospital Infection*, 1992;21:223-229.
Van Den Broek et al., "Bladder Irrigation with Povidone-Iodine in Prevention of Urinary-Tract Infections associated with Intermittent Urethral Catheterisation," *The Lancet*, Mar. 9, 1985;563-565.
Romanies et al., Cunningham's Textbook of Anatomy, 12th Ed., Oxford University Press, 1981 p. 551.
"Anterior vaginal wall repair (surgical treatment of urinary incontinence)-series," University of Maryland Medical Center, 2013 (last accessed Jan. 13, 2014), https://umm.edu/health/medical/ency/presentations/anterior-vaginal-wall-repair-surgical-treatment-of-urinary-incontinence-series.
Bickley et al., Bates' Guide to Physical Examination and History Taking, 10th Edition, 2009, Lippincott Williams & Wilkins; Chapter 13, p. 502 (last accessed Jan. 13, 2014), http://www.uptomed.ir/Digimed.ir/Bates-History-Taking-10th-Edition/Bates_History_Taking_10th_Edition/Ovid-_Bates'_Guide_to_Physical_Examination_and_History_Takin-17/.
Caprylic/capric triglyceride: retrieved from internet: http//www.thegoodscentscompany.com/data/rw1306031.html. Retrieved on Jul. 24, 2015 (7 pgs).
Frey, "Structure, Ordering, and Activity of Lipid/Polymer Systems, Volume One", 2008, UMI Microform 3322585, ProQuest LLC, Ann Arbor, Michigan, 3 pages.
Hait et al., "Determination of Critical Micelle Concentration (CMC) of Nonionic Surfactants by Donor-Acceptor Interaction with Iodine and Correlation of CMC with Hydrophile-Lipophile Balance and Other Parameters of the Surfactants", Jul. 2001, *Journal of Surfactants and Detergents*; 4(3):303-309.
Sasol, "Excipients for pharmaceuticals", Brochure, 2010, SASOL Olefins & Surfactants GmbH, Hamburg, Germany; 28 pages. Retrieved from the Internet on Oct. 29, 2015, at <http://www.sasoltechdata.com/MarketingBrochures/Excipients_Pharmaceuticals.pdf>.
Surber, et al.(Eds.), "Topical Applications and the Mucosa", 2011, *Curr. Probl Dermatol. Basel*, Karger, 40:116-124.
Theriault et al., "Leakage Associated With Urinary Catheter Usage" 2012, *Urol Nurs*, 32(6):307-312. Retrieved online Feb. 25, 2016, from <http://www.medscape.com/viewarticle/778654>.
Timar-Balazsy et al., "Chemical Principles of Textile Conservation", 2011, Routledge, Abingdon, Oxon, Oxford, United Kingdom, 4 pages.
Data Sheet. 2006. Malvern Instruments Ltd. Malvern UK. 5 pages. "Surfactant micelle characterization using dynamic light scattering".
Kerleta et al. 2010. *Altex* 27. 191-197. Retrieved from internet: http://www/.altex.ch/resources/altex_2010_3_191_197_Kerteta.pdf. Retrieved on Jan. 6, 2016. "Poloxamer 188 Supplemented Culture Medium Increases the Vitality of Caco-2 Cells after Subcultivation and Freeze/Thaw Cycles".
Mandavi. 2011. Ch 2. *Kinetic Studies of Some Esters and Amides in Presence of Micelles*. Pt. Ravishankar Shukla University, Raipur, Chhattisgarh, India. pp. 55-105. "Critical Micelle Concentration of Surfactant, Mixed Surfactant and Polymer by Different Methods at Room Temperature and Its Importance".
Choe et al. 2006. *Arch Facial Plast Surg*. 8:319-323. "The Korean Woman's Nose".
Attwood, D., and Florence, A.T. "Surface Activity." *Surfactant Systems, Their chemistry, pharmacy and biology*. 1983. Chapman and Hall, 1985, pp. 1-3.
Gad: Pharmaceutical Manufacturing Handbook Production and Process, John Wiley & Sons, Inc., Hoboken, New Jersey, 2008. p. 411.
Khosharay et al. "Re: Can PEG 400 form micelle?" [Blog comments]. ResearchGate, 8th Aug. 2016, https://www.researchgate.net/post/Can_PEG_400_form_micelle. Accessed Jun. 7, 2019.
Rahaman et al. 2013. *Bangladesh Pharmaceutical Journal*. 16(1):77-80. "Capacity of Non Ionic and Ionic Surfactants for Solubilisation of Paracetamol".

\* cited by examiner

METHODS OF REDUCING MICROBIAL CONTAMINATION

CROSS REFERENCE TO RELATED APPLICATIONS

This application is a national stage filing under 35 U.S.C. 371 of PCT/US2006/009009 filed Mar. 10, 2006, which claims the benefit of U.S. Provisional Application No. 60/660,830, filed Mar. 10, 2005, the disclosure of which is incorporated by reference in its entirety herein.

BACKGROUND

The present invention relates to prevention and or delayed onset of infections associated with introduction of an instrument into an external mammalian body opening. The external body opening may be natural or created. The infections are typically associated with organs which may be at least intermittently filled with fluid. The fluid may result from a natural or artificial condition or due to an inflammatory response. In particular this invention relates to prevention of infection associated with NG tubes, peritoneal dialysis, and especially to prevention of infections associated with indwelling urinary catheters.

Although certain cavities are typically low in bacteria count and are classified as infection free, the instillation of conventional instrumentation, including tubes and catheters, into these cavities is often accompanied by a large number of infections or high incidence of elevated bacteria count such as bacteriuria (that is, a relatively high bacteria count in the urine with no clinical signs of infection). These infections often result in a cavity remote from the external opening leading to the cavity. For example, many bladder infections are believed to be a result of bacteria introduced from insertion of the catheter through the meatus and urethra into the bladder. The opening may be colonized with microorganisms (e.g., bacteria and fungi) with no signs of a clinical infection. The urinary tract is the most common site of nosocomial infection, accounting for more than 40% of the total number reported by acute-care hospitals and affecting an estimated 600,000 patients per year according the CDC Guideline for Prevention of Catheter-associated Urinary Tract Infections. A nosocomial infection is an infection acquired during hospitalization which was not present or incubating when the patient was admitted to the hospital. The majority of urinary tract infections are associated with indwelling urethral catheters or other types of urethra and bladder penetrating instrumentation. Infections resulting from urinary catheters have been responsible for excess mortality as well as morbidity among the catheterized population and have been the subject of numerous, and most often at least partly unsuccessful, attempts to control or prevent same.

The uninstrumented bladder is usually sterile or very low in bacteria count, Passage of a catheter through the urethra offers a portal for organisms that may overwhelm the bladder's defenses. One source of urethral organisms are those organisms that are carried into the bladder by insertion of the catheter. The urethra has been shown to be heavily colonized in several studies. Catheters not removed immediately but left indwelling offer additional opportunities for entry of bacteria. A frequent source for the infecting organisms is endogenous from the patient's own fecal or urethral flora. Once these organisms are in the periurethral area they may travel into the bladder between the urethral mucosae and the external catheter surface. This may be aided by catheter movement. An additional source for the infection is exogenous contamination by hospital personnel at the junction of the catheter and the collecting tube or drain hose on the collecting bag. Thus, attempts to disinfect the collecting bag reduce but do not eliminate these nosocomial infections, especially since the infections are more frequent in women apparently due to contamination of the periurethral area. In addition, there have been numerous attempts to make antimicrobial coated catheters, however, these have not produced the drop in infection rate desired. The most common treatment reported is the use of antimicrobial impregnated catheters such as silver hydrogel coatings commercially available on the Bardex catheter (CR Bard). This coating is said to be bacteriostatic rather than bactericidal. Many silver coated urinary tract catheters have proven to be ineffective. None of the prior art catheters and methods have been fully successful in preventing or controlling the urinary tract infections associated with such catheters.

Various types of bladder irrigations have been attempted to prevent or eliminate infection accompanying catheterization. Bladder irrigation with antimicrobial agents is probably the most widely practiced attempt to prevent urinary tract infection subsequent to catheterization. Since entry of bacteria was not preventable in the early techniques wherein the catheter systems were open, it was postulated that an irrigation with antimicrobial solutions would prevent multiplication of organisms and possibly the development of bacteriuria. Irrigation in open systems by continuous and intermittent methods have both been used. An intermittent irrigation often included the addition of a solution including the antimicrobial agent into the bladder through the catheter drainage lumen. The lumen was then clamped and the solution retained for a short time. This technique was used for prevention of bacterial infection in patients with indwelling urinary catheters and those receiving intermittent catheterization. This method was not greatly effective in preventing bacteria.

Another problem associated with previous attempts to prevent urinary tract infections has been that a totally satisfactory solution for killing and preventing growth of microorganisms was not recognized. Various solutions were used with varying effects. For instance, use of an antibiotic solution often resulted in prevention of some bacterial growth when the bacteria was effected by the antibiotic; however, other resistant bacteria will be immune to a particular antibiotic and these continue to grow. Also yeast and certain other non-bacteria microorganisms are normally not affected by antibiotics.

Certain particular problems with infection occur in other parts of the abdominal cavity. For example, peritonitis is one of the most common complications of peritoneal dialysis. As many as 46% of patients undergoing dialysis have been shown to have an occurrence of peritonitis before the end of the first year of treatment. Attempts at prevention of peritonitis have been unsuccessful, thus leaving infection a major threat to dialysis patients.

Another treatment includes the use of antiseptic and antibiotic ointments instilled in the urethra or applied to the catheter/instrument surface. For example, polymycin B in combination with very low levels of benzalkonium chloride (LUBRASPORIN) has been applied to the exterior surface of a catheter, however, no reduction in infection was associated with the treatment. LUBRASPORIN has also been instilled into the urethra 7-10 minutes (min) prior to insertion of the catheter as well as onto the catheter itself; however, the treatment was not very effective. Five out of fourteen patients still acquired infections. This is likely due at least in part to the poor antimicrobial spectrum of polymyxin B and the low concentration of benzalkonium chloride present in the gel. Others evaluated two urethral antiseptics: hydrargaphen ("penotrane") urethral jelly containing dinaphthylmethane disulphonate (0.05%) and a local anaesthetic or chlorhexidine gluconate (CHG) in a mixture of polyethylene glycols. The CHG composition was effective at reducing Gram negative bacilli infections but not those caused by *Str. faecalis*. The authors conclude that this may be due to the poor activity of CHG toward *Str. faecalis*. It is also probable that the CHG compositions did not kill *Str. faecalis* due to a lack of surfactant in the formulation. It is believed that generally complete wetting of the tissue is desirable to ensure rapid antimicrobial activity.

The standard practice today advocated by many advisory groups is to apply povidone iodine solutions such as are marketed under the name BETADINE to the external meatus. On a male this involves circling the tip of the penis with a povidone iodine saturated cotton ball 3 times. On a female this involves three saturated cotton balls are used. The first is wiped down the left labia. The second is wiped down the right labia and the final saturated cotton ball is wiped over the meatus.

It is generally recognized that bacteria may enter the catherterized bladder by two routes: intraluminally; and extraluminally. Intraluminal infections have been greatly reduced in recent years through the use of closed drainage systems. Many of the modalities discussed above have been attempted to reduce extraluminal infections; however, these still account for two thirds of all Catheter Associated Urinary Tract Infections (CAUTIs).

It should be noted that the use of antimicrobial agents (e.g., antibiotics, antiseptics) plays an important part in current medical therapy. For decades medicine has relied primarily upon antibiotics to fight systemic as well as topical infections. For example, bacitracin, neomycin sulfate, polymyxin B sulfate, gentamicin, framycetin-gramicidin, lysostaphin, methicillin, rifampin, tobramycin, nystatin, mupirocin, and combinations thereof, as well as many others, have been used with varying success.

Antibiotics are generally effective at very low levels and are often safe with very few, if any, side effects. Often antibiotics have little or no toxicity to mammalian cells. Thus, they may not retard, and can even enhance, wound healing. Antibiotics are generally of a narrow spectrum of antimicrobial activity. Furthermore, they often act on very specific sites in cell membranes or on very specific metabolic pathways. This can tend to make it relatively easy for bacteria to develop resistance to the antibiotic(s) (i.e., the genetically acquired ability to tolerate much higher concentrations of antibiotic) either through natural selection, transmission of plasmids encoding resistance, mutation, or by other means.

Antiseptics, on the other hand, tend to have broader spectrum of antimicrobial activity and often act by nonspecific means such as disruption of cell membranes, oxidation of cellular components, denaturation of proteins, etc. This nonspecific activity makes it difficult for resistance to develop to antiseptics. For example, there are very few reports of true resistance to antiseptics such as iodine, lower alcohols (ethanol, propanol, etc.), chlorhexidine, quaternary amine surfactants, chlorinated phenols, and the like. These compounds, however, need to be used at concentrations that often result in irritation or tissue damage, especially if applied repeatedly. Furthermore, unlike antibiotics, many antiseptics are not active in the presence of high levels of organic compounds. For example, formulations containing iodine or quaternary ammonium compounds have been reported to be inactivated by the presence of organic matter such as that in nasal or vaginal secretions, and perhaps even on skin.

Many antiseptic compounds are viewed as irritants. For example, compositions containing iodine and/or chlorhexidine have been reported to cause skin irritation. Mucosal tissues, such as the urethra, which can have a high level of microbial colonization in certain otherwise healthy individuals, may be particularly sensitive to irritation.

Also, for most applications the compositions should cause no or minimal irritation or burning.

Also, many conventional antimicrobial compositions are too low in viscosity and/or too hydrophilic in nature to maintain sufficient substantivity and persistence to provide sufficient antimicrobial activity on moist tissue, such as the urethra.

Thus, there is still a need for additional antimicrobial compositions.

SUMMARY

The present invention provides methods of using antimicrobial compositions. Such compositions are typically useful when applied topically to microbially colonized tissue, which is to be contacted by an instrument (e.g., a catheter).

More particularly, this invention relates to decolonization of the internal surface of an opening, which can be an orifice, a channel, a canal (e.g., a urethra) that leads to an internal body space (e.g., an internal cavity such as the bladder) that is prone to infection. Examples of such openings include the urethra which leads to the bladder, the noseand sinuses that lead to the upper sinuses, as well as created openings such as the opening that forms the entry point for peritoneal dialysis. These tissues are often very moist mucosal or mucosal-like tissues (i.e., mucous membranes) that may be very sensitive to abrasion, damage, and irritation.

For example, the present invention provides methods of delaying the onset of an infection or preventing an infection caused by a microbial organism in an internal cavity of a subject. The methods include: contacting at least a portion of the interior surface of an opening leading to the internal cavity with an antimicrobial composition; and subsequently at least partially inserting an instrument into the opening. Contacting the internal surface of the opening is more effective than contacting the outer surface of the opening. For example, contacting the internal surface of the urethra is much more effective than merely contacting the outer surface of the urethral opening, which is known as the meatus, since the meatus is typically closed in a normal state and would not allow antimicrobial solutions to enter and kill the microorganism that reside on the interior surface. Thus, with conventional therapy where the microorganisms on the interior surface are not killed they remain viable and when an instrument is inserted they are free to adhere or otherwise move along with the instrument into cavities that are normally essentially sterile. Even if the instrument is precoated with an antimicrobial lubricant most of that lubricant will be wiped off as it is inserted into an opening, such as a urethra, that seals around an instrument, such as a catheter.

The present invention also provides methods of killing or inactivating microorganisms in at least a portion of the urethra of a subject. The methods include contacting at least a portion of the interior surface of the urethra with an antimicrobial composition.

In certain embodiments, the methods of the present invention further include contacting at least a portion of the external surface of the opening (e.g., urethra) with the same or different antimicrobial composition.

In certain methods of the present invention, the antimicrobial composition includes: an effective amount of an antimicrobial component comprising an antiseptic, an antibiotic, or combinations thereof; and a surfactant component distinct from the antimicrobial component, wherein the surfactant component is present in an amount of at least 0.5 percentage by weight (wt-%) and/or the surfactant component comprises an anionic surfactant, zwitterionic surfactant, poloxamer surfactant, amine oxide surfactant, or combinations thereof.

In certain methods of the present invention, the antimicrobial composition includes: an effective amount of an antimicrobial component comprising an antiseptic, an antibiotic, or combinations thereof; a surfactant component distinct from the antimicrobial component; and a vehicle comprising less than 1 wt-% water.

In certain methods of the present invention, the antimicrobial composition includes: an effective amount of an antimicrobial component comprising an antiseptic, an antibiotic, or combinations thereof, a second active agent distinct from the antimicrobial component; and a surfactant component distinct from the antimicrobial component.

In certain methods of the present invention, the antimicrobial composition includes: an effective amount of an antimicrobial component comprising an antiseptic, an antibiotic, or combinations thereof; and at least 0.10 wt-% of an enhancer component comprising an alpha-hydroxy acid, a beta-hydroxy acid, a chelating agent, a (C1-C4)alkyl carboxylic acid, a (C6-C12)aryl carboxylic acid, a (C6-C12) aralkyl carboxylic acid, a (C6-C12)alkaryl carboxylic acid, a phenolic compound, a (C1-C10)alkyl alcohol, an ether glycol, or combinations thereof.

In certain methods of the present invention, the antimicrobial composition includes: an effective amount of an antimicrobial component comprising an antiseptic, an antibiotic, or combinations thereof; an effective amount of an enhancer component comprising a alpha-hydroxy acid, a beta-hydroxy acid, a chelating agent, a (C1-C4)alkyl carboxylic acid, a (C6-C12)aryl carboxylic acid, a (C6-C12) aralkyl carboxylic acid, a (C6-C12)alkaryl carboxylic acid, a phenolic compound, a (C1-C10)alkyl alcohol, an ether glycol, or combinations thereof; and a surfactant component distinct from the antimicrobial component.

In certain methods of the present invention, the antimicrobial composition includes: an effective amount of an antimicrobial component comprising an antiseptic, an antibiotic, or combinations thereof; a hydrophilic vehicle (preferably other than water); and a surfactant component distinct from the antimicrobial component.

In certain methods of the present invention, the antimicrobial composition includes: an effective amount of an antimicrobial component comprising an antiseptic, an antibiotic, or combinations thereof; a surfactant component distinct from the antimicrobial component; and wherein the composition has a viscosity of at least 1,000 Centipoise (cps) at 23° C.

In certain methods of the present invention, the antimicrobial composition includes: an effective amount of an antimicrobial component comprising an antiseptic, an antibiotic, or combinations thereof; a hydrophilic component; and a hydrophobic component; wherein the hydrophobic component or the hydrophilic component forms the greatest portion of the composition by weight.

In certain methods of the present invention, the antimicrobial composition includes an antiseptic. In certain methods of the present invention, the antiseptic includes an antimicrobial lipid, a phenolic antiseptic, a cationic antiseptic, iodine and/or an iodophor, a peroxide antiseptic, an antimicrobial natural oil, or combinations thereof.

In certain methods of the present invention, the antimicrobial component of the composition includes an antimicrobial lipid.

In certain embodiments, the antimicrobial lipid is selected from the group consisting of a (C6-C14)alkyl carboxylic acid, a (C8-C22)mono- or poly-unsaturated carboxylic acid, a fatty acid ester formed from one of the foregoing fatty acids with a hydroxylcarboxylic acid, and combinations thereof. Preferred examples of a fatty acid ester formed from one of the foregoing fatty acids with a hydroxylcarboxylic acid include a (C8-C12)fatty acid ester of a (C2-C8)hydroxycarboxylic acid, a (C8-C22)mono- or poly-unsaturated fatty acid ester of a (C2-C8)hydroxycarboxylic acid.

In certain embodiments, the antimicrobial lipid is selected from the group consisting of a (C7-C14)saturated fatty acid ester of a polyhydric alcohol, a (C8-C22)unsaturated fatty acid ester of a polyhydric alcohol, a (C7-C14)saturated fatty ether of a polyhydric alcohol, a (C8-C22)unsaturated fatty ether of a polyhydric alcohol, a (C7-C14)fatty alcohol ester (preferably a monoester) of a (C2-C8)hydroxycarboxylic acid (preferably a (C8-C12)fatty alcohol ester (preferably a monoester) of a (C2-C8)hydroxycarboxylic acid), a (C8-C22)mono- or poly-unsaturated fatty alcohol ester (preferably a monoester) of a (C2-C8)hydroxycarboxylic acid, an alkoxylated derivative of any of the foregoing having a free hydroxyl group, and combinations thereof; wherein the alkoxylated derivative has less than 5 moles of alkoxide per mole of polyhydric alcohol or hydroxycarboxylic acid; with the proviso that for polyhydric alcohols other than sucrose, the esters comprise monoesters and the ethers comprise monoethers, and for sucrose the esters comprise monoesters, diesters, or combinations thereof, and the ethers comprise monoethers.

In certain embodiments, the antimicrobial lipid is selected from the group consisting of a (C8-C12)saturated fatty acid ester of a polyhydric alcohol, a (C12-C22)unsaturated fatty acid ester of a polyhydric alcohol, a (C8-C12)saturated fatty ether of a polyhydric alcohol, a (C12-C22)unsaturated fatty ether of a polyhydric alcohol), an alkoxylated derivative of any of the foregoing, and combinations thereof; wherein the alkoxylated derivative has less than 5 moles of alkoxide per mole of polyhydric alcohol; with the proviso that for polyhydric alcohols other than sucrose, the esters comprise monoesters and the ethers comprise monoethers, and for sucrose the esters comprise monoesters, diesters, or combinations thereof, and the ethers comprise monoethers.

In certain embodiments, the antimicrobial component includes a phenolic antiseptic. In certain embodiments, the phenolic antiseptic is selected from the group consisting of diphenyl ethers, phenolics, bisphenolics, resorcinols, anilides, and combinations thereof. In certain embodiments, the phenolic antiseptic comprises triclosan.

In certain embodiments, the antimicrobial component includes a cationic antiseptic. In certain embodiments, the cationic antiseptic is selected from the group consisting of biguanides, bisbiguanides, polymeric biguanides, polymeric quaternary ammonium compounds, silver and its complexes, small molecule quaternary ammonium compounds, and combinations thereof.

In certain embodiments, the antimicrobial component includes iodine and/or an iodophor. In certain embodiments, the iodophor is povidone-iodine.

In certain embodiments, the antimicrobial component does not include iodine or chlorhexidine. For example, when the internal cavity comprises a nasal passage, vagina, or oral cavity, the antimicrobial component does not include iodine or chlorhexidine. As another example, when the internal cavity comprises a nasal passage or vagina, the antimicrobial component does not include iodine.

In certain embodiments, the antimicrobial component includes a peroxide antiseptic.

In certain embodiments, the antimicrobial component includes an antimicrobial natural oil.

In certain embodiments, the antimicrobial composition comprises a water-in-oil emulsion.

In certain embodiments, the total concentration of the surfactant component to the total concentration of antimicrobial component is within a range of 5:1 to 1:100, on a weight basis. In certain embodiments, the surfactant component includes a sulfonate surfactant, a sulfate surfactant, a phosphonate surfactant, a phosphate surfactant, a poloxamer surfactant, a cationic surfactant, or mixtures thereof. In certain embodiments, the surfactant component is present in an amount at least 0.5 wt-%.

In certain embodiments, the second active agent includes a local anesthetic, analgesic, anti-inflammatory agent, an antipyretic, or combinations thereof.

In certain embodiments, the enhancer component includes an alpha-hydroxy acid and/or a chelating agent. In certain embodiments, the total concentration of the enhancer component relative to the total concentration of antimicrobial component is within a range of 10:1 to 1:300, on a weight basis.

In certain embodiments, the vehicle includes a dispersible hydrophilic component.

In certain embodiments, the viscosity of the antimicrobial composition is at least 50,000 cps at 23° C.

In certain embodiments, the hydrophilic component is present in an amount of at least 4% by weight. In certain embodiments, the hydrophilic component includes a glycol, a lower alcohol ether, a short chain ester, or combinations thereof, wherein the hydrophilic component is soluble in water in an amount of at least 20 wt-% at 23° C.

In certain embodiments, the hydrophobic component has a solubility in water of less than 5 wt-% at 23° C.

In certain embodiments, the antimicrobial composition achieves at least 4 log reduction in test bacteria in 10 minutes when evaluated by the Antimicrobial Efficacy Test.

In certain embodiments, the internal cavity includes the bladder, abdominal cavity, peritoneal cavity, trachea, lung, upper sinuses, or stomach. In certain embodiments, the internal cavity is the bladder.

In certain embodiments, the opening to the internal surface includes at least a portion of the internal surface of the urethra, cervical opening, nasal passages, oral cavity, or a surgical incision/puncture site. In certain embodiments, the opening to the internal surface includes at least a portion of the internal surface of the urethra.

In certain embodiments, the instrument is selected from the group consisting of nasal gastric tubes, tracheotomy tubes, urinary catheters, peritoneal dialysis tubes, ventilator tubes, endotracheal tubes, and surgical instruments.

In certain embodiments, the infection is a urinary tract infection. In certain embodiments, the urinary tract infection is an infection of the bladder.

In certain embodiments, the microbial organism includes bacteria and the antimicrobial composition is used in an amount effective to kill one or more bacteria.

In certain embodiments, the bacteria include *Staphylococcus* spp., *Streptococcus* spp., *Escherichia* spp., *Enterococcus* spp., *Pseudamonas* spp., or combinations thereof.

In certain embodiments, the microbial organism includes one or more fungi and the antimicrobial composition is used in an amount effective to kill one or more fungi.

In certain embodiments, residual antimicrobial efficacy is provided to the surface to which the antimicrobial composition is applied.

In certain embodiments, wherein the instrument is treated with the same or different antimicrobial composition prior to the inserting step. In certain embodiments, the instrument provides antimicrobial activity for an extended period of time.

In certain embodiments, the pH of the composition is less than 7.

Definitions

The following terms are used herein according to the following definitions.

"Effective amount" means the amount of the antimicrobial component and/or the enhancer component when in a composition, as a whole, provides an antimicrobial (including, for example, antiviral, antibacterial, or antifungal) activity that reduces, prevents, or eliminates one or more species of microbes such that an acceptable level of the microbe results. Typically, this is at least a 0.5 log reduction using the Urethra Antimicrobial Test described herein, and is desirably at least a 1 log reduction, more preferably at least a 2 log reduction, and most desirably reduces the bacteria to a non-detectable level after a 30 minute contact time with the antimicrobial composition, preferably after only a 10 minute contact time with the antimicrobial composition, and most preferably after only a 5 minute min contact time with the antimicrobial composition. It should be understood that in the compositions described herein, the concentrations or amounts of the components, when considered separately, may not kill to an acceptable level, or may not kill as broad a spectrum of undesired microorganisms, or may not kill as fast; however, when used together such components provide an enhanced (preferably synergistic) antimicrobial activity (as compared to the same components used alone under the same conditions).

It should be understood that (unless otherwise specified) the listed concentrations of all components are for "ready to use" or "as used" compositions. The compositions can be in a concentrated form. That is, certain embodiments of the compositions can be in the form of concentrates that would be diluted by the user with an appropriate vehicle; however, this is typically not convenient for the present application.

"Hydrophilic" refers to a material that will dissolve or disperse in water (or other aqueous solution as specified) at a temperature of 23° C. in an amount of at least 7% by weight, preferably at least 10% by weight, more preferably at least 20% by weight, even more preferably at least 25% by weight, even more preferably at least 30% by weight, and most preferably at least 40% by weight, based on the total weight of the hydrophilic material and the water. The component is considered dissolved if after thoroughly mixing the compound with water at 60° C. for at least 4 hours and allowing this to cool to 23-25° C. for 24 hours, and then again mixing the composition thoroughly it appears as a uniform clear solution without visible cloudiness, phase separation, or precipitate in a jar having a path length of 4 cm. Typically, when placed in 1×1 cm cell, the sample containing a hydrophilic material in water exhibits greater than, or equal to, 70% transmission measured in a suitable spectrophotometer at a wavelength of 655 nm. This dissolution test is done at the concentration of interest, e.g., at 7-40% by weight. Water dispersible hydrophilic materials disperse in water to form uniform cloudy dispersions after vigorous shaking of a 5% by weight mixture of the hydrophilic component in water above the melting point of the component followed by cooling to room temperature for 4 hours, or preferably placing in a Warning Blender half full for 3 minutes and allowing any foam to settle to form a uniform dispersion without visible phase separation (creaming or settling) after standing for 60 minutes. Preferred hydrophilic components are water-soluble. The hydrophilic component can be water.

"Hydrophobic" or "water-insoluble" refers to a material that will not significantly dissolve in water at 23° C. This means that less than 5% by weight, preferably less than 1% by weight, more preferably less than 0.5% by weight, and even more preferably less than 0.1% by weight, based on the total weight of the hydrophobic material and the water, will dissolve. Solubility can be determined by thoroughly mixing the compound with water at the appropriate concentration at 23° C. for at least 24 hours (or at elevated temperature if that is necessary to dissolve the compound), allowing this to sit at 23-25° C. for 24 hours, and observing the sample. In a glass jar with a 4-cm path length the sample should have evidence of a second phase, which can be liquid or solid and may be separated on the top, bottom, or distributed throughout the sample. For crystalline compounds care should be taken to avoid producing a supersaturated solution. The components should be mixed and observed. Cloudiness or presence of a visible precipitate or separate phase indicates that the solubility limit has been exceeded. Typically, when placed in 1×1 cm cell the sample the composition containing the hydrophobic compound in water has less than 70% transmission measured in a suitable spectrophotometer at a wavelength of 655 nm. For solubility determinations less than that which can be observed with the naked eye the solubility is determined using radiolabeled compounds as described under "Conventional Solubility Estimations in Solubility of Long-Chain Fatty Acids in Phosphate Buffer at pH 7.4," Henrik Vorum, et al. in *Biochimica et. Biophysica Acta*, 1126, 135-142 (1992).

"Stable" means physically stable or chemically stable, which are both defined in greater detail below.

"Enhancer" means a component that enhances the effectiveness of the antimicrobial component such that when the composition less the antimicrobial component and the composition less the enhancer component are used separately, they do not provide the same level of antimicrobial activity as the composition as a whole. For example, an enhancer component in the absence of the antimicrobial component may not provide any appreciable antimicrobial activity. The enhancing effect can be with respect to the level of kill, the speed of kill, and/or the spectrum of microorganisms killed, and may not be seen for all microorganisms. In fact, an enhanced level of kill is most often seen in Gram negative bacteria such as *Escherichia coli*. An enhancer may be a synergist such that when combined with the remainder of the composition, the composition as a whole displays an activity that is greater than the sum of the activity of the composition less the enhancer component and the composition less the antimicrobial component.

"Microorganism" or "microbe" or "microorganism" refers to bacteria, yeast, mold, fungi, protozoa, mycoplasma, as well as viruses (including lipid enveloped RNA and DNA viruses).

"Antibiotic" means an organic chemical produced by microorganisms that has the ability in dilute concentrations to destroy or inhibit microorganisms and is used to treat infectious disease. This may also encompass semi-synthetic compounds that are chemical derivatives of the compound produced by microorganisms or synthetic compounds that act on very specific biochemical pathways necessary for the cell's survival.

"Antiseptic" means a chemical agent that kills pathogenic and non-pathogenic microorganisms. Preferred antiseptics exhibit at least a 4 log reduction of both *P. aeruginosa* and *S. aureus* in 60 minutes from an initial inoculum of $1-3 \times 10^7$ CFU/mL when tested in Mueller Hinton broth at 35° C. at a concentration of 0.25 wt-% in a Rate of Kill assay using an appropriate neutralizer as described in "The Antimicrobial Activity in vitro of chlorhexidine, a mixture of isothiazolinones (Kathon C G) and cetyl trimethyl ammonium bromide (CTAB)," G. Nicoletti et al., *Journal of Hospital Infection*, 23, 87-111 (1993). Antiseptics generally interfere more broadly with the cellular metabolism and/or the cell envelope. Antiseptics are sometimes referred to as disinfectants, especially when used to treat hard surfaces.

"Mucous membranes," "mucosal membranes," and "mucosal tissue" are used interchangeably and refer to the surfaces of the nasal (including anterior nares, nasoparangyl cavity, etc.), vaginal cavities (including the meatus and urethra), and other similar tissues. Examples include mucosal membranes such as nasal, rectal, urethral, ureteral, vaginal, cervical, and uterine mucosal membranes.

"Antimicrobial lipid" means an antibiotic compound having at least one alkyl or alkylene group having at least 6 carbon atoms, more preferably at least 7 atoms, and even more preferably 8 atoms and preferably having a solubility in water of no greater than 1.0 gram per 100 grams (1.0 g/100 g) deionized water. Preferred antimicrobial lipids have a solubility in water of no greater than 0.5 g/100 g deionized water, more preferably, no greater than 0.25 g/100 g deionized water, and even more preferably, no greater than 0.10 g/100 g deionized water. Solubilities are determined using radiolabeled compounds as described under "Conventional Solubility Estimations" in Solubility of Long-Chain Fatty Acids in Phosphate Buffer at pH 7.4, Henrik Vorum et al., in *Biochimica et. Biophysica Acta.*, 1126, 135-142 (1992). Preferred antimicrobial lipids have a solubility in deionized water of at least 100 micrograms (μg) per 100 grams deionized water, more preferably, at least 500 μg/100 g deionized water, and even more preferably, at least 1000 μg/100 g deionized water. The antimicrobial lipids preferably have a hydrophile/lipophile balance (HLB) of at most 6.2, more preferably at most 5.8, and even more preferably at most 5.5. The antimicrobial lipids preferably have an HLB of at least 3, preferably at least 3.2, and even more preferably at least 3.4.

"Fatty" as used herein refers to a straight or branched chain alkyl or alkylene moiety having at least 6 (odd or even number) carbon atoms, unless otherwise specified.

"Affliction" means a condition to a body resulting from sickness, disease, injury, bacterial colonization, etc.

"Urinary tract infection" (UTI) refers to a condition that results in an elevated level of bacteria in the urine with or without clinical signs of an infection such as fever and/or pain and thus may encompass the term "bacteriuria." The term is meant to encompass both catheter associated and non-catheter associated UTI. It can also be used to refer to infections of the bladder, i.e., bladder infections. Of particular interest to this invention, however, is the prevention and treatment of catheter associated urinary tract infection (CAUTI). While many articles in the literature define CAUTI as having >100,000 colony forming units (CFU)/mL of voided urine, for the purposes of this invention, any level of bacteria in the urine (even as low as 100 CFU/mL or lower) can be a concern for patient welfare.

"Treat" or "treatment" means to improve the condition of a subject relative to the affliction, typically in terms of clinical symptoms of the condition.

"Decolonization" refers to a reduction in the number of microorganisms (e.g., bacteria, virus, and fungi) present in or on tissue that do not necessarily cause immediate clinical symptoms. Examples of decolonization include, but are not limited to, decolonization of internal cavities, such as the urethra. Ordinarily, fewer microorganisms are present in colonized tissue than in infected tissue. When the tissue is completely decolonized the microorganisms have been "eradicated" and are non-detectable.

An "instrument" means any medical article intended to perform a task on a subject, and most often includes tubes, catheters, surgical instruments, and the like.

"Subject" and "patient" includes humans, sheep, horses, cattle, pigs, dogs, cats, rats, mice, or other mammal.

The terms "comprises" and variations thereof do not have a limiting meaning where these terms appear in the description and claims.

As used herein, "a," "an," "the," "at least one," and "one or more" are used interchangeably. The term "and/or" means one or all of the listed elements (e.g., preventing and/or treating an infection means preventing, treating, or both treating and preventing further infections).

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Compositions described herein provide effective topical antimicrobial activity and are accordingly useful in the local treatment and/or prevention of conditions that are caused, or aggravated by, microorganisms (including viruses, bacteria, fungi, mycoplasma, and protozoa) on various mammalian tissues, particularly the urethra, vaginal tissue, anterior nares, upper nares, and lower sinuses.

More particularly, the compositions described herein are useful for the decolonization of the internal surface of an opening, which can be an orifice, a channel, a canal (e.g., a urethra) that leads to an internal body space (e.g., an internal cavity such as the bladder) that is prone to infection, prior to insertion of an instrument (e.g., a medical device such as a catheter).

Examples of such openings, the cavities to which the openings lead, and the typical instruments that are used in such openings for access to the cavities are as follows:

| Opening (e.g., Canal) | Body Cavity | Instrument |
| --- | --- | --- |
| Urethra | Bladder | Catheter or surgical instrument |
| Oral cavity | Lungs | Endotracheal tube |
| Oral cavity | Stomach | Gastric tube |
| Nasal passages | Upper sinuses | NG tubes |
| Surgical puncture | Peritoneal cavity | Dialysis catheter |
| Surgical incision | Lungs | Trachea tubes |

Compositions described herein can provide effective reduction, prevention, or elimination of microbes, particularly bacteria, yeast, and fungi, and in some cases viruses on the tissue to which it is applied, and thereby help to prevent or prolong the time to infection of the internal cavities (e.g., bladder, abdominal cavity, peritoneal cavity, trachea, lung, stomach, or upper sinuses). Since the contaminating microbes may be of a relatively wide variety, preferred compositions described herein have a broad spectrum of activity.

For example, the present invention provides methods of delaying the onset of an infection or preventing an infection caused by a microbial organism in an internal cavity of a subject upon contacting at least a portion of the interior surface of an opening into the internal cavity with an antimicrobial composition; and subsequently at least partially inserting an instrument into the opening. Other methods of the present invention include killing or inactivating microorganisms in at least a portion of the urethra of a subject by contacting at least a portion of the interior surface of the urethra with an antimicrobial composition; and subsequently at least partially inserting an instrument into the urethra.

Preferably, contacting at least a portion of the interior surface of an opening into the internal cavity with an antimicrobial composition includes placing the composition on at least 1 centimeter (cm) (depth or length) of the interior surface of the opening (e.g., canal), more preferably at least 2 cm, even more preferably at least 3 cm, even more preferably at least 4 cm, and most preferably for the entire length of the interior surface (e.g., the entire length of the canal). Preferably, contacting at least a portion of the interior surface of an opening into the internal cavity with an antimicrobial composition includes allowing the composition to reside on the internal surface for at least 10 seconds (sec), more preferably at least 30 sec, and even more preferably at least 1 minute prior to inserting the instrument into the opening. Preferably, contacting at least a portion of the interior surface of an opening into the internal cavity with an antimicrobial composition includes allowing the composition to reside on the internal surface for no greater than 30 minutes (min), more preferably for no greater than 20 min, even more preferably for no more than 10 min, and even more preferably for no more than 5 min prior to inserting the instrument into the opening. Preferably the interior surface is contacted by filling the opening (e.g., canal) with the antimicrobial composition.

Additionally, the antimicrobial composition may be placed on the exterior of the instrument, followed by insertion of the instrument. The antimicrobial may act on the microorganisms and optionally also diffuse into the outer layers of the device rendering the surface of the device active against microorganisms.

Herein, to "kill or inactivate" means to render the microorganism ineffective by killing them (e.g., bacteria and fungi) or otherwise rendering them inactive (e.g., bacteria and viruses). The present invention provides methods for killing bacteria such as *Staphylococcus* spp., *Streptococcus* spp., *Escherichia* spp., *Enterococcus* spp., *Pseudamonas* spp., *Gardnerella* sp., *Haemophilus* sp., *Corynebacterium* sp. bacteria, *Candida* sp. fungi, and combinations thereof, and more particularly *Staphylococcus aureus* (including antibiotic resistant strains such as methicillin resistant *Staphylococcus aureus*), *Staphylococcus epidermidis*, *Escherichia coli* (*E. coli*), *Pseudomonas aeruginosa* (*Pseudomonas* ae.), *Streptococcus pyogenes, Candida albicans*, and combinations thereof which often are on or in the skin or mucosal tissue as well as on the interior surface of various anatomical canals or surrounding the exterior opening (e.g., urethra) of a subject. The method includes contacting the microorganism with an antimicrobial composition of the present invention in an amount effective to kill one or more microorganisms (e.g., bacteria and fungi) or inactivate one or more microorganisms (e.g., viruses, particularly herpes virus).

Significantly, certain compositions described herein have a very low potential for generating microbial resistance. Thus, such compositions can be applied multiple times such as whenever a catheter is inserted as well as to the exterior tissue around the catheter over one or more days to treat topical infections or to eradicate unwanted bacteria (such as *E. coli, Streptococcus* sp., *Staphylococcus* sp., and the like). Furthermore, compositions described herein can be used for multiple treatment regimens on the same patient without the fear of generating antimicrobial resistance. This can be particularly important for chronically ill patients who are in need of long term catheterization and/or catheterization prior to surgery.

Also, preferred compositions described herein have a generally low irritation on the tissue to which it is applied. Also, certain preferred compositions described herein are substantive for relatively long periods of time to ensure adequate efficacy and serve as a lubricant to facilitate insertion of the instrument.

The methods of the present invention use antimicrobial (including, e.g., antiviral, antibacterial, and antifungal) compositions. These compositions include one or more antimicrobial components. In certain embodiments, the compositions also include one or more enhancers. Certain compositions also include one or more surfactants, one or more hydrophilic compounds, and/or one or more hydrophobic compounds. In certain embodiments, the hydrophobic component can be the same as the antimicrobial component, for example, when the antimicrobial component is an antimicrobial lipid. Some compositions are anhydrous or have very low water content (preferably, no greater than 10 wt-% of the total composition, and more preferably, no greater than 5 wt-% of the total composition). This may help chemical and/or physical stability of these compositions.

The antimicrobial component(s) are preferably selected to ensure rapid broad spectrum activity without irritation, stinging, or burning. In certain embodiments, the antimicrobial component preferably has a solubility in water of at least 100 micrograms (µg) per 100 grams (g) deionized water and at most 1 g/100 g deionized water. In other embodiments the antimicrobial component is quite soluble in water having a solubility in excess of 1 g/100 g deionized water.

Preferably, the antimicrobial component is present in an amount of at least 0.05 wt-%, and more preferably at least 0.1 wt-%. Unless otherwise specified, all weight percents are based on the total weight of a "ready to use" or "as used" composition.

The antimicrobial components can be antiseptics, antibiotics, or combinations thereof. Preferably, one or more antiseptics are used.

Herein, antiseptics are distinct from preservatives. Preservatives generally are used at very low levels since the purpose of these preservatives is to prevent bacterial growth in the composition, not to kill microbes on or in the tissue. They are typically added at levels of much less than 1% and most often less than 0.1% by weight. Typical preservatives include parabens, formaldehyde donors, 2-phenoxyethanol, benzyl alcohol, quaternary ammonium surfactants such as benzalkonium chloride, and the like. When used on colonized or infected tissue at the industry standard preservative concentrations they would not achieve adequate antimicrobial activity.

Suitable antiseptics include, for example: antimicrobial lipids; phenolic antiseptics; cationic antiseptics; iodine and/or iodophors; peroxide antiseptics; antimicrobial natural oils; or combinations thereof.

Certain compositions further include an enhancer component (i.e., an enhancer). Other components that can be included as well are surfactants, hydrophilic components, and hydrophobic components. Compositions with hydrophobic components are typically used on mammalian tissues where visualization is not anticipated. Such components could interfere with vision when using fiber optic visualization techniques such as scopes inserted into the urethra or other treated interior canal.

Importantly, compositions described herein are capable of destroying microorganisms on or in mammalian tissue. Therefore, concentrations of components employed are generally greater than those that have been used to simply preserve certain topically applied compositions, i.e., prevent the growth of microorganism in topical compositions for purposes other than antisepsis. Depending on the application, many of these compounds at these concentrations can be irritating if delivered in simple aqueous or water-soluble hydrophilic vehicle formulations. Many of the compositions described herein incorporate a substantial amount of a lipophilic or hydrophobic phase or water dispersible phase. The lipophilic phase is comprised of one or more water insoluble components. If delivered in a lipophilic phase, the irritation can be significantly reduced. The incorporation of the lipophilic phase may significantly reduce the irritation potential of the present compositions.

Preferred lipophilic phase components have a solubility in water of less than 0.5% by weight and often less than 0.1% by weight. In addition, the antimicrobial lipid is preferably present at a concentration approaching or preferably exceeding the solubility limit of the lipophilic phase. Despite the presence of the hydrophobic phase, compositions described herein exhibit very effective and rapid antimicrobial activity. Preferred formulations incorporating lipophilic components can be easily dispersed in saline or water at 37° C. in order to allow the composition to be easily flushed from the tissue if irritation were to occur or if it became necessary to perform a scope procedure.

Importantly, certain compositions described herein have sufficient viscosity to lubricate the instrument and to prevent it being immediately expelled from a collapsible canal or other opening such as the urethra. The relatively high viscosity of certain compositions described herein also reduces migration that can be associated with other compositions, thus reducing irritation and mess. In addition, antimicrobial compositions that include hydrophilic components such as polyols (e.g., glycerin and polyethylene glycols) that themselves have little or no antimicrobial activity can considerably enhance the antimicrobial activity of the compositions.

Preferred compositions wet and optionally adhere well to bodily tissues (i.e., mammalian tissues such as mucosal tissue) and thus are very effective topically. These compositions are said to be "substantive." Similarly, preferred compositions also wet the instrument well to provide lubrication and prevent tissue damage. Thus, the present invention provides uses for the compositions. Particularly preferred methods involve topical application, particularly to mucosal tissues (i.e., mucous membranes including the esophagus, anterior nares, oral cavity, and the urethra), prior to insertion of an instrument such as a catheter or nasal gastric (NG) tube. Herein, such tissues are preferred examples of mammalian tissues.

For certain applications in which limited antimicrobial activity is desired, compositions containing antiseptics with limited spectrum of activity may be used. For example, in certain situations it may be desirable to kill or inactivate only one type or class of microorganism (e.g., Gram positive or Gram negative bacteria) as opposed to all the microorganisms present. In such situations, compositions described herein that contain an antimicrobial component without an enhancer component may be suitable.

For example, some of the antimicrobial components in the absence of an enhancer are only effective against Gram positive organisms. In most applications, broad spectrum antimicrobial activity is desired. Compositions containing a broad spectrum antiseptic such as iodine or an iodophor, hydrogen peroxide, chlorhexidine salts, polyhexamethylene biguanide, small molecule quaternary amines such as benzethonium chloride, methylbenzethonium chloride, benzalkonium chloride and octenidine, antimicrobial metals such as silver, triclosan, as well as combinations thereof, optionally with an enhancer component are used in such situations.

Compositions described herein can be used to provide effective topical antimicrobial activity and thereby treat and/or prevent a wide variety of afflications. For example, they can be used in the treatment and/or prevention of afflictions that are caused, or aggravated by, microorganisms (e.g., Gram positive bacteria, Gram negative bacteria, fungi, protozoa, mycoplasma, yeast, viruses, and even lipid-enveloped viruses) entering a mammalian cavity or organ such as the bladder, upper sinuses, or peritoneal cavity.

Particularly relevant organisms that cause or aggravate such afflications include *Staphylococcus* spp., *Streptococcus* spp., *Pseudomonas* spp., *Enterococcus* spp., *Gardnerella* spp., *Corynebacterium* spp., *Bacteroides* spp., *Mobiluncus* spp., *Peptostreptococcus* spp., and *Esherichia* spp., bacteria, as well as herpes virus, *Aspergillus* spp., *Fusarium* spp., *Candida* spp., as well as combinations thereof. Particularly virulent organisms include *Staphylococcus aureus* (including resistant strains such as *Methicillin Resistant Staphylococcus Aureus* (MRSA), *Staphylococcus epidermidis*, *Streptococcus pneumoniae*, *Enterococcus faecalis*, *Vancomycin Resistant Enterococcus* (VRE), *Pseudomonas auerginosa*, *Escherichia coli*, *Aspergillus niger*, *Aspergillus fumigatus*, *Aspergillus clavatus*, *Fusarium solani*, *Fusarium oxysporum*, *Fusarium chlamydosporum*, *Candida albicans*, *Candida glabrata*, *Candida krusei*, and combinations thereof.

Compositions described herein can be used for the prevention and/or treatment of one or more microorganism-caused infections or other afflictions. In particular, compositions described herein can be used for preventing and/or treating one or more of the following: urinary tract infections of the bladder and urethra; internal and external bacterial colonization of the urethra and meatus; infections of the sinuses resulting from or aggrevated by insertion of an NG tube; peritoneal infections resulting from or aggrevated by insertion of a dialysis tube; fungal and bacterial infections of the vagina or rectum; vaginal yeast infections; bacterial rhinitis; colonization by *Staphylococcus aureus* in the anterior nares and lower sinuses; mucositis (i.e., inflammation as opposed to infection of a mucous membrane typically induced by non-invasive fungus). In sum, compositions described herein can be used for preventing and/or treating a wide variety of topical afflictions caused by microbial colonization and/or infection (e.g., yeast, viral, bacterial infections). In addition, the compositions of this invention are useful for delaying infections associated with long term device use such as catheter associated urinary tract infections.

It should be understood that compositions described herein can be used in situations in which there are no clinical indications of an affliction. For example, compositions described herein can be used in methods of decolonizing at least a portion of the urethra (and meatus), nasal cavities (i.e., space behind the vestibule of the nose), anterior nares (i.e., the opening in the nose to the nasal cavities, also referred to as the external nares), and/or nasopharynx (i.e., the portion of the pharynx, i.e., throat, that lies above the point of food entry into the pharynx) of a subject of microorganisms. These compositions may also be useful as oral antiseptics for decolonizing the oral cavity prior to insertion of ventilator tubing and/or for oral decontamination while a patient is on a ventilator.

Decolonization methods using compositions described herein are particularly useful in immunocompromised patients (including oncology patients, diabetics, HIV patients, transplant patients, intensive care patients, and the like), particularly for fungi such as *Aspergillus* spp. and *Fusarium* spp.

Those of ordinary skill in the art will readily determine when a composition of the present invention provides antimicrobial activity using assay and bacterial screening methods well known in the art. One readily performed assay involves exposing selected known or readily available viable microorganism strains, such as *Enterococcus* spp., *Aspergillus* spp., *Escherichia* spp., *Staphylococcus* spp., *Streptococcus* spp., *Pseudomonas* spp., or *Salmonella* spp., to a test composition at a predetermined bacterial burden level in a culture media at an appropriate temperature. For the preferred compositions described herein this is most conveniently done by the Antimicrobial Kill Rate Test described in the Examples Section.

Briefly, as discussed in the Antimicrobial Efficacy Test, after a sufficient contact time, an aliquot of a sample containing the exposed bacteria is collected, diluted, and plated out on agar. The plated sample of bacteria is incubated for forty-eight hours and the number of viable bacterial colonies growing on the plate is counted. Once colonies have been counted the reduction in the number of bacteria caused by the test composition is readily determined. Bacterial reduction is generally reported as $\log_{10}$ reduction determined by the difference between the $\log_{10}$ of the initial inoculum count and the $\log_{10}$ of the inoculum count after exposure. Preferred compositions described herein have an average of at least a 3 log reduction and more preferably at least a 4 log reduction in test bacteria in 10 minutes, and preferably in as little as 2.5 minutes.

Many of the preferred compositions were tested as described in the Examples Section for antimicrobial activity against MRSA (Gram positive, ATCC Number 16266), *E. coli* (Gram negative, ATCC Number 11229), and *Pseudomonas aeruginosa* (Gram negative, ATCC Number 15442). In general, the *Pseudomonas aeruginosa* is often the most difficult to kill. Preferred compositions described herein also exhibit very rapid antimicrobial activity. As shown in the Examples Section, preferred formulations are able to achieve an average log reduction of at least 3 log and preferably at least 4 log against these three organisms after a 10 minute exposure and preferably after a 5 minute exposure. More preferred compositions are able to achieve an average log reduction of at least 5 log, and even more preferably an average log reduction of at least 6 log, against these three organisms after a 10 minute exposure (and more preferably after 1 minute of exposure time) and preferably after a 5 minute exposure.

For residual antimicrobial efficacy, compositions described herein preferably maintain an average log reduction of at least 1 log, more preferably at least 1.5 log, and even more preferably at least 2 log, for at least 0.5 hour, more preferably at least 1 hour, and even more preferably at least 3 hours after application to an affected site. This is most conveniently tested by applying the composition on the forearm of a subject. To test this, a composition was applied to the forearm of a subject as a uniform wet coating in an amount of approximately 4 milligrams per square centimeter (mg/cm$^2$) to the forearm of a healthy subject and allowed to thoroughly dry (typically a minimum of 10 minutes) over an area of approximately 5×5 cm. The dried composition was gently washed with 23° C. normal saline (0.9% by weight sodium chloride). The saline washed site was exposed to a known quantity of bacteria in an innoculum of 10$^6$ bacteria/mL (typically *Staphylococcus epidermidis* or *E. coli*) for 30 minutes. The bacteria were recovered and treated with an effective neutralizer and incubated to quantify the bacteria remaining. Particularly preferred compositions retain at least 1 log reduction, and preferably at least 2 log reduction, of bacteria after a gentle rinse with 500 mL saline poured over the site by placing the saline container as close to the site as possible so as to not have the saline fall onto the site.

Significantly, certain embodiments of the present invention have a very low potential for generating microbial resistance. For example, preferred compositions described herein have an increase in the ratio of final to initial MIC levels (i.e., minimum inhibitory concentration) of less than 16, more preferably less than 8, and even more preferably less than 4. Such an emergence of resistance assay should be carried out such that the microorganisms are subjected initially to sub MIC levels (e.g., ½ the MIC) of antimicrobial lipid and after 24 hours the microorganisms passed into broth containing twice the concentration of antimicrobial lipid. This is repeated for 8 days and each day microorganisms are removed to determine the new MIC. Thus, such compositions can be applied multiple times over one or more days to treat topical infections or to eradicate unwanted bacteria (such as nasal colonization of *Staphylococcus aureus*).

Preferred compositions described herein contain an effective amount of antimicrobial component to rapidly kill or inactivate microorganisms on mucosal tissue and mucosal membranes. This is evaluated using the Urethra Antimicrobial Test Method described herein. In certain embodiments, essentially all the microorganisms are eradicated or inactivated within 10 minutes, preferably within 5 minutes, more preferably within 2 minutes, and even more preferably within 1 minute, using a single dose according to the test method.

Preferred compositions described herein have a generally low irritation level for skin and mucosal membranes (including the anterior nares, nasal cavities, nasopharangyl cavity, oral cavity, vagina, and urethra). For example, certain preferred compositions described herein are no more irritating than KY jelly lubricant available from Personal Products Company, Div. of McNeil-PPC, Inc., Skillman, N.J.

Preferred compositions described herein are substantive for relatively long periods of time to ensure adequate efficacy. For example, certain compositions described herein remain at the site of application with antimicrobial activity for at least 4 hours and more preferably at least 8 hours.

Preferred compositions described herein are physically stable. As defined herein "physically stable" compositions are those that do not significantly change due to substantial precipitation, crystallization, phase separation, and the like, from their original condition during storage at 23° C. for at least 3 months, preferably for at least 6 months, and more preferably for at least 2 years. Particularly preferred compositions are physically stable if a 10-milliliter (10-mL) sample of the composition when placed in a 15-mL conical-shaped graduated plastic centrifuge tube (Corning) and centrifuged at 500×g and preferably at 1000×g and most preferably at 2000×g have no visible phase separation in the bottom or top of the tube. Some of the compositions may be thickened using components which crystallize such as polyethylene glycols, petrolatum, microcrystalline wax, certain emulsifiers, and the like. These compositions are only presumed to be "unstable" if macroscopic phase separation occurs.

Note that the compositions are preferably free of air so that when applied to the tissue all of the tissue surfaces are adequately covered. Alternatively, foams may be used, however, these may require some tissue manipulation to ensure proper coverage.

Preferred compositions described herein exhibit good chemical stability. This can be especially a concern with some of the antimicrobial components. For example, with iodine containing compositions conversion to iodide may occur. This can be reduced or eliminated as a concern by buffering the pH to less than 5 and preferably less than 4.5. The pH of any of the antimicrobial compositions is preferably greater than 2.5 and preferably greater than 3 to in order to avoid tissue irritation.

Chlorhexidine compositions should be buffered to between 5 and 8. Preferably for vaginal and urethral applications the pH is kept less than 7 to mimic the natural tissue and avoid invasion by abnormal microbial flora. Compositions comprising phenolic antiseptics such as triclosan and PCMX, chlorhexidine, petrolatum and other light sensitive components additionally must be protected from ultraviolet (UV) light to avoid chemical breakdown. This can be accomplished through the use of UV absorbers in the packaging or by packing the composition in a UV impermeable opaque package. Antimicrobial fatty acid esters and fatty alcohol esters of hydroxy acids, and fatty acid esters of hydroxyacids can often undergo transesterification and hydrolysis. This can be prevented by formulating without potentially reactive excipients (e.g., those with free OH or COOH group) or by formulating with an excipients that if reaction occurred would yield the same compound (e.g., formulation of a glycerol monolaurate formulation with glycerin). Hydrolysis is most easily prevented by formulating in anhydrous or nearly anhydrous conditions. Althernatively, the pH can be kept as close to neutral as possible.

Preferred compositions retain at least 85%, more preferably at least 90%, even more preferably at least 92%, and even more preferably at least 95%, of the antimicrobial component after aging for 4 weeks at 40° C. (an average of three samples) beyond the initial 5-day equilibration period at 23° C. The most preferred compositions retain an average of at least 97% of the antimicrobial component after aging for 4 weeks at 40° C. in a sealed container beyond the initial 5-day equilibration period at 23° C. The percent retention is understood to mean the weight percent of antimicrobial component retained. This is determined by comparing the amount remaining in a sample aged (i.e., aged beyond the initial 5-day equilibration period) in a sealed container that does not cause degradation, to the actual measured level in an identically prepared sample (preferably from the same batch) and allowed to sit at 23° C. for five days. The level of antimicrobial component is preferably determined using gas chromatography or other suitable sensitive analytical technique.

Generally, the compositions of this invention may be in one of the following forms:

A hydrophobic ointment: The compositions are formulated with a hydrophobic base (e.g., petrolatum, thickened or gelled water insoluble oils, and the like) and optionally having a minor amount of a water soluble phase.

An oil-in-water emulsion: The compositions may be formulations in which the antimicrobial component is emulsified into an emulsion comprising a discrete phase of a hydrophobic component and a continuous aqueous phase that includes water and optionally one or more polar hydrophilic carrier(s) as well as salts, surfactants, emulsifiers, and other components. These emulsions may include water-soluble or water-swellable polymers as well as one or more emulsifier(s) that help to stabilize the emulsion. These emulsions generally have higher conductivity values, as described in International Publication WO 2003/028767). The antimicrobial component(s) may be in one or both phases depending on the solubility.

A water-in-oil emulsion: The compositions may be formulations in which the antimicrobial component is incorporated into an emulsion that includes a continuous phase of a hydrophobic component and an aqueous phase that includes water and optionally one or more polar hydrophilic carrier(s) as well as salts or other components. These emulsions may include oil-soluble or oil-swellable polymers as well as one or more emulsifier(s) that help to stabilize the emulsion. The antimicrobial component(s) may be in one or both phases depending on the solubility.

Thickened Aqueous gels: These systems include an aqueous phase which has been thickened to achieve a viscosity of at least 500 centipoise (cps), more preferably at least 1,000 cps, even more preferably at least 10,000 cps, even more preferably at least 20,000 cps, even more preferably greater than 50,000 cps, even more preferably greater than 75,000 cps, even more preferably greater than 100,000 cps, and even more preferably at least 250,000 cps (and even as high as 500,000 cps, 1,000,000 cps, or more). The viscosity is determined using the Viscosity Test described herein. These systems can be thickened by suitable natural, modified natural, or synthetic polymers as described below. Alternatively, the thickened aqueous gels can be thickened using suitable polyethoxylated alkyl chain surfactants that effectively thicken the composition as well as other non-ionic, cationic, or anionic emulsifier systems. Preferably, cationic or anionic emulsifier systems are chosen for compositions comprising antimicrobial lipids since some polyethoxylated emulsifiers can inactivate the antimicrobial lipids especially at higher concentrations. For certain embodiments, anionic emulsifier systems are used. Examples include the nonioinic systems such as POLAWAX, COSMOWAX, and CROTHIX systems as well as cationic (BEHENYL TMS) and anionic (CRODAPHOS CES) systems from Croda Inc.

Hydrophilic gels and creams: These are systems in which the continuous phase includes at least one water soluble hydrophilic component other than water present in greatest amount. The formulations may optionally also contain water up to 20% by weight or more. Higher levels may be suitable in some compositions. Suitable hydrophilic components include one or more polyhydric alcohols such as glycerin, propylene glycol, dipropylene glycol, polypropylene gycols having a molecular weight less than about 500 and preferably less than 450, butylene glycols, etc., polyethylene glycols (PEG), random or block copolymers of ethylene oxide, propylene oxide, and/or butylene oxide, polyalkoxylated surfactants having one or more hydrophobic moieties per molecule, silicone copolyols, as well as combinations thereof, and the like. One skilled in the art will recognize that the level of ethoxylation should be sufficient to render the hydrophilic component water soluble or dispersible at 23° C. These compositions may be thickened using conventional crystallizable polymers and emulsifiers such as polyethylene glycols and polyethoxylated alkyl ethers and esters. Alternatively, they may be thickened using one or more soluble or swellable polymers such as polyvinylpyrrolidone (povidone), polyvinylalcohol (PVA), copolymers of N-vinyl pyrrolidone, PVAs having vinyl acetate groups such as those made by partial hydrolysis of polyvinyl acetate, polyacrylates, as well as natural polymers and gums such as modified celluloses (e.g., hydroxypropylcellulose, carboxymethyl cellulose, hydroxyethyl cellulose, and the like), guar gum, alginates, xanthan gums, starches, and the like as well as chemical modifications there of such as but not limited to cationic forms. In most embodiments, the water content is less than 20%, preferably less than 10%, and more preferably less than 5% by weight of the composition.

Dispersible Gels and Creams: These are systems in which the continuous phase includes at least one water dispersible hydrophilic component in greatest amount. The water dispersible components are typically amphipathic compounds such as polyethoxylated ethers and esters. For example, particularly preferred components include PEG 4-PEG 50 glyceryl alkylates formed by making the alkyl esters of polyethoxylated glycerin, PEG 10-PEG 100 castor oil (or hydrogenated castor oil) such as PEG 30 castor oil and PEG 40 hydrogenated castor oil, PEG 3-PEG 40 esters or ethers of unsaturated lipids such as PEG 6 oleate, PEG 8 dioleate, oleth-6, and the like. In most embodiments, the water content is less than 20%, preferably less than 10%, and more preferably less than 5% by weight of the composition.

Antimicrobial Component

The antimicrobial component can include antiseptics, antibiotics, or combinations thereof. Typically, and preferably, the antimicrobial component includes antiseptics. The antimicrobial component is generally considered the main active component of the compositions described herein.

The antimicrobial component preferably includes an antiseptic selected from one of the following classes: an antimicrobial lipid; a phenolic antiseptic; a cationic antiseptic; iodine and/or an iodophor; a peroxide antiseptic; an antimicrobial natural oil; or combinations thereof.

Cationic antiseptics suitable for use in the present invention include, for example: biguanides, bisbiguanides, and polymeric biguanides, such as chlorhexidine and its various salts, including but not limited to, the digluconate, diacetate, dimethosulfate, and dilactate salts, as well as combinations thereof, and polyhexamethylenebiguanide; polymeric quaternary ammonium compounds, such aspolyacrylates comprising alkyldimethylammonium salts such as disclosed in International Publication No. WO 2002/10244; silver and various silver complexes; small molecule quaternary ammonium compounds, such as benzalkoium chloride and alkyl substituted derivatives, di-long chain alkyl (i.e., C8-C18) quaternary ammonium compounds, cetylpyridinium halides and their derivatives, benzethonium chloride and its alkyl substituted derivatives, octenidine, and compatible combinations thereof. The classes of cationic antiseptics are discussed further below.

In certain embodiments, the antimicrobial component does not include chlorhexidine. For example, when the internal cavity comprises a nasal passage, vagina, or oral cavity, the antimicrobial component does not include chlorhexidine.

Antibiotics

Examples of preferred antibiotics include neomycin sulfate, bacitracin, mupirocin, polymyxin, gentamycin, nitrofurantoin, sulfamethoxazole trymethoprim, rifampin, tetracycline, lysostaphin, and combinations thereof. Suitable antibiotic agents include, but are not limited to, beta-lactam antibacterials such as natural and synthetic penicillin type agents including penam penicillins (such as benzyl penicillin, phenoxymethyl penicillin, coxacillin, nafcillin, methicillin, oxacillin, amoxycillin, temocillin, ticarcillin, and the like), penicillinase-stable penicillins, acylamino and carboxypenicillins (such as piperacillin, azlocillin, mezlocillin, carbenicillin, temocillin, ticarcillin, and the like), and broader spectrum penicillins (such as streptomycin, neomycin, framycetin, gentamicin, apramycin, amikacin, spectinomycin, amoxycillin, ampicillin, and the like), cephalosporins, macrolides (such as tylosin, tilmicosin, aivlosin, erythromycin, azithromycin, spiramycin, josamycin, kitasamycin, and the like), lincosamides (such as lincomycin, clindamycin, pirlimycin, and the like), pleuromutilins (such as tiamulin, valnemulin, and the like), polypeptides, glycopeptides (such as vancomycin, and the like), polymixins (such as polymixin B, polymixin E and the like), sulfonamides (such as sulfamethazine, sulfadiazine, silver sulfadiazine, sulfatroxazole, sulfamethoxypyridazine, sulfanilamide, sulfamethoxazole, sulfisoxazole, sulfamethizole, mafenide, and the like, alone or in combination with trimethoprim), chloramphenicol, thiamphenicol, florfenicol, tetracycline type agents (such as tetracycline, chlortetracycline, oxytetracycline, domeclocycline, doxycycline, minocycline, and the like), quinolones and fluoroquinolones (such as ciprofloxacin, enoxacin, grepafloxacin, levofloxacin, lomefloxacin, norfloxacin, ofloxacin, sparfloxacin, trovafloxacin, cinocacin, nalidixic acid, and the like), tiamulin, colistin, meropenem, sulbactam, tazobactam, methacycline, pyrimethamine, sulfacetamide, oxazolidinones, e.g., eperezolid, linezolid, N-((5S)-3-(3-fluoro-4-(4-(2-fluoroethyl)-3-oxy-1-p-piperazinyl)phenyl-2-oxy-5-oxazolidinyl) methyl)acetamide, (S)—N-((3-(5-(3-pyridyl)thiophen-2-yl)-2-oxy-5-oxazolidinyl)methyl)acetamide, 2,2-difluoro-N-({(5S)-3-[3-fluoro-4-(4-glycoloylpiperazin-1-yl)pheny-1]-2-oxo-1,3-oxazolidin-5-yl}methyl)ethanethioamide, (S)—N-((3-(5-(4-pyridyl)pyrid-2-yl)-2-oxy-5-oxazolidinyl) methyl)acetamide hydrochloride, and the like, aminoglycosides (kanamycin, tobramycin, netilmicin, and the like), aminocyclitols, amphenicol, ansamycin, carbaphenern, cephamycin, rifampicin, monobactam, oxacephem, streptogramins (such as quinupristin, dalfopristin, and the like), cycloserines, mupirocin, urea hydroxamates, folic acid analogs (such as trimethoprim, and the like), antibiotic-type antineoplastic agents (such as aclarubicin, actinomycin D, actinoplanone, aeroplysinin derivative, Nippon Soda anisomycins, anthracycline, azino-micyin-A, busucaberin, bleomycin sulfate, bryostatin-1, calichemycin, chromoximycin, dactinomycin, daunorubicin, ditrisarubicin B, doxorubicin, doxorubicin-fibrinogen, elsamicin-A, epirubicin, erbstatin, esorubicin, esperamicin-Alb, fostriecin, glidobactin, gregatin-A, grincamycin, herbimycin, idarubicin, illudins, kazusamycin, kesarirhodins, menogaril, mitomycin, mitoxantorone, mutamycin, mycophenolate mofetil, neoenactin, oxalysine, oxaunomycin, peplomycin, pilatin, pirarubicin, porothramycin, pyrindamycin A, rapamycin, rhizoxin, rodorubicin, sibanomicin, siwenmycin, sorangicin-A, sparsomycin, steffimycin B, talisomycin, terpentecin, thrazine, tricrozarin A, zorubicin, systemic antibacterials (such as 2,4-diaminopyrimidine), nitrofuran sulfones, narbofloxacin, and the like, and combinations thereof.

If an antibiotic is used in compositions of the present invention, they are typically used in combination with an antiseptic. Preferred compositions, however, are free of antibiotics due to the chance of resistance formation.

Antimicrobial Lipids

The antimicrobial lipid component is that component of the composition comprising at least one branched or straight chain alkyl or alkylene group of at least 6 carbon atoms, preferably at least 7 carbon atoms, and more preferably at least 8 carbon atoms, wherein the antimicrobial lipid component provides at least part of the antimicrobial activity. That is, the antimicrobial lipid component has at least some antimicrobial activity for at least one microorganism.

In certain embodiments, the antimicrobial lipid preferably has a solubility in water of no greater than 1.0 gram per 100 grams (1.0 g/100 g) deionized water. More preferred antimicrobial lipids have a solubility in water of no greater than 0.5 g/100 g deionized water, even more preferably, no greater than 0.25 g/100 g deionized water, and even more preferably, no greater than 0.10 g/100 g deionized water. Preferred antimicrobial lipids have a solubility in deionized water of at least 100 micrograms (µg) per 100 grams deionized water, more preferably, at least 500 µg/100 g deionized water, and even more preferably, at least 1000 µg/100 g deionized water.

The antimicrobial lipids preferably have a hydrophile/lipophile balance (HLB) of at most 6.2, more preferably at most 5.8, and even more preferably at most 5.5. The antimicrobial lipids preferably have an HLB of at least 3, preferably at least 3.2, and even more preferably at least 3.4.

Preferred antimicrobial lipids are uncharged and have an alkyl or alkenyl hydrocarbon chain containing at least 7 carbon atoms.

In certain embodiments, the antimicrobial lipid component preferably includes one or more fatty acid esters of a polyhydric alcohol, fatty ethers of a polyhydric alcohol, or alkoxylated derivatives thereof (of either or both of the ester and ether), or combinations thereof. More specifically and preferably, the antimicrobial component is selected from the group consisting of a (C7-C14)saturated fatty acid ester of a polyhydric alcohol (preferably, a (C7-C12)saturated fatty acid ester of a polyhydric alcohol, more preferably, a (C8-C12)saturated fatty acid ester of a polyhydric alcohol), a (C8-C22)unsaturated fatty acid ester of a polyhydric alcohol (preferably, a (C12-C22)unsaturated fatty acid ester of a polyhydric alcohol), a (C7-C14)saturated fatty ether of a polyhydric alcohol (preferably, a (C8-C12)saturated fatty ether of a polyhydric alcohol, more preferably, a (C8-C12) saturated fatty ether of a polyhydric alcohol), a (C8-C22) unsaturated fatty ether of a polyhydric alcohol (preferably, a (C12-C22)unsaturated fatty ether of a polyhydric alcohol), an alkoxylated derivative thereof, and combinations thereof. Preferably, the esters and ethers are monoesters and monoethers, unless they are esters and ethers of sucrose in which case they can be monoesters, diesters, monoethers, or monoethers. Various combinations of monoesters, diesters, monoethers, and diethers can be used in a composition of the present invention.

A fatty acid ester of a polyhydric alcohol is preferably of the formula $(R^1—C(O)—O)_n—R^2$, wherein $R^1$ is the residue of a (C7-C14)saturated fatty acid (preferably, a (C7-C12) saturated fatty acid, more preferably, a (C8-C12)saturated fatty acid), or a (C8-C22)unsaturated fatty acid (preferably, a C12-C22)unsaturated, including polyunsaturated, fatty acid), $R^2$ is the residue of a polyhydric alcohol (typically and preferably, glycerin, propylene glycol, and sucrose, although a wide variety of others can be used including pentaerythritol, sorbitol, mannitol, xylitol, etc.), and n=1 or 2. The $R^2$ group includes at least one free hydroxyl group (preferably, residues of glycerin, propylene glycol, or sucrose). Preferred fatty acid esters of polyhydric alcohols are esters derived from C7, C8, C9, C10, C11, and C12 saturated fatty acids. For embodiments in which the polyhydric alcohol is glycerin or propylene glycol, n=1, although when it is sucrose, n=1 or 2.

Exemplary fatty acid monoesters include, but are not limited to, glycerol mono esters of lauric (mono laurin), caprylic (monocaprylin), and capric (monocaprin) acid, and propylene glycol monoesters of lauric, caprylic, and capric acid, as well as lauric, caprylic, and capric acid monoesters of sucrose. Other fatty acid monoesters include glycerin and propylene glycol monoesters of oleic (18:1), linoleic (18:2), linolenic (18:3), and arachonic (20:4) unsaturated (including polyunsaturated) fatty acids. As is generally known, 18:1, for example, means the compound has 18 carbon atoms and 1 carbon-carbon double bond. Preferred unsaturated chains have at least one unsaturated group in the cis isomer form. In certain preferred embodiments, the fatty acid monoesters that are suitable for use in the present composition include known monoesters of lauric, caprylic, and capric acid, such as that known as GML or the trade designation LAURICIDIN (the glycerol monoester of lauric acid commonly referred to as monolaurin or glycerol monolaurate), glycerol monocaprate, glycerol monocaprylate, propylene glycol monolaurate, propylene glycol monocaprate, propylene glycol monocaprylate, and combinations thereof.

Exemplary fatty acid diesters of sucrose include, but are not limited to, lauric, caprylic, and capric diesters of sucrose, as well as combinations thereof.

A fatty ether of a polyhydric alcohol is preferably of the formula $(R^3—O)_n—R^4$, wherein $R^3$ is a (C7-C14)saturated aliphatic group (preferably, a (C7-C12)saturated aliphatic group, more preferably, a (C8-C12)saturated aliphatic group), or a (C8-C22)unsaturated aliphatic group (preferably, a (C12-C22)unsaturated, including polyunsaturated, aliphatic group), $R^4$ is the residue of glycerin, sucrose, or propylene glycol, and n=1 or 2. For glycerin and propylene glycol n=1, and for sucrose n=1 or 2. Preferred fatty ethers are monoethers of (C7-C14)alkyl groups (more preferably (C7-C12)alkyl groups, and even more preferably, (C8-C12) alkyl groups).

Exemplary fatty monoethers include, but are not limited to, laurylglyceryl ether, caprylglycerylether, caprylylglyceryl ether, laurylpropylene glycol ether, caprylpropyleneglycol ether, and caprylylpropyleneglycol ether. Other fatty monoethers include glycerin and propylene glycol monoethers of oleyl (18:1), linoleyl (18:2), linolenyl (18:3), and arachonyl (20:4) unsaturated and polyunsaturated fatty alcohols. In certain preferred embodiments, the fatty monoethers that are suitable for use in the present composition include laurylglyceryl ether, caprylglycerylether, caprylyl glyceryl ether, laurylpropylene glycol ether, caprylpropyleneglycol ether, caprylylpropyleneglycol ether, and combinations thereof. Unsaturated chains preferably have at least one unsaturated bond in the cis isomer form.

Alternatively, the antimicrobial lipid can be a (C7-C14) fatty alcohol ester (preferably a (C8-C12)fatty alcohol ester) of a (C2-C8)hydroxycarboxylic acid (also often referred to as a (C7-C14) or (C2-C8)hydroxycarboxylic acid ester of a (C8-C12)fatty alcohol), a (C8-C22)mono- or poly-unsaturated fatty alcohol ester of a (C2-C8)hydroxycarboxylic acid (also often referred to as a (C2-C8)hydroxycarboxylic acid ester of a (C8-C22)mono- or poly-unsaturated fatty alcohol)), or alkoxylated derivatives thereof. The hydroxycarboxylic acid moiety can include aliphatic and/or aromatic groups. For example, fatty alcohol esters of salicylic acid are possible.

For some embodiments, the antimicrobial lipid is a (C7-C14)fatty alcohol ester (preferably a monoester) of a (C2-C8)hydroxycarboxylic acid (preferably a (C7-C12)fatty alcohol ester (preferably a monoester) of a (C2-C8)hydroxycarboxylic acid, and more preferably a (C8-C12)fatty alcohol ester (preferably a monoester) of a (C2-C8)hydroxycarboxylic acid, a (C8-C22)mono- or poly-unsaturated fatty alcohol ester of a (C2-C8)hydroxycarboxylic acid, or combinations thereof. Herein, a "monoester" is that there is only 1 alkyl or aralkyl group and thus a free hydroxyl group.

The hydroxyacids typically have one hydroxyl group and one carboxylic acid group. They are preferably selected from alpha- and beta-hydroxyacids described below. The fatty alcohols are most preferably straight or branched alkyl alcohols having 7-14 carbon atoms, and most preferably 7-12 carbon atoms, or a (C8-C22)unsaturated fatty alcohol (preferably, a C12-C22)unsaturated, including polyunsaturated, fatty alcohol).

A fatty alcohol ester of a hydroxyl functional carboxylic acid preferably has the formula:

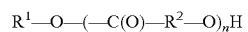

wherein: $R^1$ is the residue of a (C7-C14)saturated alkyl alcohol (preferably, a (C7-C12)saturated alkyl alcohol, more preferably, a (C8-C12)saturated alkyl alcohol), or a (C8-C22)unsaturated alcohol (including polyunsaturated alcohol); $R^2$ is the residue of a hydroxycarboxylic acid wherein the hydroxycarboxylic acid has the following formula:

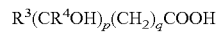

wherein: $R^3$ and $R^4$ are each independently H or a (C1-C8) saturated straight, branched, or cyclic alkyl group, a (C6-C12)aryl group, a (C6-C12)aralkyl or (C6-C12)alkaryl group (wherein the alkyl groups of the aralkyl and alkaryl groups are saturated straight, branched, or cyclic), wherein $R^3$ and $R^4$ may be optionally substituted with one or more carboxylic acid groups; p=1 or 2; and q=0-3; and n=1, 2, or 3. The $R^3$ group may include one or more free hydroxyl groups, but preferably is free of hydroxyl groups. Preferred fatty alcohol esters of hydroxycarboxylic acids are esters derived from branched or straight chain C8, C9, C10, C11, and C12 alkyl alcohols. Preferred hydroxyacids typically have one hydroxyl group and one carboxylic acid group.

Exemplary fatty alcohol esters of hydroxycarboxylic acids include, but are not limited to, (C7-C14), and preferably (C8-C12), fatty alcohol esters of lactic acid such as octyl lactate, 2-ethylhexyl lactate (PURASOLV EHL from Purac, Lincolnshire, Ill.), lauryl lactate (CHRYSTAPHYL 98 from Chemic Laboratories, Canton, Mass.), lauryl lactyl lacate, 2-ethylhexyl lactyl lactate; (C7-C14), and preferably (C8-C12), fatty alcohol esters of 3-hydroxybutanoic acid, mandelic acid, gluconic acid, tartaric acid, and salicylic acid.

The fatty acid esters and fatty ethers of polyhydric alcohols and/or hydroxycarboxylic esters of fatty alcohols can be alkoxylated, preferably ethoxylated and/or propoxylated, by conventional techniques. The alkoxylated derivatives have less than 5 moles of alkoxide per mole of polyhydric alcohol or hydroxyl acid. Alkoxylating compounds are preferably selected from the group consisting of ethylene oxide, propylene oxide, and mixtures thereof, and similar oxirane compounds. The alkoxylated derivatives of the aforementioned fatty acid esters, fatty ethers, and hydroxycarboxylic esters of fatty alcohols (e.g., one which is ethoxylated and/or propoxylated on the remaining alcohol group(s)) also have antimicrobial activity as long as the total alkoxylate is kept relatively low. In the case where the antimicrobial lipid esters and ethers having at least one free —OH group are ethoxylated, the total moles of ethylene oxide is preferably less than 5, and more preferably less than 2.

Alternatively, other antimicrobial lipids include (C6-C14) alkyl carboxylic acids, and (C8-C22)mono- or poly-unsaturated carboxylic acids. These antimicrobial lipids include (C6-C14), preferably (C7-C12), and more preferably (C8-C12)straight chain or branched chain alkyl carboxylic acids, such as heptanoic, carpic, caprylic, undecylenic, 2-ethylhexanoic, and lauric acids. These are often referred to as fatty acids. Also included are (C8-C22)mono- or poly-unsaturated fatty acids (i.e., carboxylic acids). Examples include oleic, linoleic, linolenic, and arachidonic acids.

Other antimicrobial lipids include fatty acid esters formed from one of the above fatty acids with a hydroxyl carboxylic acid (preferably, a hydroxyfunctional alkyl acid). Such fatty acid esters are also known as alkyl carboxylate esters of carboxylic acids, and include examples such as lauroyl lactylate, capryloyl lactylate (capryl ester of lactyl lactate), or caproyl lactylate. As used herein "formed from" refers to an example of how these compounds may be formed and is used to describe the chemical identity of the ester so formed. It is recognized that other synthetic routes may be used. For example, the acid halide of the fatty acid may be reacted with a hydroxycarboxylic acid or a derivative thereof. A fatty acid ester of a hydroxyl functional carboxylic acid (i.e., alkyl carboxylate ester carboxylic acid) preferably has the formula:

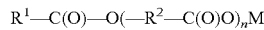

wherein $R^1$ is the residue of a (C6-C14)saturated alkyl carboxylic acid (preferably, a (C7-C12)saturated alkyl carboxylic acid, more preferably, a (C8-C12)saturated alkyl carboxylic acid) or a (C8-C22)unsaturated alkylene carboxylic acid (including polyunsaturated carboxylic acid), $R^2$ is the residue of a hydroxycarboxylic acid wherein the hydroxycarboxylic acid has the following formula:

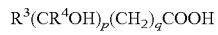

wherein: $R^3$ and $R^4$ are each independently H or a (C1-C8) saturated straight, branched, or cyclic alkyl group, a (C6-C12)aryl group, or a (C6-C12)aralkyl or (C6-C12)alkaryl group (wherein the alkyl groups of the aralkyl and alkaryl groups are saturated straight, branched, or cyclic groups), wherein $R^3$ and $R^4$ may be optionally substituted with one or more carboxylic acid groups; p=1 or 2; and q=0-3; and n=1, 2, or 3. The $R^3$ group may include one or more free hydroxyl groups. Preferred fatty acid esters of hydroxycarboxylic acids are esters derived from branched or straight chain C8, C9, C10, C11, and C12 alkyl carboxylic acids. M is a cationic counterion such as H, Na, K, Li, ammonium, or a protonated tertiary amine such as triethanolamine or a quaternary ammonium group. M also may be polyvalent metals such as Ca, Mg, Fe, and the like in which case there would need to be a stoichiometric ratio of lipid ester carboxylate to metal ion.

The fatty acid esters of hydroxyl carboxylic acids are preferably but not necessarily formed by esterification of a (C6-C14)saturated linear or branched alkylcarboxylic acid or a (C8-C22)mono- or poly-unsaturated fatty acid with a hydroxyfunctional alkyl carboxylic acid. Preferred such antimicrobial lipids include a (C8-C12)fatty acid ester of a (C2-C8)hydroxycarboxylic acid, a (C8-C22)mono- or poly-unsaturated fatty acid ester of a (C2-C8) hydroxycarboxylic acid, or combinations thereof.

A commercially available example of an alkyl carboxylate ester of an alkyl carboxylic acid is PATIONIC 122A (sodium caproyl lactylate also known as sodium caproyl lactyl lactate) available from RITA Corp. Other preferred compounds of this class are 2-ethylhexoyl lactate, lauroyl lactylate and lauroyl lactyl lactate. It is preferred to formulate these antiseptics in the presence of a hydrophobic component and/or an emulsifier/surfactant.

At least a portion of the carboxylic acid preferably is present in the acid or protonated form. This form has significantly greater activity than the neutralized salt form. Since these acids can also be relatively irritating they are preferably formulated in compositions based on hydrophobic vehicles such as emollient oils or petrolatum which may optionally contain a hydrophilic component. The pH of aqueous compositions (or the aqueous phase of the compositions) formulated with these antiseptics typically range from 3 to 8 and most preferably from 3 to 6.

The compositions described herein include one or more antimicrobial lipids at a suitable level to produce the desired result. Such compositions preferably include a total amount of such material of at least 0.01 percent by weight (wt-%), more preferably at least 0.1 wt-%, even more preferably at least 0.25 wt-%, even more preferably at least 0.5 wt-%, and even more preferably at least 1 wt-%, based on the total weight of the "ready to use" or "as used" composition. In a preferred embodiment, they are present in a total amount of up to 99% by weight if they are used at the antimicrobial component as well as the vehicle. Generally, they are used at no greater than 60 wt-%, more preferably no greater than 50 wt-%, even more preferably no greater than 30 wt-%, even more preferably no greater than 20 wt-%, and even more preferably no greater than 10 wt-%, based on the "ready to use" or "as used" composition.

Many antimicrobial lipids are effective at levels of less than 5% by weight of composition. Certain compositions may be higher in concentration if they are intended to be diluted prior to use or if the antimicrobial lipid is used as the vehicle. For example, certain antimicrobial lipids that are liquid at room temperature can be used as the antimicrobial component and the vehicle and thus may be present in concentrations as high as 90% or more.

Preferred compositions described herein that include one or more fatty acid monoesters, fatty monoethers, or alkoxylated derivatives thereof can also include a small amount of a di- or tri-fatty acid ester (i.e., a fatty acid di- or tri-ester), a di- or tri-fatty ether (i.e., a fatty di- or tri-ether), or alkoxylated derivative thereof. Preferably, such components are present in an amount of no more than 50 wt-%, more preferably no more than 40 wt-%, even more preferably no more than 25 wt-%, even more preferably no more than 15 wt-%, even more preferably no more than 10 wt-%, even more preferably no more than 7 wt-%, even more preferably no more than 6 wt-%, and even more preferably no more than 5 wt-%, based on the total weight of the antimicrobial lipid component. For example, for monoesters, monoethers, or alkoxylated derivatives of glycerin, preferably there is no more than 15 wt-%, more preferably no more than 10 wt-%, even more preferably no more than 7 wt-%, even more preferably no more than 6 wt-%, and even more preferably no more than 5 wt-% of a diester, diether, triester, triether, or alkoxylated derivatives thereof present, based on the total weight of the antimicrobial lipid components present in the composition. However, as will be explained in greater detail below, higher concentrations of di- and tri-esters may be tolerated in the raw material if the formulation initially includes free glycerin because of transesterification reactions.

Although in some situations it is desirable to avoid di- or tri-esters as a component of the starting materials, it is possible to use relatively pure tri-esters in the preparation of certain compositions described herein (for example, as a hydrophobic component) and have effective antimicrobial activity.

In certain embodiments, preferred antimicrobial lipids include compounds selected from the group consisting of a (C7-C14)saturated fatty acid ester of a polyhydric alcohol, a (C8-C22)unsaturated fatty acid ester of a polyhydric alcohol, a (C7-C14)saturated fatty ether of a polyhydric alcohol, a (C8-C22)unsaturated fatty ether of a polyhydric alcohol, a (C7-C14)fatty alcohol ester of a (C2-C8) hydroxycarboxylic acid, a (C8-C22)mono- or poly-unsaturated fatty alcohol ester of a (C2-C8)hydroxycarboxylic acid, a (C8-C12)fatty acid ester of a (C2-C8)hydroxycarboxylic acid, a (C8-C22) mono- or poly-unsaturated fatty acid ester of a (C2-C8) hydroxycarboxylic acid, an alkoxylated derivative of any of the foregoing having a free hydroxyl group, and combinations thereof; wherein the alkoxylated derivative has less than 5 moles of alkoxide per mole of polyhydric alcohol or hydroxycarboxylic acid; with the proviso that for polyhydric alcohols other than sucrose, the esters comprise monoesters and the ethers comprise monoethers, and for sucrose the esters comprise monoesters, diesters, or combinations thereof, and the ethers comprise monoethers.

In certain embodiments, preferred antimicrobial lipids include glycerol monolaurate, glycerol monocaprate, glycerol monocaprylate, propylene glycol monolaurate, propylene glycol monocaprate, propylene glycol monocaprylate, 2-ethylhexyl laurate, caprylyl lactate, capryl lactate, lauryl lactate, and combinations thereof.

To achieve rapid antimicrobial activity, formulations may incorporate one or more antimicrobial lipids in the composition approaching, or preferably exceeding, the solubility limit in the hydrophobic phase. While not intended to be bound by theory, it appears that antimicrobial lipids that preferably partition into the hydrophobic component are not readily available to kill microorganisms which are in or associated with an aqueous phase in or on the tissue. In most compositions, the antimicrobial lipid is preferably incorporated in at least 60%, preferably, at least 75%, more preferably, at least 100%, and most preferably, at least 120%, of the solubility limit of the hydrophobic component at 23° C. This in conveniently determined by making the formulation without the antimicrobial lipid, separating the phases (e.g., by centrifugation or other suitable separation technique) and determining the solubility limit by addition of progressively greater levels of the antimicrobial lipid until precipitation occurs. One skilled in the art will realize that creation of supersaturated solutions are avoided for an accurate determination. In hydrophilic gels and creams the hydrophilic component is preferably selected to have an antimicrobial lipid solubility greater than that of water. In this manner, the vehicle component can promote the diffusion of the antimicrobial lipid on and into the tissue and any biofilm that may be present on the tissue.

Iodine and Iodophors

Many references have described the preparation of "iodophors," which are complexes of elemental iodine or triiodide with certain carriers. These iodophors function to not only increase the iodine solubility but to reduce the level of free molecular iodine in solution and to provide a type of sustained release reservoir of elemental iodine. Iodophors are known using carriers of polymers such as polyvinylpyrrolidone, copolymers of N-vinyl lactams with other unsaturated monomers such as, but not limited to, acrylates and acrylamides, various polyether glycols including polyether-containing surfactants such as nonylphenolethoxylates, and the like, polyvinyl alcohols, polycarboxylic acids such as polyacrylic acid, polyacrylamides, polysaccharides such as dextrose, and the like, and combinations thereof. A preferred group of iodophors include polymers such as a polyvinylpyrrolidone (PVP), a copolymer of N-vinyl lactam, a polyether glycol (PEG), a polyvinyl alcohol, a polyacrylamide, a polysaccharide, and combinations thereof. Also reported in U.S. Pat. No. 4,957,975 (Woodward) are protonated amine oxide surfactant-triiodide complexes that are also suitable iodophors for use in the present invention. Various combinations of iodophores can be used in the compositions described herein.

A preferred iodophor is povidone-iodine. A particularly preferred iodophor can be obtained commercially as povidone-iodine USP, which is a complex of K30 polyvinylpyrrolidone, iodine, and iodide wherein the available iodine is present at about 9 wt-% to about 12 wt-%.

Preferably, the iodophor is present in the use compositions at a concentration of at least about 0.25 wt-%, more preferably at least about 0.5 wt-%, and most preferably greater than 1 wt-%, based on the total weight of the antimicrobial composition.

Since iodophors may vary in the amount of available iodine it is usually more convenient to describe the concentration in terms of the available iodine level. In the present invention, whether from iodine or an iodophor or a combination thereof, the available iodine concentration is preferably at least about 0.025 wt-%, and more preferably at least about 0.05 wt-%, based on the total weight of the antimicrobial composition. The available iodine is preferably present at not more than about 1.5 wt-%, and preferably not more than about 1 wt-%, based on the total weight of the antimicrobial composition.

The available iodine for most compositions may be determined by following the method in the United States Pharmacopeia Official Monographs for Povidone-Iodine, Assay for Available Iodine. Certain formulations may contain components that can interact with the method such as other anionic species. For this reason, the proper standards must be run to ensure accuracy, and solvent systems or reagents may need to be changed to ensure accuracy. One skilled in the art would appreciate these considerations.

These systems may be especially useful in combination with carboxylic acid buffers as described in U.S. Pat. Publication No. 2003/0194447.

In certain embodiments, the antimicrobial component does not include iodine. For example, when the internal cavity comprises a nasal passage, vagina, or oral cavity (and particularly, a nasal passage or vagina), the antimicrobial component does not include iodine.

Phenolic Antiseptics

The phenolic antiseptic component includes an effective amount of one or more antiseptics selected from the group consisting of diphenyl ethers, phenolics (including halogenated phenolics), bisphenolics, resorcinols, anilides, and compatible combinations thereof.

Phenolic antiseptics suitable for use in the antimicrobial compositions include, but are not limited to, diphenyl ethers, such as the polyhalogenated hydroxy diphenyl ethers, more specifically those containing multiple halogen substituents; phenolics including simple phenolics, such as phenol, cresol, o-phenylphenol, and halogenated phenolics, such as p-chlorometa-xylenol, dichlorometa-xylenol, o-benzyl p-chlorophenol and p-isoamylphenol; bisphenolics, such as 2,2'-methylene-bis(3,4,6-trichlorophenol), 2,2'-methylene-bis(4,6-dichlorophenol), 2,2'-methylene-bis(4-chlorophenol), 2,2'-thio-bis(4,6-dichlorophenol); resorcinols; and anilides, salicylanilide, monohalogenated salicylanilide, and polyhalogenated salicylanilide. The following classes are used in most embodiments:

1. Diphenyl ethers. Diphenyl ethers such as polyhalogenated hydroxyl diphenyl ethers, more specifically those containing multiple halogen substituents, such as triclosan (2',4,4'-trichloro-2-hydroxy-diphenyl ether or 3-chloro-2-(2, 4dichlorophenoxy)phenol), and the like. These compounds can be represented by the following chemical structure:

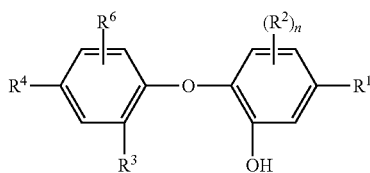

wherein $R^1$ and $R^3$ can be chlorine, bromine, or hydrogen, $R^2$ is chlorine or bromine; $R^4$ can be chlorine, bromine, an alkyl having 1 to 3 carbon atoms, $CH_3O$—, CN—, and $NH_2$—, $R^6$ can be hydrogen, chlorine, bromine, methyl, trichloromethyl, $CH_3O$—, CN—, and $NH_2$—; and n is 1 or 2.

2. Phenolics. Phenolics include phenol and derivatives thereof, including both simple phenolics, such as phenol, cresol, o-phenylphenol, and halogenated phenolics, such as p-chlorometa-xylenol, dichlorometa-xylenol, and p-isoamylphenol. Other phenolics include mono- and poly-alkyl and aromatic halophenols (e.g., methyl-p-chlorophenol, n-butyl-p-chlorophenol, o-chlorophenol, o-benzyl-p-chlorophenol, o-phenylethyl-m-methyl-p-chlorophenol, 6-iso-propyl-2-ethyl-3-methyl-p-chlorophenol, methyl-p-bromophenol, tert-amyl-o-bromophenol, 3,4,5,6-terabromo-2-methylphenol. A preferred antiseptic of this class is p-chloro-m-xylenol (PCMX).

3. Resorcinols. Resorcinols include resorcinol and its derivatives. Examples of such compounds include methyl-resorcinol, ethyl-resorcinol, n-propyl-resorcinol, n-butyl-resorcinol, n-amyl-resorcinol, n-hexyl-resorcinol, 4-hexyl-resorcinol, n-heptyl-resorcinol, n-octyl-resorcinol, n-nonyl-resorcinol, phenyl-resorcinol, benzyl-resorcinol, phenylethyl-resorcinol, phenylpropyl-resorcinol, p-chlorobenzyl-resorcinol, 5-chloro-2,4-dihydroxydiphenyl methane, 4'-chloro-2,4-dihydroxydiphenyl methane, 5-bromo-2, 4-dihydroxydiphenyl methane, 4'-bromo-2,4-dihydroxydiphenyl methane, and thymol enjenol.

4. Bisphenolics. Bisphenolics include 2,2'-methylene bis (4-chlorophenol), 2,2'-methylene bis(3,4,6-trichlorophenol), 2,2'-methylene bis(4-chloro-6-bromophenol), bis(2-hydroxy-3,5-dichlorophenyl) sulfide, and bis(2-hydroxy-5-chlorobenzyl) sulfide.

5. Anilides. Anilides include salicylanilides and carbanilides such as those discussed in *Disinfection Sterilization, and Preservation,* $2^{nd}$ Ed. Edited by Seymour S. Block, Chapter 14, Lea & Febiger, Philadelphia, Pa., 1977; halogenated carbanilide compounds as described in U.S. Pat. No. 2,818,390, and halogenated salicylanilides including monohalogenated salicylanilide and polyhalogenated salicylanilide. Particularly preferred carbanilide compounds are 3,4,4'-trichlorocarbanilide (triclocarban); 3,4',5-tribromosalicylanilide; 4,4'-dichloro-3'-(trifluoromethyl) carbanilide. Other anilides may be useful including, but not limited to, salicylanilide, monohalogenated salicylanilide, and polyhalogenated salicylanilide such as those disclosed in U.S. Pat. Nos. 4,010,252 and 4,894,220.

These compounds may be relatively water insoluble and thus it is preferred to formulate these compounds in the presence of a hydrophobic component and/or an emulsifier/surfactant, in an emulsion (water-in-oil or oil-in-water), or in a hydrophilic vehicle (e.g., other than water). These compounds are typically added to the formulations in amounts of 0.5% by weight, and preferably 1% by weight. In most embodiments, the compounds are added in amounts of no greater than 20 wt-%, preferably no more than 12 wt-%, more preferably no more than 8 wt-%, and even more preferably no greater than 6 wt-%.

Biguanides, Bisbiguanides, and Polymeric Biguanides

This class of antiseptics is represented by the formula:

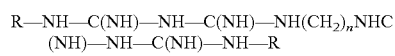

R—NH—C(NH)—NH—C(NH)—NH(CH$_2$)$_n$NHC(NH)—NH—C(NH)—NH—R wherein n=3-10, preferably 4-8, and most preferably 6; and R=(C4-C18)branched or straight chain alkyl optionally substituted in available positions by halogen or (C6-C12) aryl or alkaryl optionally substituted in available positions by halogen.

The preferred compound of this class is chlorhexidine. This may be present as the free base but is preferably present as a disalt of acetate, gluconate, lactate, methosulfate ($CH_3OSO_3$—), or a halide or combinations thereof. Most preferred are the diacetate, digluconate, dilactate, and dimethosulfate salts since these salts all have solubility limits in excess of 1 g/100 mL. For example, the solubility limit of the digluconate salt is 20 g/100 mL and that of the diacetate is 1.9 g/100 mL. The most preferred compound is chlorhexidine digluconate (CHG). Other anions may be useful. It is particularly important, however, with this class as well as other cationic antiseptics to use a counter ion that ensures solubility in aqueous fluid above the minimum inhibitory concentration (MIC) of the treatment organism. If the solubility limit is less than the MIC, treatment may be ineffective.

The antiseptics of this class are particularly preferred in formulations that are non-aqueous and protected from light. This is believed to reduce the degradation of the compound. When used in compositions that include less than about 20% by weight water, antiseptics of this class are preferably formulated with a hydrophilic carrier that solubilizes the antiseptic. Examples of suitable solvents for chlorhexidine gluconate include glycols (compounds having at least two hydroxylgroups per molecule) such as PEGs having a molecular weight below 2000 and preferably less than 1000 and most preferably less than about 800 daltons; glycerin and polyglycerols, propylene glycol, dipropylene glycol, tripropyelne glycol, polypropylene glycol, ethylene oxide/propylene oxide random or block copolymers, trimethylolpropane, pentraerithiritol, sorbitol, panetothenol, glucuronolactone, gluconic acid, and the like, as well as other polar solvents such as N-methylpyrrolidone, propylene carbonate, butyrolactone, and the like.

Care must also be taken when formulating chlorhexidine as well as other cationic antiseptic compounds to avoid inactivation by sequestering it in micelles, which may be formed by incorporation of surfactants and/or emulsifiers. Preferred formulations are hydrophilic ointments; aqueous solutions thickened with polymeric thickeners that are either surfactant free or contain surfactants that do not reduce the activity of the CHG, such as poloxamers; and ointments comprising a major amount of a hydrophobic component and preferably further comprising a hydrophilic component.

Bis(biguanide)s such as chlorhexidine are very basic and capable of forming multiple ionic bonds with anionic materials. For this reason, biguanide-containing compositions are preferably free of anioinic compounds that can result in precipitation of the antiseptic. For this reason, thickener systems, if present, are preferably based on non-ionic and/or cationic polymers or emulsifiers. Anionic surfactants useful, for example, as wetting agents, may also need to be avoided. Certain zwitterionic, very water soluble, or non-precipitating anionic emulsifiers and surfactants may also be useful. Halide salts may need to be avoided. For example, chlorhexidine digluconate (CHG) will precipitate rapidly in the presence of halide salts above a concentration of about 0.1M. Therefore, if a system includes CHG or other antiseptic of this class, and needs to comprise salts for stability or other purposes, preferably gluconate salts such as triethanolamine gluconate or sodium gluconate, are used. In addition, if an additional antiseptic is incorporated into the composition it is preferably non-ionic or cationic.

Preferably, if used, biguanides and bisbiguanides are present in a composition in an amount of at least 0.5 wt-%, based on the total weight of the composition.

A particularly preferred class of polymeric antiseptic compounds are polybiguanides. Compounds of this class are represented by the formula:

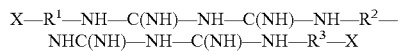

wherein: $R^1$, $R^2$, and $R^3$ are bridging groups such as polymethylene groups preferably having 2 to 10 methylene groups, more preferably 4 to 8 methylene groups and most preferably 6 methylene groups. The methylene groups can be optionally substituted in available positions with halogen, hydroxyl, or phenyl groups. X is a terminal group and is typically an amine, amine salt, or a dicyandiamide group. The preferred compound of this class is polyhexamethylene biguanide (PHMB) commercially available as Cosmocil CQ from Aveci, Wilmington, Del.

Poly(biguanide) antiseptics such as PHMB are very basic and are capable of forming multiple ionic bonds with anionic materials. For this reason, biguanide-containing compositions are preferably free of anionic compounds that can result in precipitation and/or inactivation of the antiseptic. For this reason, thickener systems, if present, are preferably based on non-ionic and/or cationic polymers or emulsifiers. Anionic surfactants useful, for example, as wetting agents, may also need to be avoided. Certain zwitterionic, very water soluble, or non-precipitating anionic emulsifiers and surfactants may also be useful. Halide salts also may need to be avoided.

Polymeric Quaternary Amine Compounds

Antimicrobial polymers comprising quaternary amine groups may also be used as the antiseptic of the present invention. These are typically polymers having quaternary amine groups with at least one alkyl or aralkyl chain of at least 6 carbon atoms and preferably as least 8 carbon atoms. The polymers may be linear, branched, hyperbranched or dendrimers. Preferred antimicrobial polymeric quaternary amine polymers include those described in U.S. Pat. Nos. 6,440,405; 5,408,022; and 5,084,096; International Publication No. WO 02/102244; and S. Block, *Disinfection, Sterilization and Preservation,* 4$^{th}$ ed., 1991, Chapter 13, Lea & Febiger.

Compounds of this class are typically used at levels of at least 0.05% by weight, preferably at least 0.1% by weight, even more preferably at least 0.25% by weight, and most preferably at least 0.5% by weight, based on the total weight of the composition. Compounds of this class are preferably used at levels less than about 8%, more preferably less than about 6%, and most preferably less than about 4% by weight of the composition.

Silver and Silver Complexes

Silver is also known to be an effective antiseptic and has been used in creams to treat wounds and other topical infections. Silver may also be useful for nasal decolonization. The active form of silver is the ion Ag+ which may be delivered from a variety of well known silver salts and complexes including silver zeolites; inorganic silver salts such as silver nitrate, silver chloride, silver sulfate, silver thiosulfate; silver alkyl, aryl, and aralkyl carboxylates (preferred carboxylate anions have less than about 8 carbon atoms such as the acetate, lactate, salicylate, and gluconate salts); silver oxide, colloidal silver, nanocrystalline silver, silver coated microspheres, silver complexed with various polymers as well as silver delivered from dendrimers as described in U.S. Pat. Nos. 6,579,906 and 6,224,898; and silver antimicrobial complexes such as silver sufadiazine. The silver may optionally complexed with primary, secondary, tertiary, and quaternary amines as well as polymeric forms thereofs, and silver protein complexes.

Where skin discoloration is undesirable, certain silver complexes can be used, such as those disclosed, for example, in U.S. Pat. Nos. 6,468,521; 5,326,567; 5,429,819; and 5,326,567. Surprisingly, these silver compounds and ions can be delivered from the hydrophobic vehicle compositions described herein. Particularly preferred compositions have a hydrophilic component incorporated into the composition. Silver antiseptics may also be delivered from compositions comprising hydrophobic component(s) as the vehicle.

Silver containing compositions must be protected from light and precipitating excipients. For example, some anionic surfactants could result in inactivation of the silver. Therefore, preferred wetting agents, penetration enhancers, and/or emulsifiers are non-ionic, cationic or zwitterionic. The anions of the cationic surfactants also should be chosen to prevent inactivation of the silver. Preferred surfactants are non-ionic and amine functional surfactants (including primary, secondary, tertiary and quaternary amine-group-containing surfactants).

Preferably, the concentration of silver ion in the antimicrobial compositions is at least 0.20 wt-%, more preferably at least 0.5 wt-%, and most preferably at least 0.75 wt-%, based on the total weight of the composition. Preferably, the silver concentration is less than 10 wt-%, more preferably less than 8 wt-%, and most preferably less than 6 wt-%, based on the total weight of the composition. Silver salts and complexes should be adjusted accordingly based on molecular weight to achieve the silver ion concentration in the ranges described, as one skilled in the art understands.

Silver compounds when used in the present compositions are capable of producing silver ion when in contact with microorganisms. Examples are silver salts and silver oxides. Preferred compounds are silver nitrate, silver thiosulfate, silver chloride, silver phosphate, silver sulfate, and silver halide salts.

Small Molecule Quaternary Ammonium Compounds

This class of compounds typically includes one or more quaternary ammonium groups wherein attached to the quaternary ammonium group is at least one C6-C18 linear or branched alkyl or aralkyl chain. Suitable compounds include those disclosed in S. Block, *Disinfection, Sterilization and Preservation*, 4$^{th}$ ed., 1991, Chapter 13, Lea & Febiger. Particularly preferred compounds of this class have one or two C8-C18 alkyl or aralkyl chains and may be represented by the following formula:

$R^1R^2NR^3R^{4+}X^-$ wherein $R^1$ and $R^2$ are (C1-C18)linear or branched alkyl, alkaryl, or aralkyl chains that may be substituted in available positions by N, O, or S provided at least one $R^1$ or $R^2$ is a (C8-C18)linear or branched alkyl, alkaryl, or aralkyl chains that may be substituted in available positions by N, O, or S. The $R^3$ and $R^4$ groups are C1-C6 alkyl, phenyl, benzyl, or (C8-C12)alkaryl groups. The $R^3$ and $R^4$ groups may also form a ring such as a pyridine ring with the nitrogen of the quaternary ammonium group. X is an anion, preferably a halide, and most preferably Cl— or Br—. Other anions may include methosulfate, ethosulfate, phosphates, and the like. Preferred compounds of this class include monoalkyltrimethylammonium salts, monalkyldimethylbenzyl ammonium salts, dialkyldimethyl ammonium salts, benzethonium chloride, and octenidine.

Examples of preferred quaternary ammonium antiseptics include benzalkonium halides having an alkyl chain length of C8-C18, more preferably C12-C16, and most preferably a mixture of chain lengths. For example, a typical benzalkonium chloride sample may be comprise of 40% C12 alkyl chains, 50% C14 alkyl chains, and 10% C16 alkyl chains. These are commercially available from numerous sources including Lonza (BARQUAT MB-50); Benzalkonium halides substituted with alkyl groups on the phenyl ring. A commercially available example is BARQUAT 4250 available from Lonza; dimethyldialkylammonium halides where the alkyl groups have chain lengths of C8-C18. A mixture of chain lengths such as mixture of dioctyl, dilauryl, and dioctadecyl may be particularly useful. Exemplary compounds are commercially available from Lonza as BARDAC 2050, 205M and 2250 from Lonza; Cetylpyridinium halides such as cetylpyridinium chloride available from Merrell labs as Cepacol Chloride; Benzethonium halides and alkyl substituted benzethonium halides such as HYAMINE 1622 and HYAMINE 10× available from Rohm and Haas; octenidine, and the like.

The antiseptics are typically added to the compositions at a concentration of greater than 0.10 wt-%, more preferably greater than 0.25 wt-%, even more preferably greater than 0.5% and most preferably greater than 1.0% by weight, based on the total weight of the composition. Preferably, the concentration is less than 6 wt-%, more preferably less than 4 wt-%, and most preferably less than 3% by weight, based on the total weight of the composition. The pH of aqueous compositions (or the aqueous phase of these compositions) formulated with these antiseptics typically range from 3-9 and most preferably from 3.5-7.

Peroxides

Peroxides, such hydrogen peroxide and benzoyl peroxide, are a useful class of antiseptics. Complexes of peroxides may also be useful, including but not limited to, complexes of hydrogen peroxide with polymers such as polylactams (e.g., polyvinylpyrrolidone (Peroxydone from ISP, Wayne, N.J.)), polycarboxylic acids such s polyacrylic acids (e.g., carbomer type polymer complexes), as well as other polymers that form stable complexes with the peroxide.

Compounds that generate hydrogen peroxide in situ are also desirable. Such compounds include, for example, percarbonates (e.g., sodium carbonate peroxohydrate and other peroxohydrates generally having the formula $(M_2CO_3)_3H_2O$ where M represents the metal or ammonium ion), perborates (e.g., sodium perborate), and urea peroxohydrate, which is also known as urea peroxide or hydrogen peroxide carbamide. These latter compounds generate hydrogen peroxide upon exposure to water and thus may be added to aqueous compositions or added to non-aqueous composition.

Peroxides can easily decompose in the presence of catalysts, alkaline pH, exposure to particles having a rough surface, and tissue peroxidase or catalase. The peroxides should be protected from degradation and preferably stabilized. Hydrogen peroxide is presently the most preferred peroxide for use in the present invention.

A preferred stabilizer for use with peroxides is tin such as sodium stannate. The tin may be present from about 0.1 mg up to about 1.4 mg per liter of peroxide concentrate used. In a preferred embodiment, hydrogen peroxide USP is used to formulate the composition, which is approximately 30% by weight hydrogen peroxide in water. The pH of the composition is preferably less than 7, more preferably less than 6, and most preferably less than 5. Preferred compositions have pH values greater than 2 and preferably greater than about 3 to prevent excessive irritation. The concentration of peroxide is typically added to the formulations in amounts of 0.5% by weight, preferably 1% by weight, and most preferably 2% by weight. In most embodiments, the compounds are added in amounts of no greater than 8 wt-%, more preferably no greater than 6 wt-%, and most preferably no greater than 5 wt-%.

The solubility in both oil and/or water of the peroxide used may affect the selection of the hydrophilic or the hydrophilic component as the vehicle. For example, benzoyl peroxide is oil-soluble, which may be used with a hydrophobic component, such as petrolatum, or an oil-in-water emulsion.

Natural Oil Antiseptics

This class of natural oil antiseptics includes oils and oil extracts from plants such as Tea Tree oil, grape fruit seed extract, Aspidium extract (phloro, lucinol containing extract); barberry extract (berberine chloride); bay sweet extract; bayberry bark extract (myricitrin); cade oil; CAE (available from Ajinomoto, located in Teaneck, N.J.); cajeput oil; caraway oil; cascarilla bark (sold under the tradename ESSENTIAL OIL); cedarleaf oil; chamomille; cinnamon oil; citronella oil; clove oil; German chamomile oil; giant knotweed; lemon balm oil; lemon grass; olive leaf extract (available from Bio Botanica); parsley; patchouli oil; peony root; pine needle oil; PLANSERVATIVE (available from Campo Research); rose geranium oil; rosemary; sage, and the like, as well as mixtures thereof. Particularly preferred are tea tree oil (cajeput oil) and grapefruit seed extract.

These compounds may be relatively water insoluble and thus it may be preferred to formulate these compounds in the presence of a hydrophobic component and/or an emulsifier/surfactant, in an emulsion (water in oil or oil in water), or in a hydrophilic vehicle (e.g., other than water). These compounds are typically added to the formulations at 0.5-8%, preferably 1-6%, and most preferably 2-4% by weight. Significantly higher levels may be required in hydrophobic components that are good solvents for the antiseptics to ensure some of the antiseptic is available to kill the microorganisms. Preferred compositions are formulated free of polyethylene glycol with a MW greater than about 1500 daltons, and more preferably greater than 600 daltons, which may reduce the activity. In most embodiments, the compositions are those based on hydrophobic vehicles (such as petrolatum) with an optional hydrophilic component and/or water in oil emulsions. The pH of compositions formulated with these antiseptics typically range from 3 to 9 and most preferably from 3.5 to 7.

The compositions described herein include one or more antimicrobials (preferably, antiseptics) at a suitable level to produce the desired result. Such compositions preferably include a total amount of antimicrobial (preferably, antiseptic) of at least 0.1 percent by weight (wt-%), more preferably at least 0.25 wt-%, even more preferably at least 0.35 wt-%, even more preferably at least 0.5 wt-%, and even more preferably at least 1, at least 2, or even at least 3 wt-%, based on the total weight of the "ready to use" or "as used" composition. In a preferred embodiment, the antimicrobial(s) are present in a total amount of no greater than 30 wt-%, more preferably no greater than 15 wt-%, even more preferably no greater than 10 wt-%, and even more preferably no greater than 6 wt-%, based on the "ready to use" or "as used" composition. Antimicrobials that are liquids at room temperature, however, may be used as the vehicle and thus present in amounts up to about 99%. For example, many of the antimicrobial lipids which are liquids are room temperature are non-irritating to skin and mucosal tissue and thus may be used as the vehicle. For example, the (C8-C12) fatty acid esters of propylene glycol, 2 ethyl-hexyl glyceryl ether, (C8-C12) branched and straight chain alkyl alcohol esters of lactic acid are all liquids that are potentially useful in very high concentrations. Certain of the antimicrobial lipids that are solids at room temperature can also be used in higher concentrations if mixed with a component that prevents or minimizes crystallization. These "crystallization inhibitors" may include esters, ethers, and glycols that are liquid at room temperature. In other instances, the compositions may include higher concentrations of the antimicrobial agents if they are intended to be diluted prior to use.

The antimicrobials (preferably, antiseptics) of this invention may be used alone or in combination in order to effectively kill microorganisms on tissue. Certain combinations of antimicrobials (preferably, antiseptics) may be particularly useful while others may result in unstable formulations or inactivation of the antimicrobial activity. On the other hand, other antimicrobial combinations may produce an enhancement or synergistic effect.

Certain combinations of antimicrobials may be particularly useful while others may result in unstable formulations or inactivation of the antimicrobial activity. For example, combination of cationic antiseptics, such as biguanides, bisbiguanides, polymeric biguanides, polymeric quaternary ammonium compounds, quaternary ammonium compounds, and silver may be incompatible with allkyl carboxylic acids. On the other hand, other antiseptic combinations may produce a synergistic or enhancing effect. For example, C6 and higher fatty acids may enhance the activity of peroxides as well as the fatty acid monoglycerides antiseptics described below.

Enhancer Component

Compositions described herein preferably include an enhancer (preferably a synergist) to enhance the antimicrobial activity especially against Gram negative bacteria, such as *E. coli* and *Psuedomonas* sp. The chosen enhancer preferably affects the cell envelope of the bacteria. While not bound by theory, it is presently believed that the enhancer functions by allowing the antimicrobial component to more easily enter the cell cytoplasm and/or by facilitating disruption of the cell envelope. The enhancer component may include an alpha-hydroxy acid, a beta-hydroxy acid, other carboxylic acids, a phenolic compound (such as certain antioxidants and parabens), a monohydroxy alcohol, a chelating agent, a glycol ether (i.e., ether glycol), or a sugar and/or sugar alcohol. Various combinations of enhancers can be used if desired.

The alpha-hydroxy acid, beta-hydroxy acid, and other carboxylic acid enhancers are preferably present in their protonated, free acid form. It is not necessary for all of the acidic enhancers to be present in the free acid form; however, the preferred concentrations listed below refer to the amount present in the free acid form. Additional, non-alpha hydroxy acid, betahydroxy acid or other carboxylic acid enhancers, may be added in order to acidify the formulation or buffer it at a pH to maintain antimicrobial activity. Furthermore, the chelator enhancers that include carboxylic acid groups are preferably present with at least one, and more preferably at least two, carboxylic acid groups in their free acid form. The concentrations given below assume this to be the case.

One or more enhancers may be used in the compositions described herein at a suitable level to produce the desired result. In a preferred embodiment, they are present in a total amount greater than 0.01 wt-%, more preferably in an amount greater than 0.1 wt-%, even more preferably in an amount greater than 0.2 wt-%, even more preferably in an amount greater than 0.25 wt-%, and most preferably in an amount greater than 0.4 wt-% based on the total weight of the ready to use composition. In a preferred embodiment, they are present in a total amount of no greater than 20 wt-%, based on the total weight of the ready to use composition. Such concentrations typically apply to alpha-hydroxy acids, beta-hydroxy acids, other carboxylic acids, chelating agents, phenolics, ether glycols, and (C5-C10)monohydroxy alcohols. Generally, higher concentrations are needed for (C1-C4)monohydroxy alcohols, as described in greater detail below.

The alpha-hydroxy acid, beta-hydroxy acid, and other carboxylic acid enhancers, as well as chelators that include carboxylic acid groups, are preferably present in a concentration of no greater than 100 milliMoles per 100 grams of formulated composition. In most embodiments, alpha-hydroxy acid, beta-hydroxy acid, and other carboxylic acid enhancers, as well as chelators that include carboxylic acid groups, are preferably present in a concentration of no greater than 75 milliMoles per 100 grams, more preferably no greater than 50 milliMoles per 100 grams, and most preferably no greater than 25 milliMoles per 100 grams of formulated composition.

The total concentration of the enhancer component relative to the total concentration of the antimicrobial component is preferably within a range of 10:1 to 1:300, and more preferably 5:1 to 1:10, on a weight basis.

An additional consideration when using an enhancer is the solubility and physical stability in the compositions. Many of the enhancers discussed herein are insoluble in preferred hydrophobic components such as petrolatum. It has been found that the addition of a minor amount (typically less than 30 wt-%, preferably less than 20 wt-%, and more preferably less than 12 wt-%) of a hydrophilic component not only helps dissolve and physically stabilize the composition but improves the antimicrobial activity as well. These hydrophilic components are described below.

Alternatively, the enhancer component may be present in excess of the solubility limit provided that the composition is physically stable. This may be achieved by utilizing a sufficiently viscous composition that stratification (e.g., settling or creaming) of the antimicrobial lipid does not appreciably occur.

Alpha-Hydroxy Acids

An alpha-hydroxy acid is typically a compound represented by the formula:

$$R^5(CR^6OH)_n COOH$$

wherein: $R^5$ and $R^6$ are each independently H, a (C1-C8) alkyl group (straight, branched, or cyclic group), a (C6-C12) aryl group, a (C6-C12)aralkyl group, or a (C6-C12)alkaryl group (wherein the alkyl group of the aralkyl or alkaryl is straight, branched, or cyclic), wherein $R^5$ and $R^6$ may be optionally substituted with one or more carboxylic acid groups; and n=1–3, preferably, n=1–2.

Exemplary alpha-hydroxy acids include, but are not limited to, lactic acid, malic acid, citric acid, 2-hydroxybutanoic acid, mandelic acid, gluconic acid, glycolic acid (i.e., alpha-hydroxyethanoic acid), tartaric acid, alpha-hydroxyoctanoic acid, alpha-hydroxycaprylic acid, and salicylic acid, as well as derivatives thereof (e.g., compounds substituted with hydroxyls, phenyl groups, hydroxyphenyl groups, alkyl groups, halogens, as well as combinations thereof). Preferred alpha-hydroxy acids include lactic acid, malic acid, and mandelic acid. These acids may be in D, L, or DL form and may be present as free acid, lactone, or partial salts thereof. All such forms are encompassed by the term "acid." Preferably, the acids are present in the free acid form. In certain preferred embodiments, the alpha-hydroxy acids useful in the compositions described herein are selected from the group consisting of lactic acid, mandelic acid, and malic acid, and mixtures thereof. Other suitable alpha-hydroxy acids are described in U.S. Pat. No. 5,665,776 (Yu).

One or more alpha-hydroxy acids may be used in the compositions described herein at a suitable level to produce the desired result. In a preferred embodiment, they are present in a total amount of at least 0.25 wt-%, more preferably, at least 0.5 wt-%, and even more preferably, at least 1 wt-%, based on the total weight of the ready to use composition. In a preferred embodiment, they are present in a total amount of no greater than 10 wt-%, more preferably, no greater than 5 wt-%, and even more preferably, no greater than 3 wt-%, based on the total weight of the ready to use composition. Higher concentrations may become irritating.

The ratio of alpha-hydroxy acid enhancer to total antimicrobial component is preferably at most 10:1, more preferably at most 5:1, and even more preferably at most 1:1. The ratio of alpha-hydroxy acid enhancer to total antimicrobial component is preferably at least 1:20, more preferably at least 1:12, and even more preferably at least 1:5. Preferably the ratio of alpha-hydroxy acid enhancer to total antimicrobial component is within a range of 1:12 to 1:1.

Beta-Hydroxy Acids

A beta-hydroxy acid is typically a compound represented by the formula:

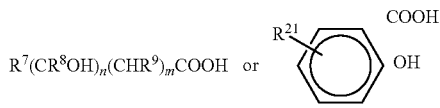

wherein: $R^7$, $R^8$, and $R^9$ are each independently H, a (C1-C8)alkyl group (saturated straight, branched, or cyclic group), a (C6-C12)aryl group, a (C6-C12)aralkyl group, or a (C6-C12)alkaryl group (wherein the alkyl group of the alkaryl or aralkyl is straight, branched, or cyclic), wherein $R^7$ and $R^8$ may be optionally substituted with one or more carboxylic acid groups; m=0 or 1; n=1-3 (preferably, n=1-2); and $R^{21}$ is H, (C1-C4)alkyl or a halogen.

Exemplary beta-hydroxy acids include, but are not limited to, salicylic acid, beta-hydroxybutanoic acid, tropic acid, 4-aminosalicyclic acid, and trethocanic acid. In certain preferred embodiments, the beta-hydroxy acids useful in the compositions described herein are selected from the group consisting of salicylic acid, beta-hydroxybutanoic acid, and mixtures thereof. Other suitable beta-hydroxy acids are described in U.S. Pat. No. 5,665,776 (Yu).

One or more beta-hydroxy acids may be used in the compositions described herein at a suitable level to produce the desired result. In a preferred embodiment, they are present in a total amount of at least 0.1 wt-%, more preferably at least 0.25 wt-%, and even more preferably at least 0.5 wt-%, based on the total weight of the ready to use composition. In a preferred embodiment, they are present in a total amount of no greater than 10 wt-%, more preferably no greater than 5 wt-%, and even more preferably no greater than 3 wt-%, based on the total weight of the ready to use composition. Higher concentrations may become irritating.

The ratio of beta-hydroxy acid enhancer to total antimicrobial component is preferably at most 10:1, more preferably at most 5:1, and even more preferably at most 1:1. The ratio of beta-hydroxy acid enhancer to total antimicrobial component is preferably at least 1:20, more preferably at least 1:15, and even more preferably at least 1:10. Preferably the ratio of beta-hydroxy acid enhancer to total antimicrobial component is within a range of 1:15 to 1:1.

In systems with low concentrations of water, or that are essentially free of water, transesterification or esterification may be the principle route of loss of carboxylic acid containing enhancers. Thus, certain alpha-hydroxy acids (AHA) and beta-hydroxy acids (BHA) are particularly preferred since these are believed to be less likely to transesterify or esterify with other components in the composition such as, for example, an ester antimicrobial lipid or other ester, by reaction of the hydroxyl group of the AHA or BHA. For example, salicylic acid may be particularly preferred in certain formulations since the phenolic hydroxyl group is a much more acidic alcohol and thus much less likely to react than an aliphatic hydroxyl group. Other particularly preferred compounds in anhydrous or low-water content formulations include lactic, mandelic, malic, citric, tartaric, and glycolic acid. Benzoic acid and substituted benzoic acids that do not include a hydroxyl group, while not hydroxyl acids, are also preferred due to a reduced tendency to form ester groups.

Other Carboxylic Acids

Carboxylic acids other than alpha- and beta-carboxylic acids are suitable for use in the enhancer component. These include alkyl, aryl, aralkyl, or alkaryl carboxylic acids typically having equal to or less than 16, and often equal to or less than 12, carbon atoms. A preferred class of these can be represented by the following formula:

$$R^{10}(CR^{11}_2)_n COOH$$

wherein: $R^{10}$ and $R^{11}$ are each independently H or a (C1-C4)alkyl group (which can be a straight, branched, or cyclic group), a (C6-C12)aryl group, a (C6-C16) group containing both aryl groups and alkyl groups (which can be a straight, branched, or cyclic group), wherein $R^{10}$ and $R^{11}$ may be optionally substituted with one or more carboxylic acid groups; and n=0–3, preferably, n=0–2. Preferably, the carboxylic acid is a (C1-C4)alkyl carboxylic acid, a (C6-C16) aralkyl carboxylic acid, or a (C6-C16)alkaryl carboxylic acid. Exemplary acids include, but are not limited to, acetic acid, propionic acid, benzoic acid, benzylic acid, nonylbenzoic acid, p-hydroxybenzoic acid, retinoic acid, and the like. Particularly preferred is benzoic acid.

One or more carboxylic acids (other than alpha- or beta-hydroxy acids) may be used in the compositions described herein at a suitable level to produce the desired result. In a preferred embodiment, they are present in a total amount of at least 0.1 wt-%, more preferably at least 0.25 wt-%, even more preferably at least 0.5 wt-%, and most preferably at least 1 wt-%, based on the ready to use concentration composition. In a preferred embodiment, they are present in a total amount of no greater than 10 wt-%, more preferably no greater than 5 wt-%, and even more preferably no greater than 3 wt-%, based on the ready to use composition.

The ratio of the total concentration of carboxylic acids (other than alpha- or beta-hydroxy acids) to the total concentration of the antimicrobial component is preferably within a range of 10:1 to 1:100, and more preferably 2:1 to 1:10, on a weight basis.

Chelators

A chelating agent (i.e., chelator) is typically (but not necessarily) an organic compound capable of multiple coordination sites with a metal ion in solution. Typically these chelating agents are polyanionic compounds and coordinate best with polyvalent metal ions. Exemplary chelating agents include, but are not limited to, ethylene diamine tetraacetic acid (EDTA) and salts thereof (e.g., EDTA(Na)$_2$, EDTA(Na)$_4$, EDTA(Ca), EDTA(K)$_2$), sodium acid pyrophosphate, acidic sodium hexametaphosphate, adipic acid, succinic acid, polyphosphoric acid, sodium acid pyrophosphate, sodium hexametaphosphate, acidified sodium hexametaphosphate, nitrilotris(methylenephosphonic acid), diethylenetriaminepentaacetic acid, ethylenebis(oxyethyleneni-trilo)tetraacetic acid, glycolether diaminetetraacetic acid, ethyleneglycol-O,O'bis(2-aminoethyl)-N,N, N',N'-tetraacetic acid (EGTA), N-(2-hydroxyethyl)ethylenediamine-N,N',N'-triacetic acid trisodium salt (HETA), polyethylene glycol diaminetetraacetic acid, 1-hydroxyethylene, 1,1-diphosphonic acid (HEDP), and diethylenetriaminepenta-(methylenephosphonic acid). Any of these chelating agents may also be used in their partial or complete salt form. Certain carboxylic acids, particularly the alpha-hydroxy acids and beta-hydroxy acids, can also function as chelators, e.g., malic acid, citric, and tartaric acid.

Also included as chelators are compounds highly specific for binding ferrous and/or ferric ion such as siderophores, and iron binding proteins. Iron binding proteins include, for example, lactoferrin, and transferrin. Siderophores include, for example, enterochlin, enterobactin, vibriobactin, anguibactin, pyochelin, pyoverdin, and aerobactin.

In certain preferred embodiments, the chelating agents useful in the compositions described herein include those selected from the group consisting of ethylenediaminetetraacetic acid, and salts thereof, succinic acid, tartaric acid and mixtures thereof. Preferably, either the free acid or the mono- or di-salt form of EDTA is used.

One or more chelating agents may be used in the compositions described herein at a suitable level to produce the desired result. In a preferred embodiment, they are present in a total amount of at least 0.01 wt-%, more preferably at least 0.05 wt-%, even more preferably at least 0.1 wt-%, and even more preferably at least 1 wt-%, based on the weight of the ready to use composition. In a preferred embodiment, they are present in a total amount of no greater than 10 wt-%, more preferably no greater than 5 wt-%, and even more preferably no greater than 1 wt-%, based on the weight of the ready to use composition.

The ratio of the total concentration of chelating agents (other than alpha- or beta-hydroxy acids) to the total concentration of the antimicrobial component is preferably within a range of 10:1 to 1:100, and more preferably 1:1 to 1:10, on a weight basis.

Phenolic Enhancer Compounds

A phenolic compound (i.e., a phenol or phenol derivative) enhancer is typically a compound having the following general structure:

wherein: m is 0 to 3 (especially 1 to 3), n is 1 to 3 (especially 1 to 2), each $R^{12}$ independently is alkyl or alkenyl of up to 12 carbon atoms (especially up to 8 carbon atoms) optionally substituted with O in or on the chain (e.g., as a carbonyl group) or OH on the chain, and each $R^{13}$ independently is H or alkyl or alkenyl of up to 8 carbon atoms (especially up to 6 carbon atoms) optionally substituted with O in or on the chain (e.g., as a carbonyl group) or OH on the chain, but where $R^{13}$ is H, n preferably is 1 or 2.

Examples of phenolic enhancers include, but are not limited to, butylated hydroxy anisole, e.g., 3(2)-tert-butyl-4-methoxyphenol (BHA), 2,6-di-tert-butyl-4-methylphenol (BHT), 3,5-di-tert-butyl-4-hydroxybenzylphenol, 2,6-di-tert-4-hexylphenol, 2,6-di-tert-4-octylphenol, 2,6-di-tert-4-decylphenol, 2,6-di-tert-butyl-4-ethylphenol, 2,6-di-tert-4-butylphenol, 2,5-di-tert-butylphenol, 3,5-di-tert-butylphenol, 4,6-di-tert-butyl-resorcinol, methyl paraben (4-hydroxybenzoic acid methyl ester), ethyl paraben, propyl paraben, butyl paraben, as well as combinations thereof. A preferred group of the phenolic compounds is the phenol species having the general structure shown above where $R^{13}$=H and where $R^{12}$ is alkyl or alkenyl of up to 8 carbon atoms, and n is 1, 2, or 3, especially where at least one $R^{12}$ is butyl and particularly tert-butyl, and especially the non-toxic members thereof. Some of the preferred phenolic synergists are BHA, BHT, methyl paraben, ethyl paraben, propyl paraben, and butyl paraben as well as combinations of these.

One or more phenolic compounds may be used in the compositions described herein at a suitable level to produce the desired result. The concentrations of the phenolic compounds in medical-grade compositions may vary widely, but as little as 0.001 wt-%, based on the total weight of the composition, can be effective when the above-described esters are present within the above-noted ranges. In a preferred embodiment, they are present in a total amount of at least 0.01 wt-%, more preferably at least 0.10 wt-%, and even more preferably at least 0.25 wt-%, based on the ready to use composition. In a preferred embodiment, they are present in a total amount of no greater than 8 wt-%, more preferably no greater than 4 wt-%, and even more preferably no greater than 2 wt-%, based on the ready to use composition.

It is preferred that the ratio of the total phenolic concentration to the total concentration of the antimicrobial component be within a range of 10:1 to 1:300, and more preferably within a range of 1:1 to 1:10, on a weight basis.

The above-noted concentrations of the phenolics are normally observed unless concentrated formulations for subsequent dilution are intended. On the other hand, the minimum concentration of the phenolics and the antimicrobial components to provide an antimicrobial effect will vary with the particular application.

Monohydroxy Alcohols

An additional enhancer class includes monohydroxy alcohols having 1-10 carbon atoms. This includes the lower (i.e., C1-C4) monohydroxy alcohols (e.g., methanol, ethanol, isopropanol, and butanol) as well as longer chain (i.e., C5-C10) monohydroxy alcohols (e.g., isobutanol, t-butanol, octanol, and decanol). Other useful alcohols include benzyl alcohol and menthol. In certain preferred embodiments, the alcohols useful in the compositions described herein are selected from the group consisting of methanol, ethanol, isopropyl alcohol, and mixtures thereof.

One or more alcohols may be used in the compositions described herein at a suitable level to produce the desired result. In a preferred embodiment, the short chain (i.e., C1-C4) alcohols are present in a total amount of at least 10 wt-%, even more preferably at least 15 wt-%, even more preferably at least 20 wt-%, and even more preferably at least 25 wt-%, based on the total weight of the ready to use composition.

In a preferred embodiment, the (C1-C4)alcohols are present in a total amount of no greater than 90 wt-%, more preferably no greater than 70 wt-%, even more preferably no greater than 60 wt-%, and even more preferably no greater than 50 wt-%, based on the total weight of the ready to use composition.

For certain applications, lower alcohols may not be preferred due to the strong odor and potential for stinging and irritation. This can occur especially at higher levels. In applications where stinging or burning is a concern, the concentration of (C1-C4)alcohols is preferably less than 20 wt-%, more preferably less than 15 wt-%.

In another preferred embodiment longer chain (i.e., C5-C10)alcohols are present in a total amount of at least 0.1 wt-%, more preferably at least 0.25 wt-%, and even more preferably at least 0.5 wt-%, and most preferably at least 1.0%, based on the ready to use composition. In a preferred embodiment, the (C5-C10)alcohols are present in a total amount of no greater than 10 wt-%, more preferably no greater than 5 wt-%, and even more preferably no greater than 2 wt-%, based on the total weight of the ready to use composition.

Ether Glycols

An additional enhancer class includes ether glycols (also referred to as glycol ethers). Exemplary ether glycols include those of the formula:

R'—O—(CH$_2$CHR"O)$_n$(CH$_2$CHR"O)H wherein R'=H, a (C1-C8)alkyl, a (C6-C12)aryl group, a (C6-C12)aralkyl group, or a (C6-C12)alkaryl group; and each R" is independently =H, methyl, or ethyl; and n=0-5, preferably 1-3. Examples include 2-phenoxyethanol, dipropylene glycol, triethylene glycol, the line of products available under the trade designation DOWANOL DB (di(ethylene glycol) butyl ether), DOWANOL DPM (di(propylene glycol)monomethyl ether), and DOWANOL TPnB (tri(propylene glycol) monobutyl ether), as well as many others available from Dow Chemical, Midland, Mich.

One or more ether glycols may be used in the compositions described herein at a suitable level to produce the desired result. In a preferred embodiment, they are present in a total amount of at least 0.01 wt-%, based on the total weight of the ready to use composition. In a preferred embodiment, they are present in a total amount of no greater than 20 wt-%, based on the total weight of the ready to use composition.

Sugars and Sugar Alcohols

Suitable sugars can include both monosaccharides and disaccharides. Suitable monosaccharides include, but are not limited to, mannose, xylose, maltose, sorbose, and their corresponding sugar alcohols mannitol, xylitol, maltitol, and sorbitol. In certain preferred embodiments, the sugar is selected from the group consisting of mannose, xylose, mannitol, xylitol, and combinations thereof. In certain embodiments, the sugar is a disaccharide of xylitol and glucose. For disaccharides, at least one of the sugars is preferably one of the suitable monosaccharides listed herein. The second sugar unit may be selected from any suitable sugar commonly used in food products, such as but not limited to, glucose, fructose, mannose, xylose, galacose, sorbose, and sorbitol.

One or more sugars or sugar alcohols may be used in the compositions described herein at a suitable level to produce the desired result. In a preferred embodiment, they are present in a total amount of at least 0.5 wt-% and preferably at least 1.0% based on the total weight of the ready to use composition. In a preferred embodiment, they are present in a total amount of no greater than 20 wt-%, based on the total weight of the ready to use composition.

Surfactant Component

Compositions described herein can optionally include at least one surfactant (i.e., a surfactant component) to emulsify the composition and to help wet the surface and/or to aid in contacting the microorganisms. The surface to be wetting may be the tissue and/or an instrument to be inserted into the body. As used herein the term "surfactant" means an amphiphile (a molecule possessing both polar and nonpolar regions which are covalently bound) capable of reducing the surface tension of water and/or the interfacial tension between water and an immiscible liquid. The term is meant to include soaps, detergents, emulsifiers, surface active agents, and the like. The surfactant can be cationic, anionic, nonionic, or amphoteric. This includes a wide variety of conventional surfactants. Combinations of various surfactants can be used if desired.

Certain ethoxylated surfactants can reduce or eliminate the antimicrobial efficacy of at least some antimicrobial lipid components. For example, some of the antimicrobial lipid components may be inactivated by certain polyethoxylated surfactants. The exact mechanism of this is not known and not all ethoxylated surfactants display this negative effect. For example, poloxamer (polyethylene oxide/polypropylene oxide) surfactants have been shown to be compatible with the antimicrobial lipid component, but ethoxylated sorbitan fatty acid esters such as those sold under the trade name TWEEN by ICI have not been compatible. It should be noted that these are broad generalizations and the activity could be formulation dependent. One skilled in the art can easily determine compatibility of a surfactant by making the formulation and testing for antimicrobial activity as described in the Examples Section.

It should be noted that certain antimicrobials are amphiphiles and may be surface active. For example, certain antimicrobial alkyl monoglycerides described herein are surface active. For certain embodiments of the invention, the antimicrobial component is considered distinct from a "surfactant" component. Furthermore, certain iodophors may be produced by complexing iodine with a surfactant such as a polyethoxylated surfactant, e.g., polyethoxylated nonylphenol. For the purposes of this invention, the surfactant incorporated into the iodophor is not considered a surfactant, but is part of the antimicrobial component.

Preferred non-ionic polyethoxylated surfactants are those that have an HLB (i.e., hydrophile to lipophile balance) of at least 4 and more preferably at least 8. Even more preferred surfactants have an HLB of at least 12. Most preferred surfactants have an HLB of at least 15; however, lower HLB surfactants are still useful in compositions described herein.

Preferred surfactants also have a critical micelle concentration greater than $1 \times 10^{-4}$ moles/liter, preferably greater than $1 \times 10^{-3}$ moles/liter and most preferably greater than $2 \times 10^{-3}$ moles/liter. Other preferred surfactants do not form micelles such as the POLOXAMER surfactants.

Examples of the various classes of surfactants are described below. In certain preferred embodiments, the surfactants useful in the compositions described herein are selected from the group consisting of sulfonate surfactants, sulfate surfactants, phosphonate surfactants, phosphate surfactants, poloxamer (polyethylene oxide/polypropylene oxide block copolymers) surfactants, cationic surfactants, and mixtures thereof. In certain more preferred embodiments, the surfactants useful in the compositions described herein are selected from the group consisting of sulfonate surfactants, sulfate surfactants, phosphate surfactants, and mixtures thereof.

One or more surfactants may be used in the compositions described herein at a suitable level to produce the desired result. In a preferred embodiment, they are present in a total amount of at least 0.1 wt-%, more preferably at least 0.5 wt-%, and even more preferably at least 1.0 wt-%, based on the total weight of the ready to use composition. Many of the compositions described herein are intended to be left on tissue for the desired indication, e.g., decolonizing urethral tissue. Therefore, in order to avoid irritation in a preferred embodiment, they are present in a total amount of no greater than 10 wt-%, more preferably no greater than 5 wt-%, even more preferably no greater than 3 wt-%, and even more preferably no greater than 2 wt-%, based on the total weight of the ready to use composition. The ratio of the total concentration of surfactant to the total concentration of the antimicrobial component is preferably within a range of 5:1 to 1:100, more preferably 3:1 to 1:10, and most preferably 2:1 to 1:3, on a weight basis.

Cationic Surfactants

Exemplary cationic surfactants include, but are not limited to, salts of optionally polyoxyalkylenated primary, secondary, or tertiary fatty amines; quaternary ammonium salts such as tetraalkylammonium, alkylamidoalkyltrialkylammonium, trialkylbenzylammonium, trialkylhydroxyalkylammonium, or alkylpyridinium halides (preferably chlorides or bromides) as well as other anionic counterions, such as but not limited to, alkyl sulfates, such as but not limited to, methosulfate and ethosulfate; imidazoline derivatives; amine oxides of a cationic nature (e.g., at an acidic pH).

In certain preferred embodiments, the cationic surfactants useful in the compositions described herein are selected from the group consisting of tetralkyl ammonium, trialkylbenzylammonium, and alkylpyridinium halides as well as other anionic counterions, such as but not limited to, (C1-C4)allyl sulfates, such as but not limited to, methosulfate and ethosulfate, and mixtures thereof.

Amine Oxide Surfactants

Also particularly preferred are amine oxide surfactants, which can be cationic or nonionic depending on the pH (e.g., cationic at lower pH and nonionic at higher pH). Amine oxide surfactants including alkyl and alkylamidoalkyldialkylamine oxides of the following formula:

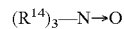

$(R^{14})_3$—N→O wherein $R^4$ is a (C1-C30)alkyl group (preferably a (C1-C14) alkyl group) or a (C6-C18)aralklyl or alkaryl group, wherein any of these groups can be optionally substituted in or on the chain by N—, O—, or S-containing groups such as amide, ester, hydroxyl, and the like. Each $R^{14}$ may be the same or different provided at least one $R^{14}$ group includes at least eight carbons. Optionally, the $R^{14}$ groups can be joined to form a heterocyclic ring with the nitrogen to form surfactants such as amine oxides of alkyl morpholine, alkyl piperazine, and the like. Preferably two $R^{14}$ groups are methyl and one $R^{14}$ group is a (C12-C16)alkyl or alkylamidopropyl group.

Examples of amine oxide surfactants include those commercially available under the trade designations AMMONYX LO, LMDO, and CO, which are lauryldimethylamine oxide, laurylamidopropyldimethylamine oxide, and cetyl amine oxide, all from Stepan Company. Note that the amine oxide surfactants behave as cationic surfactants at lower pH values where they become protonated. The amine oxide surfactants may be used in their protonated or unprotonated form.

Anionic Surfactants

Exemplary anionic surfactants include, but are not limited to, sarcosinates, glutamates, alkyl sulfates, sodium or potassium alkyleth sulfates, ammonium alkyleth sulfates, ammonium laureth-n-sulfates, laureth-n-sulfates, isethionates, glycerylether sulfonates, sulfosuccinates, alkylglyceryl ether sulfonates, alkyl phosphates, aralkyl phosphates, alkylphosphonates, and aralkylphosphonates. These anionic surfactants may have a metal or organic ammonium counterion. In certain preferred embodiments, the anionic surfactants useful in the compositions described herein are selected from the group consisting of:

1. Sulfonates and Sulfates. Suitable anionic surfactants include sulfonates and sulfates such as alkyl sulfates, alkylether sulfates, alkyl sulfonates, alkylether sulfonates, alkylbenzene sulfonates, alkylbenzene ether sulfates, alkylsulfoacetates, secondary alkane sulfonates, secondary alkylsulfates, and the like. Many of these can be represented by the formulas:

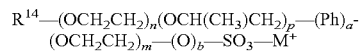

$R^{14}$—$(OCH_2CH_2)_n(OCH(CH_3)CH_2)_p$—$(Ph)_a$-$(OCH_2CH_2)_m$—$(O)_b$—$SO_3$—$M^+$ and

$R^{14}$—$CH[SO_3\text{-}M^+]$—$R^{15}$ wherein: a and b=0 or 1; n, p, and m=0-100 (preferably 0-20, and more preferably 0-10); $R^{14}$ is defined as above provided at least one $R^{14}$ or $R^{15}$ is at least C8; $R^{15}$ is a (C1-C12)alkyl group (saturated straight, branched, or cyclic group) that may be optionally substituted by N, O, or S atoms or hydroxyl, carboxyl, amide, or amine groups; Ph phenyl; and M is a cationic counterion such as H, Na, K, Li, ammonium, or a protonated tertiary amine such as triethanolamine or a quaternary ammonium group.

In the formula above, the ethylene oxide groups (i.e., the "n" and "m" groups) and propylene oxide groups (i.e., the "p" groups) can occur in reverse order as well as in a random, sequential, or block arrangement. Preferably for this class, $R^{14}$ includes an alkylamide group such as $R^{16}$—C(O)N(CH$_3$)CH$_2$CH$_2$— as well as ester groups such as —OC(O)—CH$_2$— wherein $R^{16}$ is a (C8-C22)alkyl group (branched, straight, or cyclic group). Examples include, but are not limited to: alkyl ether sulfonates such as lauryl ether sulfates such as POLYSTEP B12 (n=3-4, M=sodium) and B22 (n=12, M=ammonium) available from Stepan Company, Northfield, Ill. and sodium methyl taurate (available under the trade designation NIKKOL CMT30 from Nikko Chemicals Co., Tokyo, Japan); secondary alkane sulfonates such as Hostapur SAS which is a Sodium (C14-C17)secondary alkane sulfonates (alpha-olefin sulfonates) available from Clariant Corp., Charlotte, N.C.; methyl-2-sulfoalkyl esters such as sodium methyl-2-sulfo(C12-16)ester and disodium 2-sulfo(C12-C16)fatty acid available from Stepan Company under the trade designation ALPHASTEP PC-48; alkylsulfoacetates and alkylsulfosuccinates available as sodium laurylsulfoacetate (under the trade designation LANTHANOL LAL) and disodiumlaurethsulfosuccinate (STEPANMILD SL3), both from Stepan Company; alkylsulfates such as ammoniumlauryl sulfate commercially available under the trade designation STEPANOL AM from Stepan Company; dialkylsulfosuccinates such as dioctylsodiumsulfosuccinate available as Aerosol OT from Cytec Industries. Hydrotropes such as DOWFAX hydrotrope from Dow chemical or other diphenyl oxide surfactants may also be used.

2. Phosphates and Phosphonates. Suitable anionic surfactants also include phosphates such as alkyl phosphates, alkylether phosphates, aralkylphosphates, and aralkylether phosphates. Many may be represented by the formula:

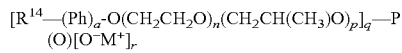

wherein: Ph, $R^{14}$, a, n, p, and M are defined above; r is 0-2; and q=1-3; with the proviso that when q=1, r=2, and when q=2, r=1, and when q=3, r=0. As above, the ethylene oxide groups (i.e., the "n" groups) and propylene oxide groups (i.e., the "p" groups) can occur in reverse order as well as in a random, sequential, or block arrangement. Examples include a mixture of mono-, di- and tri-(alkyltetraglycolether)-o-phosphoric acid esters generally referred to as trilaureth-4-phosphate commercially available under the trade designation HOSTAPHAT 340KL from Clariant Corp., as well as PPG-5 ceteth 10 phosphate available under the trade designation CRODAPHOS SG from Croda Inc., Parsipanny, N.J., and mixtures thereof.

Amphoteric Surfactants

Surfactants of the amphoteric type include surfactants having tertiary amine groups, which may be protonated, as well as quaternary amine containing zwitterionic surfactants. Those that have been particularly useful include:

1. Ammonium Carboxylate Amphoterics. This class of surfactants can be represented by the following formula:

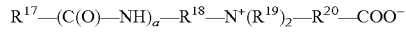

wherein: a=0 or 1; $R^{17}$ is a (C7-C21)alkyl group (saturated straight, branched, or cyclic group), a (C6-C22)aryl group, or a (C6-C22)aralkyl or alkaryl group (saturated straight, branched, or cyclic alkyl group), wherein $R^{17}$ may be optionally substituted with one or more N, O, or S atoms, or one or more hydroxyl, carboxyl, amide, or amine groups; $R^{19}$ is H or a (C1-C8)alkyl group (saturated straight, branched, or cyclic group), wherein $R^{19}$ may be optionally substituted with one or more N, O, or S atoms, or one or more hydroxyl, carboxyl, amine groups, a (C6-C9)aryl group, or a (C6-C9)aralkyl or alkaryl group; and $R^{18}$ and $R^{20}$ are each independently a (C1-C10)alkylene group that may be the same or different and may be optionally substituted with one or more N, O, or S atoms, or one or more hydroxyl or amine groups.

More preferably, in the formula above, $R^{17}$ is a (C1-C18) alkyl group, $R^{19}$ is a (C1-C2)alkyl group preferably substituted with a methyl or benzyl group and most preferably with a methyl group. When $R^{19}$ is H it is understood that the surfactant at higher pH values could exist as a tertiary amine with a cationic counterion such as Na, K, Li, or a quaternary amine group.

Examples of such amphoteric surfactants include, but are not limited to: certain betaines such as cocobetaine and cocamidopropyl betaine (commercially available under the trade designations MACKAM CB-35 and MACKAM L from McIntyre Group Ltd., University Park, Ill.); monoacetates such as sodium lauroamphoacetate; diacetates such as disodium lauroamphoacetate; amino- and alkylamino-propionates such as lauraminopropionic acid (commercially available under the trade designations MACKAM 1L, MACKAM 2L, and MACKAM 151L, respectively, from McIntyre Group Ltd.).

2. Ammonium Sulfonate Amphoterics. This class of amphoteric surfactants are often referred to as "sultaines" or "sulfobetaines" and can be represented by the following formula

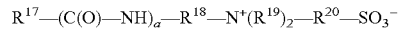

wherein $R^{17}$-$R^{20}$ and "a" are defined above. Examples include cocamidopropyl-hydroxysultaine (commercially available as MACKAM 50-SB from McIntyre Group Ltd.). The sulfoamphoterics may be preferred over the carboxylate amphoterics since the sulfonate group will remain ionized at much lower pH values.

Nonionic Surfactants

Exemplary nonionic surfactants include, but are not limited to, alkyl glucosides, alkyl polyglucosides, polyhydroxy fatty acid amides, sucrose esters, esters of fatty acids and polyhydric alcohols, fatty acid alkanolamides, ethoxylated fatty acids, ethoxylated aliphatic acids, ethoxylated fatty alcohols (e.g., octyl phenoxy polyethoxyethanol available under the trade name TRITON X-100 and nonyl phenoxy poly(ethyleneoxy)ethanol available under the trade name NONIDET P-40, both from Sigma, St. Louis, Mo.), ethoxylated and/or propoxylated aliphatic alcohols (e.g., that available under the trade name BRIJ from ICI, Wilmington, Del.), ethoxylated glycerides, ethoxylated/propoxylated block copolymers such as PLURONIC and TETRONIC surfactants available from BASF, ethoxylated cyclic ether adducts, ethoxylated amide and imidazoline adducts, ethoxylated amine adducts, ethoxylated mercaptan adducts, ethoxylated condensates with alkyl phenols, ethoxylated nitrogen-based hydrophobes, ethoxylated polyoxypropylenes, polymeric silicones, fluorinated surfactants (e.g., those available under the trade names FLUORAD-FS 300 from 3M Co., St. Paul, Minn., and ZONYL from Dupont de Nemours Co., Wilmington, Del.), and polymerizable (reactive) surfactants (e.g., SAM 211 (alkylene polyalkoxy sulfate) surfactant available under the trade name MAZON from PPG Industries, Inc., Pittsburgh, Pa.). In certain preferred embodiments, the nonionic surfactants useful in the compositions described herein are selected from the group consisting of Poloxamers such as PLURONIC from BASF, sorbitan fatty acid esters, and mixtures thereof.

Hydrophilic Component

Compositions described herein can include a hydrophilic or water-soluble component to help solubilize and/or physically stabilize the enhancer component in the composition and/or to enhance the antimicrobial efficacy and/or the speed of antimicrobial efficacy. Incorporation of a sufficient amount of hydrophilic component in hydrophobic ointments can increase the antimicrobial activity both in terms of speed of kill and extent of kill. While not intended to be bound by theory, the incorporation of the hydrophilic component may allow more of the antimicrobial component to be available at the surface or to more rapidly diffuse to the surface of the ointment during use. This is especially true for antimicrobials that are at least partially soluble in the hydrophilic component. The hydrophilic component may also help the diffusion of antimicrobials with poor water solubility into the tissue. This may help eradicate microorganisms from tissue that is heavily colonized or colonized with biofilm and/or microorganisms harboring beneath the surface of the tissue or even within mammalian cells.

In general, the ratio of total hydrophilic component to total hydrophobic component (water insoluble ingredients) is at least 5:95 weight ratio (wt/wt), preferably at least 10:90 wt/wt, more preferably at least 15:85 wt/wt, and even more preferably at least 20:80 wt/wt. Levels as high as 30:70, 40:60, and 50:50 wt/wt of total hydrophilic component to total hydrophobic component (water insoluble ingredients) or higher may be appropriate for certain compositions.

Certain compositions may be solutions, emulsions (one liquid/gel/paste dispersed in another liquid/gel/paste), dispersions (solid in liquid/paste/gel), or combinations thereof.

A hydrophilic material is typically a compound that has a solubility in water of at least 7 wt-%, preferably at least 10 wt-%, more preferably at least 20 wt-%, even more preferably at least 25 wt-%, and even more preferably at least 40 wt-%, at 23° C. Most preferably, a hydrophilic component is infinitely miscible with water at 23° C.

Exemplary hydrophilic components include, but are not limited to, water, polyhydric alcohols, lower alkyl ethers (i.e., having a sufficiently small number of carbon atoms to meet the solubility limit above), N-methylpyrrolidone, alkyl esters (i.e., having a sufficiently small number of carbon atoms to meet the solubility limit above), and the lower monohydroxy alcohols discussed above as enhancers, as well as combinations thereof. Thus, a lower monohydroxy alcohol can function as both a hydrophilic compound and an enhancer. Preferably, the hydrophilic components include polyhydric alcohols, lower alkyl ethers, and water soluble or water dispersible esters. The water soluble or water dispersible esters are typically but not always short chain (i.e., C2-C6)alkyl esters of monofunctional and polyhydric alcohols. More preferably, the hydrophilic components include polyhydric alcohols.

Suitable polyhydric alcohols (i.e., organic compounds having more than one hydroxyl group) have a molecular weight of less than 500, preferably less than 400, and more preferably less than 200. Examples of polyhydric alcohols include, but are not limited to, glycerol, propylene glycol, dipropylene glycol, tripropylene glycol, polypropylene glycol, polyethylene glycol, diethylene glycol, pentaerythritol, trimethylolpropane, trimethylolethane, trimethylolbutane, sorbitol, mannitol, xylitol, pantothenol, ethylene glycol adducts of polyhydric alcohol, propylene oxide adducts of polyhydric alcohol, 1,3-butanediol, dipropylene glycol, diglycerine, polyglycerine, erythritol, sorbitan, sugars (e.g., sucrose, glucose, fructose, mannose, xylose, saccharose, trehalose), sugar alcohols, and the like. Certain preferred polyhydric alcohols include glycols (i.e., those containing two hydroxyl groups), glycerin, and propylene glycol. Certain other preferred polyhydric alcohols include sucrose, xylitol, mannitol, and sorbitol.

Ethers include materials such as dimethylisosorbide, polyethylene glycol and methoxypolyethylene glycols, block and random copolymers of ethylene oxide and propylene oxide, and laureth-4. Alkyl esters include triacetin, methyl acetate, methyl lactate, ethyl lactate esters, esters of polyethoxylated glycols, and combinations thereof.

Water dispersible hydrophilic components include compounds that are solid, liquid, gel, or wax-like at room temperature but, in particular, those water dispersible hydrophilic vehicles that are liquids, gels, or ointments at room temperature are particularly preferred. Preferred dispersible vehicles include typically amphipathic compounds such as polyalkoxylated ethers and esters. For example, particularly preferred components include, polyethoxylated castor oil (or hydrogenated castor oil), polyethoxylated esters or ethers of saturated or unsaturated fatty alcohols such as PEG 6 oleate (oleth-6), PEG 8 dioleate, and the like. Also included in this group are mixed alkoxylated polymers. For example, water dispersible poloxamers, reverse poloxamers, random and block copolymers of ethylene oxide and propylene oxide initiated onto any glycol having 2-6 alcohol groups, polyurethane polymers of polypropylene glycol or polyethylene glycol (PEG), PEG esters of fatty acids, polyethoxylated polyhydroxyfunctional glycol esters such as polyethoxylated glycerin mono-, di-, and tri-esters, sorbitan mono-, di-, and tri-esters, and polyglycerin fatty acid esters. In some embodiments the dispersible vehicle may be the antimicrobial component. For example, a PEG 3 monoglyceride or PEG 5 propylene glycol fatty acid ester may have antimicrobial activity and can also function as the vehicle. In most embodiments, the water content is less than 20%, preferably less than 10%, and more preferably less than 5% by weight of the composition.

In certain preferred embodiments, the hydrophilic components useful in the compositions described herein include those selected from the group consisting of polyhydric alcohols, and in particular glycerin and propylene glycol, and mixtures thereof. Most preferably, the hydrophilic component is selected to match the polyhydric alcohol portion of any fatty acid monoester of a polyhydric alcohol antimicrobial present. For example, if the antimicrobial agent was glycerolmonolaurate (monolaurin) the most preferred hydrophilic component is glycerin. In this manner, any transesterification reaction that may occur with the carrier solvent does not produce an undesirable by-product. If there are other components in the composition that may esterify with hydroxylfunctional hydrophilic components, conditions are selected to minimize this occurrence. For example, the components are not heated together for extended periods of time, and/or the pH is close to neutral if possible, etc.

One or more hydrophilic materials may be used in the compositions described herein at a suitable level to produce the desired result. In certain preferred embodiments that also include the hydrophobic component as the primary component (i.e., the component used in the greatest amount and referred to as a "vehicle"), the hydrophilic component is present in a total amount of at least 0.1%, preferably at least 1 wt-%, more preferably at least 4 wt-%, and even more preferably at least 8 wt-%, based on the weight of the ready to use composition. In certain embodiments, for example, when faster rate of kill is desired, higher levels of hydrophilic component may be employed. In these cases the hydrophilic component is present in a total amount of at least 10 wt-%, more preferably at least 20 wt-%, and even more preferably at least 25 wt-%.

In a preferred embodiment, the hydrophilic component is present in a total amount of no greater than 70 wt-%, preferably no greater than 60 wt-%, more preferably no greater than 40 wt-%, and even more preferably no greater than 30 wt-%, based on the ready to use composition. When the hydrophilic component is present in the greatest amount it is referred to as a "vehicle."

For certain applications, it may be desirable to formulate the antimicrobial component in compositions including a hydrophilic component vehicle that is thickened with soluble, swellable, or insoluble organic polymeric thickeners or inorganic thickeners such as silica, fumed silica, precipitated silica, silica aerogel and carbon black, and the like; other particle fillers such as calcium carbonate, magnesium carbonate, kaolin, talc, titanium dioxide, aluminum silicate, diatomaceous earth, ferric oxide and zinc oxide, clays, and the like; ceramic microspheres or glass microbubbles; ceramic microspheres such as those available under the tradenames ZEOSPHERES or Z-LIGHT from 3M Company, St. Paul, Minn. The above fillers can be used alone or in combination.

If water is used in certain embodiments, it is preferably present in an amount of less than 20%, preferably less than 10 wt-%, more preferably less than 5 wt-%, even more preferably less than 2 wt-%, and even more preferably less than 1 wt-%, based on the ready to use composition. This helps the chemical stability of the compositions and may reduce irritation. For certain other embodiments, water can be used in a much greater amount, and can even be the primary component, as long as the composition is highly viscous. Preferably, such highly viscous compositions have a viscosity of at least 500 centipoise (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). The viscosity can be measured as described below in the Viscosity Test. Most preferred compositions meet these viscosity values even after heating to 32° C. or even 35° C. or as high as 37° C. to ensure when in contact with mammalian tissue the compositions remain substantive.

In some embodiments of the present invention, the compositions have a viscosity of at least 20 cps, preferably at least 100 cps, when measured by the Viscosity Test described herein. Higher viscosities are preferred to reduce migration as well as to provide substantivity (resistance to removal by fluids) to ensure long-term antimicrobial activity.

Hydrophobic Component

Certain preferred compositions described herein also include one or more hydrophobic materials. In certain embodiments, the hydrophobic component can be the same as the antimicrobial component. For example, when the antimicrobial component is an antimicrobial lipid this component may also serve as an hydrophobic component. A hydrophobic material is typically an organic compound, which at 23° C. is a liquid, gelatinous, semisolid or solid and has a solubility in water of less than 5% by weight, preferably less than 1% by weight, more preferably less than 0.5% by weight, and even more preferably less than 0.1% by weight. These materials include compounds typically considered emollients in the cosmetic art.

Examples of general emollients include, but are not limited to, short chain (i.e., C1-C6) alkyl or (C6-C12)aryl esters of long (i.e., C8-C36) straight or branched chain alkyl or alkenyl alcohols or acids and polyethoxylated derivatives of the alcohols; short chain (i.e., C1-C6) alkyl or (C6-C12) aryl esters of (C4-C12)diacids or (C4-C12)diols optionally substituted in available positions by —OH; (C2-C18)alkyl or (C6-C12)aryl esters of glycerol, pentaerythritol, ethylene glycol, propylene glycol, as well as polyethoxylated derivatives of these; (C12-C22)alkyl esters or (C12-C22)ethers of polypropylene glycol; (C12-C22)alkyl esters or (C12-C22) ethers of polypropylene glycol/polyethylene glycol copolymer; and polyether polysiloxane copolymers. Additional examples of hydrophobic components include cyclic dimethicones, including volatile cyclic silicones such as D3 and D4, polydialkylsiloxanes, polyaryl/alkylsiloxanes, silicone copolyols, long chain (i.e., C8-C36) alkyl and alkenyl esters of long (i.e., C8-C18) straight or branched chain alkyl or alkenyl alcohols or acids, long chain (i.e., C8-C36) alkyl and alkenyl amides of long straight or branched chain (i.e., C8-C36) alkyl or alkenyl amines or acids; hydrocarbons including straight and branched chain alkanes and alkenes such as isoparaffins (e.g., isooctane, isododecane, isooctadecane, etc.), squalene, and mineral oil, polysiloxane polyalkylene copolymers, dialkoxy dimethyl polysiloxanes; (C12-C22)alkyl and (C12-C22)alkenyl alcohols, and petroleum derived alkanes such as isoparaffins, petrolatum, petrolatum USP, as well as refined natural oils (especially NF or USP grades) such as olive oil NF, cotton seed oil, peanut oil, corn oil, castor oil, sesame oil, safflower oil, soybean oil, and the like, and blends thereof. In certain preferred embodiments, the hydrophobic components useful in the compositions described herein include those selected from the group consisting of petrolatum USP and short chain (i.e., C1-C6) alkyl or (C6-C12)aryl esters of long (i.e., C8-C36) straight or branched chain alkyl or alkenyl alcohols or acids and polyethoxylated derivatives of the alcohols; short chain (i.e., C1-C6)alkyl or (C6-C12)aryl esters of (C4-C12)diacids or (C4-C12)diols optionally substituted in available positions by —OH (such as diisopropyladipate, diisopropylsebacate); (C1-C9)alkyl or (C6-C12)aryl esters of glycerol, pentaerythritol, ethylene glycol, propylene glycol (such as glyceryl tricaprylate/caprate); and mixtures thereof. Other useful emollients include (C12-C15)alkyl esters of benzoic acid, fatty alcohols such as stearyl or cetyl alcohol, and lanolin USP or lanolin derivatives. For certain particularly preferred embodiments, the hydrophobic component is petrolatum.

One or more hydrophobic materials may be used in the compositions described herein at a suitable level to produce the desired result. In a preferred embodiment (in which the compositions include very little or no water), the hydrophobic component is present in a total amount of at least 50 wt-%, more preferably at least 70 wt-%, and even more preferably at least 80 wt-%, based on the ready to use composition. In a preferred embodiment, the hydrophobic component is present in a total amount of no greater than 99 wt-%, more preferably no greater than 95 wt-%, and even more preferably no greater than 92 wt-%, based on the ready to use composition. When the hydrophobic component is present in the greatest amount it is referred to as a "vehicle." In those formulations where the hydrophobic component(s)

and the hydrophilic component(s) are present at the same concentrations, the continuous phase is considered the "vehicle."

Penetration Agents

A penetration agent may also be used to facilitate the diffusion of the composition in whole or in part, but preferably diffusion of at least the antimicrobial component (and optionally any enhancer, secondary active, or surfactant, if present) into or through tissue in order to kill or inactivate microorganisms and reduce inflammation in affected tissues. A penetration agent is an agent used to increase the permeability of the tissue to the antimicrobial component and pharmacologically active agent, if present, to increase the rate at which the antimicrobial and/or secondary active agent diffuses into the affected or adjacent tissues.

Preferably, the antimicrobial component is able to diffuse into any fluid associated with the condition to be treated and kill or inactivate the microorganisms. Furthermore, preferably the antimicrobial component and/or surfactant component are able to reduce the surface tension of the fluid to facilitate kill and expulsion of the fluid from the affected site, e.g., to spread and kill microorganisms between the urethral wall and a catheter and to facilitate drainage of any fluid that may build up extraluminally. A penetration agent may increases permeability by reversibly damaging or by altering the physiochemical nature of the treated tissue to reduce its diffusional resistance.

Preferred penetration agents are non-toxic, nonirritating, non-sensitizing and non-comedogenic, readily emulsifiable in water, good solvents to solubilize the formulation components such as the antimicrobial, enhancer, and surfactant components (if present), has a high positive spreading coefficient, is a good wetting agent for dry and wet tissue and is stable to hydrolysis within pH range of about 3-8. Preferred penetration agents are water insoluble. The penetration enhancing component (penetration agent) may be used in concentrations of 0-99%. In some preferred embodiments the penetration agent is the vehicle.

Examples of penetration agents include without limitation: alcohols such as ethanol and isopropanol; polyols such as n-alkanols, limonene, terpenes, dioxolane; glycols such as propylene glycol, dipropyelne glycol, butylenes glycol, and glycerol; sulfoxides such as dimethylsulfoxide (DMSO) and methyl dodecyl sulfoxide; amides such as dimethylformamide and dimethylacetamide; ketones; oleates such as triolein and polyethylene glycol oleates such as PEG-5 oleate; various alkanoic acids such as caprylic acid; lactam compounds such as azone and N-methylpyrrolidone; alkanols such as oleyl alcohol and polyethoxylated oleyl alcohol; dialkylamino acetates, and admixtures thereof. The use of such penetration agents is disclosed, for example, in U.S. Pat. No. 6,093,417. Preferred delivery enhancing components include lauryl alcohol, lauramide DEA, lauryl pyrrolidone-5-carboxylate (e.g., Laurydone); ascorbyl palmitate; glycerol; tetraglycol (alpha-[(tetrahydro-2-furanyl)methyl]-omega-hydroxy-poly(oxy-1,2-ethan ediyl)), lauryl glycol (i.e., 1,2-dodecanediol), and mixtures thereof.

Particularly preferred penetration agents are alkyl esters, aralkyl esters, and alkaryl esters such as short chain alkyl or aryl esters (C1-C6) of long chain straight or branched chain alkyl or alkenyl alcohols or acids (C8-C36) and their polyethoxylated derivatives (a particularly preferred subclass are benzoic acid esters of alkyl alcohols such as (C12-C15)alkyl benzoate which is commercially available as FINSOLV, Finetex Inc., Elmwood Park, N.J.); short chain alkyl or aryl esters (C1-C6) of (C4-C12)diacids or diols optionally substituted in available positions by —OH; alkyl or aryl (C1-C9)esters of glycerol, pentaerythritol, ethylene glycol, propylene glycol, as well as polyethoxylated derivatives of these and polyethylene glycol; (C12-C22)alkyl esters or ethers of polypropylene glycol; (C12-C22)alkyl esters or ethers of polypropylene glycol/polyethylene glycol copolymer; and polyether polysiloxane copolymers.

It is noted that many of the surfactants disclosed herein may also significantly improve penetration of the antimicrobial composition or its components. For example, many sulfonated surfactants are well known to disrupt the stratum corneum and help enhance penetration of active ingredients into and through skin. For the purposes of this invention these components are still considered surfactants. Compositions that include a surfactant may not require an addition penetration agent. Similarly some some of the hydrophobic and/or hydrophilic components disclosed herein may also significantly improve penetration of the antimicrobial composition or its components.

It is also noted that many of the antimicrobial lipids are themselves amphipathic and may improve penetration into the treated tissue. Therefore, compositions high in the antimicrobial lipid may not require an additional penetration agent.

In addition, the penetration agent may help the antimicrobial component to penetrate into a polymeric surface of a device.

Optional Additives

Compositions described herein may additionally employ adjunct components conventionally found in pharmaceutical compositions in their art-established fashion and at their art-established levels. Thus, for example, the compositions may contain additional compatible pharmaceutically active materials for combination therapy (such as supplementary antimicrobials, anti-parasitic agents, antipruritics, antipyretics, astringents, local anesthetics, analgesics, steroids, non-steroidal anti-inflammatory agents, or other anti-inflammatory agents, sodium channel blockers, and the like), or may contain materials useful in physically formulating various dosage forms of the present invention, such as excipients, dyes, perfumes, lubricants, thickening agents, stabilizers, preservatives, flavorants, or antioxidants.

It will be appreciated by the skilled artisan that the levels or ranges selected for the required or optional components described herein will depend upon whether one is formulating a composition for direct use, or a concentrate for dilution prior to use, as well as the specific component selected, the ultimate end-use of the composition, and other factors well known to the skilled artisan.

It will also be appreciated that additional antiseptics (i.e., disinfectants) may be included and are contemplated. These include, for example, "azole" antifungal agents including clortrimazole, miconazole, econazole, ketoconazole, and salts thereof; and the like.

In certain embodiments, compositions of the present invention include a second active agent that includes a local anesthetic, analgesic, anti-inflammatory agent, an antipyretic, or combinations thereof. Examples of local anesthetics include, but are not limited to, lidocaine, benzocaine, proxime hydrochloride, prilocaine, menthol and mixtures thereof.

Formulations and Methods of Preparation

Many of the compositions described herein have exceptional broad spectrum antimicrobial activity and thus are generally not terminally sterilized but if necessary may be sterilized by a variety of industry standard techniques. For example, it may be preferred to sterilize the compositions in their final packaged form using electron beam. It may also be possible to sterilize the sample by gamma radiation or heat. Other forms of sterilization may be acceptable. It may also be suitable to include preservatives in the formulation to prevent growth of certain organisms. Suitable preservatives include industry standard compounds such as parabens (methyl, ethyl, propyl, isopropyl, isobutyl, etc.), 2-bromo-2 nitro-1,3-diol; 5-bromo-5-nitro-1,3-dioxane, chlorbutanol, diazolidinyl urea; iodopropylnyl butylcarbamate, phenoxyethanol, halogenated cresols, methylchloroisothiazolinone, and the like, as well as combinations of these compounds.

The compositions described herein preferably adhere well to mammalian tissues (particularly, skin, mucosal tissue, and wounds), in order to deliver the antimicrobial to the intended site over a prolonged period even in the presence of perspiration, drainage (e.g., mucosal secretions), or mild lavage. The component in the greatest amount (i.e., the vehicle) in the formulations of the invention may be any conventional vehicle commonly used for topical treatment of human or animal skin. The formulations are typically selected from one of the following three types: (1) anhydrous or nearly anhydrous formulations with a hydrophobic vehicle (i.e., the hydrophobic component, which can include one or more hydrophobic compounds, is present in the greatest amount); (2) anhydrous or nearly anhydrous formulations with a hydrophilic vehicle (i.e., the hydrophilic component, which can include one or more hydrophilic compounds, is present in the greatest amount); and (3) viscous water-based formulations. These are discussed below.

(1) Anhydrous or Nearly Anhydrous Formulations with a Hydrophobic Vehicle. In certain preferred embodiments of the present invention, the compositions include an antimicrobial component in a hydrophobic vehicle optionally in combination with surfactant(s), an enhancer component, and a hydrophilic component. In most instances the enhancers are not soluble in the hydrophobic component at room temperature although they may be at elevated temperatures. The hydrophilic component is generally present in a sufficient amount to stabilize (preferably to solubilize) the enhancer(s) in the composition. For example, when formulating with organic acid enhancers or certain solid surfactants in petrolatum many enhancers and surfactants will dissolve into the petrolatum at temperatures above 85° C.; however, upon cooling, the enhancer and/or surfactant crystals or precipitates back out of solution making it difficult to produce a uniform formulation. If at least 0.1 wt-%, and preferably at least 1.0 wt-%, more preferably at least 5 wt-%, and most preferably at least 10 wt-%, of a hydrophilic compound (e.g., a glycol) is added, a stable formulation can be obtained. It is believed that these formulations produce an emulsion in which the enhancer and/or surfactant is dissolved, emulsified, or dispersed in the hydrophilic component which is emulsified into the hydrophobic component(s). These compositions are stable upon cooling and centrifuging.

The hydrophilic component also helps to stabilize many of the surfactants used in preferred formulations. For example, dioctylsulfosuccinate sodium salt (DOSS) dissolves in glycerin at elevated temperatures and helps keep the DOSS physically stable in the composition. Furthermore, it is believed that incorporation of the hydrophilic component in the formulation improves the antimicrobial activity. The mechanism for this is unknown; however, it may speed the release of the enhancer component and/or the antimicrobial component.

The water content of these formulations is preferably less than 20%, preferably less than 10 wt-%, more preferably less than 5 wt-%, and even more preferably less than 2 wt-%, in order to minimize hydrolysis of any ester and/or antimicrobial present.

Furthermore, it has been found that it is particularly desirable where the antimicrobial component is an antimicrobial lipid based on the ester of glycerin or propylene glycol includes an ester to use either glycerin or propylene glycol in the hydrophilic component. It is most preferred to use a hydrophilic compound that is identical to the glycol portion of the antimicrobial lipid, e.g., propylene glycol with the propylene glycol esters and glycerin with the glycerin esters. In this manner, transesterification of the antimicrobial lipid ester with the hydrophilic compound will not result in additional chemical species present. In fact, there is some evidence to show that use of glycerolmonolaurate, which is 95% pure, when formulated with glycerin as a hydrophilic compound results in formation of additional glycerol monolaurate due to transesterification of the diester with the glycerin to produce two moles of the monoester. For this reason, it may be possible to initially formulate with lower grade glycerin ester that contains considerable levels of diester present, as long as it transesterifies during manufacture and/or storage to produce a formulation that includes less than 15% diester and preferably less than 5% diester based on the total weight of antimicrobial lipid present.

These formulations can be relatively easily manufactured by first heating the hydrophobic component to 85° C., adding in the surfactant, hydrophilic component, and enhancer component, cooling to 65° C., and adding the antimicrobial component above its melting point (if applicable and less than a temperature which would result in significant degradation of the components). Alternatively, the enhancer component can be predissolved in the hydrophilic component (optionally along with the surfactant) and added to the hydrophobic component either before or after addition of the antimicrobial component. If either the antimicrobial component or the hydrophobic component is a solid at room temperature this is done at the minimum temperature necessary to melt, or dissolve all components. If the antimicrobial component does not dissolve it may be sufficient to simply ensure a uniform and stable dispersion. Exposure of ester containing components (e.g., an oil or antimicrobial lipid) to components that include either acid or ether groups (e.g., enhancers) to elevated temperatures for extended periods of time should be avoided to prevent transesterification reactions (unless this is deliberate in the case of utilizing lower purity fatty acid esters in combination with glycol hydrophilic components to produce the monoesters as discussed above).

Thus, the present invention provides methods of manufacture. One preferred method involves: dissolving or dispersing the enhancer component in the hydrophilic component; combining the hydrophobic vehicle and the hydrophilic component with the enhancer component dissolved or dispersed therein with mixing to form a mixture; optionally heating the hydrophobic vehicle to a temperature sufficient to form a pourable liquid (which for many hydrophobic vehicles this is above its melting point) before or after combining it with the hydrophilic component and enhancer component; adding the antimicrobial component to the mixture; and cooling the mixture before or after adding the antimicrobial component.

The hydrophilic component may or may not be present in the formulations that include a hydrophobic vehicle. Thus, another preferred method of manufacture involves: combining the enhancer component and the hydrophobic vehicle with mixing to form a mixture; optionally heating the hydrophobic vehicle to a temperature sufficient to form a pourable liquid (which for many hydrophobic vehicles is above its melting point) before or after combining it with the enhancer component; adding the antimicrobial component to the mixture with mixing; and cooling the mixture before or after adding the antimicrobial component.

Surprisingly, it has been found that these compositions are significantly less irritating than formulations using completely hydrophilic components. In blind human trials participants were asked to instill 0.5 gram (g) of ointments in the nose based on hydrophobic components (e.g., petrolatum) that include an AHA enhancer, surfactant, and 10% hydrophilic component (e.g., glycerin) as well as ointments based on hydrophilic components (e.g., PEG 400/PEG 1450) using the same enhancer and surfactant. Surprisingly, the ointments based on the hydrophobic component were preferred by 100% of the participants.

Most preferably, the formulations intended for use in or near the urethra where drainage would be a concern are essentially gelatinous at room temperature, having a significant yield point such that they do not flow readily at temperatures below 35° C. The viscosity is measured using the viscosity test described herein. Certain gelatinous vehicles may also have a characteristic temperature at which they "melt" or begin to dramatically lose viscosity. Preferably this is higher than body temperature also to ensure that excess drainage of the composition of the treatment site does not occur. Therefore, the melting point of the composition is preferably greater than 32° C., more preferably greater than 35° C., and even more preferably greater than 37° C. The melting point is taken as the lowest temperature at which the viscosity becomes dramatically less or is equal to or less than 20,000 cps.

Similarly the viscosity and/or melt temperature can be enhanced by either incorporating a crystalline or semicrystalline hydrophobic carrier such as a higher melting petrolatum or microcrystalline waxes, and crystalline or semicrylastalline emulsifiers, addition of an insoluble filler/thixotrope, or by addition of a polymeric thickener (e.g., a polyethylene wax in a petrolatum vehicle). Polymeric thickeners may be linear, branched, or slightly crosslinked. It is important for comfort that the formulations are relatively soft and that they spread easily to allow easy application, especially over sensitive tissue such as the meatus, labia, and other vaginal tissue, nasal tissue, and the like. A particularly preferred vehicle in areas such as these where high viscosity is desirable is white petrolatum USP having a melting point greater than 30° C., and preferably greater than 35° C. Mineral jelly may also be suitable.

Preferably, these compositions have a viscosity of at least 500 centipoise (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). The viscosity can be measured as described below in the Viscosity Test. Most preferred compositions meet these viscosity values even after heating to 32° C. or even 35° C. or as high as 37° C. to ensure when in contact with mammalian tissue the compositions remain substantive (2) Water in Oil Emulsions. Antimicrobial components of this invention can be formulated into water-in-oil emulsions in combination with enhancer(s) and surfactant(s). Particularly preferred compositions comprise at least 35%, preferably at least 40%, more preferably at least 45%, and most preferably at least 50%, by weight oil phase. As used herein the oil phase includes all components which are either not soluble in water or preferentially soluble in the oil(s) present at 23° C. One method of preparing these emulsions is described in International Publication No. WO 2003/028767. Generally speaking, the hydrophobic component (oil) is mixed in Container A along with any emulsifier(s) optionally including polymeric emulsifiers and heated to a temperature sufficient to ensure a homogenous composition and subsequent stable emulsion. The temperature is typically raised to at least 60° C., preferably to at least 80° C., and more preferably to 100° C. or more. In a separate Container B, the hydrophilic ingredients are mixed, including one or more of the following: water, hydrophilic component, enhancer(s), surfactant(s), and acids/bases to adjust the pH of the final composition. The contents of container B are heated to a temperature sufficient to ensure a stable final emulsion composition without significantly degrading any of the components, typically to a temperature greater than 40° C., preferably greater than 50° C., and more preferably greater than 60° C. While hot, container B is added to container A using a high shear mixer. The composition may be continuously mixed until cool (e.g., to a temperature of less than 40° C.) or it can be allowed to sit as long as the contents remain uniformly mixed. If the antimicrobial is heat sensitive, it is added with mixing during the cooling down period. If it is not heat sensitive, it may be added to either container A or container B. The viscosity of these compositions may be adjusted by altering the levels of emulsifier; changing the ratio of water to oil phase; selection of the oil phase (e.g., select from an oil (hydrophobic component), which is more or less viscous); incorporation of a polymeric or particulate thickener, etc.

(3) Hydrophilic Vehicle. Antimicrobial components of this invention can be formulated into a hydrophilic component such as that based on the hydrophilic compounds (discussed above) optionally in combination with the enhancer(s) and surfactant(s). Particularly preferred are polyethylene glycols (PEGs), including blends of different molecular weight PEGs, optionally containing one or more glycols. When using a hydrophilic component as the vehicle (i.e., the component used in the greatest amount, which can include one or more hydrophilic compounds), it should be preferably selected to maintain viscosity and melt temperature characteristics similar to those stated above for the anhydrous or nearly anhydrous formulations using a hydrophobic vehicle.

Similarly the viscosity can be enhanced by either incorporating a crystalline or semicrystalline hydrophilic compound such as a PEG of sufficient molecular weight, addition of an insoluble filler/thixotrope, or by addition of a polymeric thickener. Polymeric thickeners may be linear, branched, or slightly crosslinked. It is desirable for comfort that the formulations are relatively soft and that they spread easily to allow easy application, especially in the urethra or colonized/infected area. For this reason, a particularly preferred vehicle is based on a blend of a liquid or semi-solid PEG (PEG 400-1000) with a more crystalline PEG (PEG 1000-2000). Particularly preferred is a blend of PEG 400 with PEG 1450 in a ratio of 4:1.

Also particularly preferred are water dispersible hydrophilic vehicles. In particular, those water dispersible hydrophilic vehicles that are liquids, gels, or ointments at room temperature are particularly preferred (as opposed to those that are hard solids). These may be less irritating than glycol based vehicles due to a decreased osmotic drying effect on the tissue. Preferred dispersible vehicles include typically amphipathic compounds such as polyethoxylated ethers and esters. For example, particularly preferred components include PEG 4-PEG 50 glyceryl alkylates formed, for example, by making the alkyl carboxylic acid esters of polyethoxylated glycerin, PEG 5-PEG 100 castor oil (or hydrogenated castor oil) such as PEG 30 castor oil and PEG 40 hydrogenated castor oil, PEG 3-PEG 40 esters or ethers of unsaturated lipids such as PEG 6 oleate (oleth-6), PEG 8 dioleate, and the like. Also included in this group are mixed alkoxylated polymers. For example, water dispersible poloxamers (block copolymers of ethylene oxide and propylene oxide, e.g., PEG-PPG-PEG or the reverse PPG-PPG-PEG where PEG refers to polyethylene glycol and PPG refers to polypropylene glycol) which are available from BASF under the PLURONIC tradename. Additional, water dispersible alkoxylate copolymers include random and block copolymers of ethylene oxide and propylene oxide initiated onto any glycol having 2-6 alcohol groups such as PPG-12-buteth-16, PPG-33 buteth 45, PPG 20 glycereth 20. Also included are propoxylated alkyl alcohols and aralklyl alcohols such as PPG-14 butyl ether, PEG-40, PPG-15 stearyl ether, PEG 14 nonylphenol ether, PPG 20 methyl glucose ether, and the like. Polyurethane polymers of PPG or PEG such as the Polyol prepolymers available from Barnet Products Corp., Englewood Cliffs, N.J. Also included are polyethylene glyol esters of fatty acids such as PEG-20 dilaurate, PEG 10 dicaprylate, PEG 6-di-2-ethylhexanoate, and the like, as well as polyethoxylated polyhydroxy functional glycols such as glycerin esters such as PEG-20 glycerol laurate (TAGAT L), sorbitan esters such as those available under the TWEEN tradename from ICI, and the like. Also included are polyglyerin fatty acid esters such as polyglycerol 2-oleate, polyglycerol 2 isostearate, polyglycerol 6 dioleate, polyglyceryl 6 ricioleate, and the like some of which are available from Abitec under the CAPROL tradename. In some embodiments the dispersible vehicle may be the antimicrobial component. For example, a PEG 3 monoglyceride or PEG 5 propyelne glycol fatty acid ester may have antimicrobial activity and can also function as the vehicle. In most embodiments, the water content is less than 20%, preferably less than 10%, and more preferably less than 5% by weight of the composition.

In certain preferred embodiments of the present invention, the compositions are in the form of an ointment or cream. That is, the compositions are in the form of a relatively viscous state such that they are suitable for application to nasal passageways. Preferably, such compositions have a viscosity of at least 500 Centipoise (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). The viscosity can be measured as described below in the Viscosity Test. Preferred formulations have high viscosity even after application to mammalian tissue at 32-37° C.

(4) Water-based Formulations. Aqueous compositions described herein are those in which water is present in the greatest amount, thereby forming the "vehicle." For these systems it is particularly important that a relatively high viscosity be imparted to the composition to ensure that the antimicrobial composition is not rapidly dispersed off the afflicted area. These formulations also adhere well to tissue and thus deliver the antimicrobial to the intended site over a prolonged period even in the presence of perspiration, drainage (e.g., mucosal secretions), or mild lavage. Such a high viscosity can be imparted by a thickener system. The thickener system of the invention is compatible with the antimicrobial lipid composition described above in order to provide suitable antimicrobial efficacy, chemical and physical stability, acceptable cosmetic properties, and appropriate viscosity for retention in the afflicted area.

Preferably, compositions of this invention have a viscosity of at least 500 Centipoise (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). The viscosity can be measured as described below in the Viscosity Test. Preferred formulations have high viscosity even after application to mammalian tissue at 32-37° C. Because certain optional ingredients, such as enhancers, hydrophilic compounds, hydrophobic compounds, and the like, may effect the viscosity (either positively or negatively), the measured viscosity is that of the final composition.

Preferred thickener systems used in the compositions described herein are capable of producing viscoelastic compositions that are very stable. By varying the amount and type of thickener, the degree of elasticity can be adjusted from almost a purely viscous composition to a highly elastic and even gel-like composition. If emollients are added, increasing the elasticity and/or yield stress of the system imparts added stability to prevent separation of immiscible emollients. Excessive elasticity, however, is not preferred because an excessively elastic composition usually does not provide a cosmetically appealing product.

Significantly, thickener systems used in the present invention are capable of achieving high viscosities at relatively low total concentrations. The total concentration of the thickener system is preferably less than 8 wt-%, more preferably less than 5 wt-%, and most preferably less than 3 wt-%, based on the total weight of the ready to use composition. Preferably, the total concentration of the thickener system can be as little as 0.5 wt-%, based on the total weight of the composition. For certain embodiments, however, the total concentration of thickener system is greater than 1 wt-%, based on the total weight of the ready to use composition.

The thickener system can include organic polymers or inorganic thixotropes such as silica gel, clays (such as betonite, laponite, hectorite, montmorrillonite, and the like), as well as organically modified inorganic particulates materials, and the like. As used herein, an organic polymer is considered part of the thickener system if its presence in the composition results in an increase in the viscosity of the composition. Certain polymers that do not have these characteristics may also be present in the composition but do not contribute significantly to the viscosity of the composition. For purposes of this invention, they are not considered part of the thickener system. For example, certain nonionic polymers such as lower molecular weight polyethylene glycols (e.g., those having a molecular weight of less than 20,000) do not increase the viscosity of the composition significantly. These are considered part of the hydrophilic component, for example, rather than part of the thickener system.

The thickener system can be prepared from one or more nonionic, cationic, anionic, zwitterionic, or associative polymers as long as they are compatible with the antimicrobial and enhancer components of the composition. For example, certain acidic enhancers such as those that include carboxylic acid groups are most effective in their protonated form. This requires that the composition has an acidic pH. For this reason, many anionic thickeners based on neutralized carboxylic acid groups would not be suitable. For example, Carbopol-type thickeners based on polyacrylic acid salts do not typically thicken well at pH values of less than 5 and certainly less than a pH of 4.5. Therefore, at lower pH values (i.e., when acidic enhancers are present) if the aqueous compositions are thickened with anionic polymers, the polymers are preferably based on sulfonic acid, sulfate, phosphonic acid, or phosphate groups. These polymers are able to thicken at much lower pH values due to the lower pKa of these acid groups. Preferred polymers of this class include ARISTOFLEX HMB (ammonium acryloyldimethyltaurate/beheneth-25 methacrylate crosspolymer) and ARISTOFLEX ASV (ammonium acryloyldimethyltaurate/NVP copolymer) from Clariant Corporation. Other preferred sulfonic acid polymers are those described in U.S. Pat. No. 5,318,955.

Preferably, the compositions that include an acidic enhancer component are thickened using cationic or nonionic thickeners since these perform well at low pH. In addition, many of the nonionic and cationic polymers can tolerate higher levels of salts and other additives and still maintain high viscosity.

A preferred group of nonionic polymeric thickeners include modified celluloses, guar, xanthan gum, and other natural polymers such as polysaccharides and proteins, associative polymers based on nonionic ethylenically unsaturated monomers wherein at least one comonomer has at least 16 carbon atoms, and polymers based on ethylenically unsaturated monomers selected from the group consisting of acrylates, acrylamides, vinyl lactams, vinyl acetate and its hydrolyzed derivatives, methyl vinyl ethers, styrene, and acrylonitrile.

A preferred group of cationic polymeric thickeners include cationically modified celluloses, quaternized natural amino-functional polymers, and polymers based on ethylenically unsaturated monomers selected from the group consisting of acrylates, acrylamides, vinyl lactams, vinyl acetates, methyl vinyl ethers, styrene, and acrylonitrile.

Cationic polymers for use in the compositions of this invention can be selected from both permanently charged quaternary polymers (those polymers with quaternary amines such as Polyquaternium 4, 10, 24, 32, and 37, described below) as well as protonated primary, secondary, and tertiary amine functional polymers that have been protonated with a suitable protonic acid. Preferred protonated cationic polymers are based on tertiary amines. The protonated cationic polymers are preferably protonated with suitable acids that will not result in undue skin irritation. These include, for example, (C1-C10)alkylcarboxylic acids optionally substituted by oxygen (e.g., acetic acid, alpha-hydroxy acids such as lactic acid, gluconic acid, benzoic acid, mandelic acid, and the like), (C1-C10)alkylsulfonic acids (e.g., methylsulfonic acid and ethylsulfonic acid), (C1-C10)alkylhydrogensulfates (e.g., methylhydrogensulfate) and mineral acids (e.g., hydrochloric acid, hydrobromic acid, sulfuric acid, phosphoric acid, and the like).

The charge on protonated cationic polymers is pH dependent. For this reason, in order to ensure the polymer is sufficiently protonated, the pH is adjusted appropriately and should be in the range of preferably 2-9.5, more preferably 2-8, and most preferably 2.5-7.5. The pH of preferred compositions that include acidic enhancers should be lower and is typically 2-5, and preferably 2-4. It should be noted that it is not necessary to have all of the amines on a particular polymer protonated. The level of protonation will to a certain extent be pH dependent. With certain polymers in order to obtain optimum thickening with low skin irriation it may be beneficial to only protonate a small percentage of the available amine groups while with other polymers it may be beneficial to protonate substantially all of the amine groups. This will be easily determined by one skilled in the art.

The quaternary, tertiary, secondary, and primary amine functional polymers may be chosen from natural polymers, modified natural polymers, as well as synthetic polymers. These polymers may be soluble or swellable in the aqueous solvent. Furthermore, these polymers may also possess hydrophobic side chains and thus be associative polymers.

Polymers can be classified as soluble, swellable, or associative in the aqueous compositions. Some polymers may fall into one or more of these classes. For example, certain associative polymers can be soluble in the aqeuous system. Whether they are considered soluble, swellable, or associative in the aqueous system, suitable polymers for use in the compositions described herein may be film forming or not. Film forming polymers may retain the active antimicrobial component at the afflicted site for longer periods of time. This may be desirable for certain applications. For example, some film forming polymers may produce compositions that could not be easily washed off with water after being applied and dried.

As used herein, a soluble polymer is one that in dilute solution (i.e., 0.01-0.1 wt-% in the desired aqueous solvent system defined as containing water and any other hydrophilic compounds), after heating for a sufficient time to ensure solubilization of any potentially soluble components, has no significant observable particles of greater than 1 micron in particle size, as determined by light scattering measurements using, for example, Malvern Masterisizer E Laser Particle Size Analyzer available from Malvern Co., Boston, Mass.

As used herein, a swellable polymer is one that in dilute solution (i.e., 0.01-0.1 wt-% in the desired aqueous solvent system), after heating for a sufficient time to ensure solubilization of any potentially soluble components, has a significant (i.e., detectable) number of observable particles of greater than 1 micron in particle size, as determined by light scattering measurements using, for example, Malvern Masterisizer E Laser Particle Size Analyzer.

As used herein, an associative polymer is one that has greater than 2 hydrophobic chains per polymer molecule of greater than 16 carbon atoms. Examples of such polymers are as follows.

Soluble Polymers—Cationic Natural Polymer Derivatives. Cationic modified cellulosic polymers are reported in the literature to be soluble in water. Such polymers have been found to be useful in the present invention. The most preferred modified cellulose products are sold under the trade names CELQUAT (National Starch and Chemicals Corp., Bridgewater, N.J.) and UCARE (Amerchol Corporation, Edison, N.J.). CELQUAT is a copolymer of a polyethoxylated cellulose and dimethyldiallyl ammonium chloride and has the Cosmetic, Toiletry and Fragrance Association (CTFA) designation Polyquaternium-4.

An alkyl modified quaternary ammonium salt of hydroxyethyl cellulose and a trimethyl ammonium chloride substituted epoxide can also be used. The polymer conforms to the CTFA designation Polyquaternium 24 and is commercially available as QUATRISOFT LM-200 from Amerchol Corp., Edison, N.J.

A particularly suitable type of cationic polysaccharide polymer that can be used is a cationic guar gum derivative, such as guar hydroxypropyltrimonium chloride (Commercially available from Rhone-Poulenc under the trade designation JAGUAR).

Soluble Polymers—Cationic Synthetic Polymers. Synthetic cationic linear polymers useful in the present invention are preferably quite high in cationic charge density—generally having greater than 10 wt-% cationic monomer, preferably greater than 25 wt-%, and more preferably greater than 50 wt-%. This ensures a good cosmetic feel and may actually improve water solubility. In general, the polymers useful in the present invention have sufficient molecular weight to achieve thickening at generally less than 5 wt-% polymer, but not too high that the lotion/cream/ointment feels slimy and stringy. While the composition of the polymer will dramatically affect the molecular weight at which sufficient thickening will occur, the polymers preferably have a molecular weight of at least 250,000 daltons, and more preferably at least 500,000 daltons. The polymers preferably have a molecular weight of no greater than 3,000,000 daltons, and more preferably no greater than 1,000,000 daltons. The homopolymers are preferably prepared from methacryloyloxyalkyl trialkyl ammonium salt, acryloyloxyalkyl trialkyl ammonium salt, and/or quaternized dialkylaminoalkylacrylamidine salt. Preferably the polymers are copolymers of at least two monomers selected from the group consisting of trialkylaminoalkyl acrylate and methacrylate salts, dialkyldiallyl ammonium salts, acrylamidoalkyltrialkyl salts, methacrylamidoalkyltrialkyl salts, and alkyl imidazolinium salts, N-vinyl pyrrolidinone, N-vinyl caprolactam, methyl vinyl ether, acrylates, methacrylates, styrene, acrylonitrile, and combinations thereof. Typically, for the salts the counterions are preferably $F^-$, $Cl^-$, $Br^-$, and $CH_3(CH_2)_nSO_4^-$ where n=0-4.

A variety of quaternary copolymers of varying quaternization, can be synthesized based on homo or copolymers of amino acrylates with methyl, ethyl, or propyl side chains. These monomers could also be copolymerized with other nonionic monomers including quaternary acrylic homopolymers, such as homopolymers of 2-methacryloxyethyl trimethylammonium chloride and 2-methacryloxyethyl methyl diethyl ammonium bromide; and copolymers of quaternary acrylate monomers with a water-soluble monomers, such as Petrolite Product No. Q-0043, a proprietary copolymer of a linear quaternary acrylate and acrylamide at high molecular weight (4-5 million MW).

Another useful soluble cationic polymer is N,N-dimethylaminopropyl-N-acrylamidine (which is quaternized with diethylsulfate) bound to a block of polyacrylonitrile. This block copolymer is available under the trade designation Hypan QT-100 from Lipo Chemicals Inc., Paterson, N.J. It is quite effective at thickening aqueous systems and has a good cosmetic feel. This polymer as received, however, has an objectionable amine odor. The odor could probably be masked with the proper fragrance, but is preferably removed prior to formulation (e.g., with a solvent cleaning process) so that the formulation can be supplied without fragrance. Preferred compositions are free of fragrances and colorants.

Suitable cationic polymers include, for example, copolymers of 1-vinyl-2-pyrrolidine and 1-vinyl-3-methyl-imidazolium salt (e.g., chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate, referred to in the industry (CTFA) as Polyquaternium-11. This material is available commercially from ICI Corp., Wayne, N.J., under the trade designation GAFQUAT; cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively.

Soluble Polymers-Nonionic. A variety of cellulosic ethers are reported in the literature to be soluble in water. Materials in this class that are nonionic and have been shown to be useful include: methylhydroxypropylcellulose, available as BENECEL MP 943 from Aqualon, Wilmington, Del.; hydroxypropylcellulose, available as KLUCEL (LF, GF, MF, HF) from Aqualon; hydroxybutylmethylcellulose (3.5% hydroxybutyl and 30% methoxyl) from Scientific Polymer Products, Ontario, N.Y.; and hydroxyethylcelluloses, available under the trade designation NATROSOL from Aqualon. Xanthan gum, guar, locust bean gum, and other polysaccharides may also be suitable. These polymers may be produced from plant sources or can be produced through microbial cell culture. Polyvinyl alcohol (PVA) also may be suitable. For example, PVA made from polyvinyl acetate which has been hydrolyzed to 87% is highly water soluble at room temperature. Those with higher percent hydrolysis become progressively more crystalline and may need to be heated to get into solution. Protein thickeners such as gelatin and pectin may also be useful.

Amine oxide polymers such as those described in U.S. Pat. No. 6,123,933 (Hayama) and those commercially available under the trade designation DIAFORMER Z-711, Z-712, Z-731, and Z-751 from Clariant Corp. are useful. Additionally, zwitterionic polymers, such as methacryloyl ethyl betaine/acrylate copolymer that are commercially available under the trade designation DIAFORMER Z-400 from Clariant Corp. can also be used. Zwitterionic polymers described in U.S. Pat. No. 6,590,051 may also be useful.

Carboxylic acid functional polymers including naturally occurring carboxylic acid functional polymers such as hyaluronic acid and derivatives of natural polymers such as carboxymethylcellulose, alginic acid and other alginate polymers, Fucogel (a polysaccharide consisting of three mono-saccharides, fucose, galactose, and galacturonic acid), hyaluronic acid, and the like, also may be useful. Synthetic polymers may also be useful, such as those based on carboxylic acid, phosphonic acid, or sulfonic acid functional monomers, including but not limited to, polymers derived from acrylic acid, methacrylic acid, maleic anhydride, itaconic anhydride, sodium AMPS (the sodium salt of 2-acrylamido-2-methylpropane sulfonic acid), sulfopropyl acrylate or methacrylate, sulphomethylated acrylamide, allyl sulphonate, sodium vinyl sulphonate, combinations thereof, or other water-soluble forms of these or other polymerizable carboxylic or sulphonic acids.

Swellable Polymers. Many swellable polymers, which are slightly crosslinked, function as viscosifiers in aqueous solvent systems. In general, these swellable polymers are preferred because they tend to be far less "slimy" going on and once the hands perspire and are exposed to water after treatment. Excessive crosslinking will result in polymers that do not swell sufficiently to increase the viscosity of the composition. In order to ensure adequate swelling, if a chemical crosslinker is used, the concentration of crosslinker is quite low, e.g., less than 1000 parts per million (ppm), and preferably less than 500 ppm, based on the weight of the dry polymer.

A class of crosslinked polymers suitable for use in the compositions described herein include acrylamide and at least one other quaternary monomer selected from the group consisting of trialkylaminoalkylacrylate and methacrylate salts, dialkyldiallyl ammonium salts, acrylamidoalkyltrialkyl ammonium salts, methacrylamidoalkyltrialkyl ammonium salts, and monomers that include imidazolinium salts. The counterions are preferably $F^-$, $Cl^-$, $Br^-$, and $CH_3(CH_2)_nSO_4^-$ where n=0-4. Other comonomers may also be added including N-vinyl pyrrolidone, N-vinyl caprolactam, methyl vinyl ether, acrylates, methacrylates, styrene, and the like. A particularly preferred polymer is a poly(2-methacryloxyethyl trimethyl ammonium chloride) polydimethylaminoethyl methacrylate, which conforms to the CTFA designation Polyquaternium 37. Another preferred polymer includes acrylamide and methacryloyloxyethyl trimethyl ammonium chloride, which conforms to the CTFA designation Polyquaternium 32. These are commercially available from Allied Colloids Inc. of Suffolk, Va. as SALCARE SC95, SC96, and SC92.

Other swellable polymers (i.e., slightly crosslinked polymers) can be prepared using ionizing radiation to crosslink. For example, polymers of N-vinyl lactams, such as N-vinyl pyrrolidone, when exposed to gamma radiation increase in molecular weight and may actually crosslink. This crosslinking allows for more efficient thickening (less polymer required to achieve a certain viscosity) and an improved cosmetic feel. Other polymers that when exposed to gamma radiation result in crosslinking, include polymers such as LUVIQUAT HM 552 (copolymers of vinylimidazolium methochloride and vinylpyrrolidone, which conforms to the CTFA designation Polyquaternium-16), and GAFQUAT HS-100 (vinylpyrrolidone/methacrylamidopropyltrimethylammonium chloride copolymer which conforms to the CTFA designation Polyquaternium-28).

Chemical crosslinking using polyunsaturated monomers such as diallyl maleate may also prove useful. Other suitable crosslinkers are multi-ethylenically unsaturated compounds wherein the ethylenic groups are vinyl groups (including substituted vinyl groups, such as isopropenyl groups), allyl groups, and/or methallyl groups, which groups are bonded to nitrogen or oxygen atoms. Vinyl, allyl, and methallyl groups, as used herein, include substituted derivatives. Exemplary compounds include divinyl, diallyl, or dimethallyl esters, ethers, amides, or ureas. Specific examples are disclosed in U.S. Pat. No. 5,225,473 (Duan) and U.S. Pat. No. 4,931,282 (Asmus et al.).

A range of crosslinked polyvinylpyrrolidone (PVP) materials have been prepared via covalent crosslinking with diallyl maleate or by radiation crosslinking of linear PVP powders. Crosslinked PVP prepared under these techniques can produce colloidal particles which are highly swellable in aqueous solutions and thereby produce viscous solutions. The polymers are also nonionic and have excellent compatibility with cationic excipients.

Anionic swellable polymeric thickeners may also be useful. As described above preferred anionic polymers for use with antimicrobial compositions which include carboxylic acid functional enhancers (and are thus formulated at lower pH) are polymers having sulfonic acid, sulfonate, phosphonic acid, or phosphate groups.

Associative Polymers. Associative polymers can be used to thicken the compositions described herein as well. Such polymers thicken as a result of hydrophobic or Van de Waals association of hydrophobic side chains. Such associative polymers can form viscous to gelled aqueous solutions despite their relatively low molecular weights. Polymers that are alcoholic soluble can be modified by the addition of a long chain hydrophobic group. A preferred class of such associative polymers are based on nonionic ethylenically unsaturated monomers wherein at least one comonomer has at least 16 carbon atoms.

An example is cetyl hydroxyethylcellulose, available as NATROSOL PLUS from Aqualon, which utilizes an associative mechanism to enhance the viscosity it produces. Grafted side chains of cetyl alkyl groups can associate with neighboring alkyl hydrophobes. These interpolymer associations can dramatically increase the viscosification efficiency of the polymer. Longer chain alklyl, alkenyl, and aralkyl groups may also be suitable. For example, another preferred associative polymer is Arsitoflex HMB, which is ammonium acryloyldimethyltaurate/beheneth-25 methacrylate crosspolymer and is available from Clariant Corp.

(5) Neat Compositions. The compositions described herein also may be delivered to the treatment site in a neat form or in a volatile solvent that rapidly evaporates to leave behind a neat composition. Such compositions may be solid, semi-solid, or liquid. In the case where the compositions are solid, the antimicrobial and/or the enhancer and/or the surfactant may optionally be microencapsulated to either sustain the delivery or facilitate manufacturing a powder, which is easily delivered. Alternatively, the composition can be micronized into a fine powder without the addition of other components or it may optionally contain fillers and other ingredients that facilitate powder manufacture. Suitable powders include, but are not limited to, calcium carbonate, calcium phosphate, various sugars, starches, cellulose derivatives, gelatin, and polymers such as polyethylene glycols.

When hydrophobic antimicrobial lipids are used, a method for micronizing a hydrophobic agent may be used wherein the hydrophobic agent is dissolved in an effective amount of a first solvent that is free of polymer (such as the method described in U.S. Pat. No. 6,746,635). The hydrophobic agent and the solvent form a mixture having a continuous phase. A second solvent and then an aqueous solution are introduced into the mixture. The introduction of the aqueous solution causes precipitation of the hydrophobic agent and produces a composition of micronized hydrophobic agent having an average particle size of 1 micron or less. The particle size for use in delivery to the nose or other tissue may be significantly larger to direct delivery to the proper site. For example, to deliver the antimicrobial powder to the nose, nasal cavities, and/or throat without passing into the lungs, larger particles may be required.

Bioadhesive polymers optionally may be added to neat compositions as well as the other physical forms. Numerous suitable bioadhesive polymers are discussed in International Publication No. WO 93/21906. Representative bioadhesive polymers of particular interest include bioerodible hydrogels described by H. S. Sawhney et al., in *Macromolecules*, 26:581-587 (1993), including polyhyaluronic acids, casein, gelatin, glutin, polyanhydrides, polyacrylic acid, alginate, chitosan, poly(methyl methacrylates), poly(ethyl methacrylates), poly butylmethacrylate), poly(isobutylmethacrylate), poly(hexlmethacrylate), poly(isodecl methacrylate), poly(lauryl methacrylate), poly(phenyl methacrylate), poly(methyl acrylate), poly(isopropyl acrylate), poly(isobutyl acrylate), and poly(octadecl acrylate). Preferred polymers are polyacrylic acid (e.g., CARBOMER polymers) and poly(fumaric-co-sebacic)acid. Other bioadhesive and bioerodible polymers are described in U.S. Pat. No. 6,746,635.

Particularly preferred are slightly crosslinked polyacrylic acids such as those sold under the CARBOPOL brand by BF Goodrich.

The antimicrobial compositions also may include suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

The neat compositions according to the present invention may be conveniently delivered in the form of an aerosol spray or foam presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. Those of skill in the art can readily determine the various parameters and conditions for producing aerosols without resort to undue experimentation. Devices similar to metered dose inhalers (MDI), dry powder inhaler (DPI), spacer/holding chambers in combination with MDI, and nebulizers can be used. Techniques for preparing aerosol delivery systems are well known to those of skill in the art. Generally, such systems should utilize components which will not significantly impair the biological properties of the agent (see, for example, Sciarra and Cutie, "Aerosols," in *Remington's Pharmaceutical Sciences*, 18th edition, 1694-1712 (1990)).

The compounds may also be formulated in rectal or vaginal compositions such as suppositories or retention enemas, e.g., containing conventional suppository bases such as cocoa butter or other glycerides.

Viscosity

Certain preferred compositions described herein have a viscosity of at least 500 Centipoise (cps) for ease of application topically. More preferably, compositions described herein have a viscosity of at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as 500,000 cps, 1,000,000 cps, or more). Lower viscosity compositions can be used, however, in certain applications, such as for the treatment of middle ear infection and chronic sinusitis. For example, afflictions of the middle ear (e.g., otitis media or infection of the middle ear) may be treated with compositions described herein having a viscosity lower than 1000 cps more readily by administration through the nose and into the Eustachian tubes. The viscosity is measured by the Viscosity Test described herein. Preferred compositions meet the above viscosity limitations even when warmed to 32° C. Most preferred compositions meet the above viscosity limitations even when warmed to 35° C., or as high as 37° C.

In some embodiments of the present invention, the compositions have a viscosity of at least 20 cps (although compositions having a viscosity of less than 20 cps, and even less than 10 cps can be formulated and used), preferably at least 100 cps, when measured by the Viscosity Test described herein. Higher viscosities are preferred to reduce migration as well as to provide substantivity (resistance to removal by fluids) to ensure long-term antimicrobial activity.

Importantly for some applications the composition should not obstruct the function of the instrument inserted. For example, in the case of a urethra the composition inserted into the urethra must not permanently plug a urinary catheter inserted into the bladder. Therefore, certain compositions will melt, dissolve, or disperse readily in contact with tissue and/or fluid. In some cases temporary "plugging" could be alleviated by a gentle press on the bladder to start urine flowing. Another consideration is the transparency of the composition. For certain applications the instrument inserted into the decolonized cavity may be at least in part an instrument for visual inspection of the decolonized tissue or other tissue in the body. In these applications the composition should not significantly obstruct the vision for the surgeon. Most preferred compositions for use in urethral applications melt, dissolve or disperse readily in saline (0.9% NaCl) at 37° C. This can be measured by placing 1 g of composition in a glass vial along with 9 mL of warm saline. After 30 min of incubation at 37° C. the composition should be dissolved, dispersed or flow easily (if still a separate phase) when the vial is gently inverted twice. This is most easily measured by emptying the contents after inverting the tube twice. Preferred compositions leave behind less than 0.30 g of composition, more preferably less than 0.2 g of composition, and most preferably less than 0.1 g of composition when tested according to the Dispersibility Test described in the Examples Section.

Delivery Methods and Devices

Antimicrobial compositions described herein can be provided to a medical professional in a single composite formulation or in multiple parts. For example, a composition can be provided in two parts (e.g., in two separate containers or two separate compartments of the same container), one part containing the antimicrobial component and one part containing the enhancer. Other components of the composition can be combined with either one of the two parts. Alternatively, the other components can be included in a third part.

In other embodiments, a composition can be provided in two parts and the antimicrobial lipid component can be made in situ. For example, a monoglyceride could be formed in-situ from a di- or tri-glyceride in the presence of a lipase such as a mammalian or bacterially derived lipase. This may occur on the tissue or prior to application to the tissue.

Topical treatment regimens according to the practice of this invention include applying a safe and effective amount of the compositions described herein directly to the colonized or infected tissue or mucous membrane; particularly, the urethra, nasal passages, oral tissues, and the like, that are particularly susceptible to microbial contamination.

Compositions described herein can be delivered using a variety of techniques. Typically, the compositions are delivered to the mammalian tissue in a manner that allows them to spread and perhaps penetrate into the tissue, as opposed to through the tissue into the blood stream. This concentrates the compositions locally at the site in need of treatment. This delivery can be accomplished by spraying, dipping, wiping, dropping, pouring, toweling, inhaling, or the like, onto the area to be treated.

In the methods of the present invention, the compositions may be provided as a formulation suitable for delivery to mammalian tissue (e.g., urethral, nasal, oral, skin and/or mucosal surfaces). Suitable formulations can include, but are not limited to, creams, gels, foams, ointments, lotions, balms, waxes, salves, solutions, suspensions, dispersions, water in oil or oil in water emulsions, microemulsions, pastes, powders, oils, lozenges, boluses, and sprays, and the like.

The compositions may be sprayed from a pressurized container. The pressure may be supplied by an external means such as squeezing the container, through the use of a mechanical pump, or with the use of a propellant. Suitable propellants include chlorofluorocarbons (CFCs), hydrochlorofluorocarbons (HCFCs), hydrofluorocarbons (HFCs), hydrofluoroethers (HFEs), perfluorinated alkanes, and (C1-C5)alkanes, such as propane and butane, as well as nitrous oxide and dimethyl ether. Preferred propellants are lower alkanes such as propane, butane, isobutene, as well as HCFCs.

If delivered as a foam, the composition may be dispensed from an aerating dispenser such as the F2 Finger Pump Foamer available from Air Spray International Pompano Beach, Fla. Alternatively, the foam may be generated using a suitable propellant such as those described above.

Ideally a dispenser can deliver the composition into the opening as well as to the surrounding tissue. For example, a dispenser could deliver the antimicrobial composition into the urethra as well as to the external tissue surrounding the urethral opening (meatus) such as the labia and vagina in a female or the tip of the penis in a male. This can be accomplished, for example, by packing the composition in a container that has a small tip capable of dispensing composition into the urethra as well as a tip capable of spreading composition over the external tissue. This may be accomplished from a single dispenser, two separate dispensers, or a dispenser with multiple tips. Ideally, a dispenser with multiple tips is used. For example, a syringe, tube, packet or other package that has a smooth small tip that can be inserted into the urethra (e.g., an external diameter less than about 7 mm and preferably less than about 5 mm can be used to dispenser antimicrobial into the urethra before or after application of a tip comprising a pad into which composition can be dispensed and spread over the external tissue. For example, the external tissue application tip could have a screw or locking mechanism that is engaged with the main applicator with a pad at the opposite end that is filled with the composition before application to the tissue. Devices such as a syringe which can be used with a single hand are ideal since the other hand may be needed to stabilize the opening of the canal (such as the urethra) during insertion. Optionally, a composition could simply be expelled onto a pad such as a foam, knit, woven or nonwoven pad and used to decontaminate the external tissue before or after decontamination of the opening (e.g., urethra).

For application to skin or mucosal tissue, for example, the compositions may be applied directly to the tissue from a collapsible container such as a flexible tube, blow/fill/seal container, pouch, capsule, etc. In this embodiment, the primary container itself is used to dispense the composition directly onto the tissue or it can be used to dispense the composition onto a separate applicator. For example, for delivery to the urethra, nose or topical tissue, the composition could be dispensed directly from a tube and spread by a number of means including squeezing the outside of the nose together repeatedly, wiping with the tip of the tube or with a separate device such as a spatula, cotton, rayon, or other natural or synthetic based fiber swab.

Other application devices may also be suitable including applicators with foam tips, brushes, and the like. Importantly, the applicator must be able to deliver the requisite amount of composition to the tissue. These applicators may even be used within the opening and may be beneficial toward disrupting the bacterial flora and making it easier more susceptible to the antiseptic. Therefore, in most instances applicator devices such as webs and swabs are coated on the applicator web at greater than 50% by weight of the dry web and preferably in excess of 100% by weight of the dry web. (On a swab this would include the weight only of the web and not the applicator stick.)

The collapsible containers may be made in a number of single layer, laminate, or coextruded constructions. Materials of construction may include polyolefins such as low, medium, or high density polyethylene including low and linear low density polyethylene, polypropylene, as well as copolymers of ethylene and/or propylene with other polar or non-polar comonomers; polyamides such as nylons; polyesters such as polyethylene terephalate, polybutyleneterephalate, polyethylenenaphthalate; polyurethanes; polyacrylates; and the like. In some constructions it may be desirable to include a barrier material to prevent evaporation of one or more components of the formulation. Suitable barrier materials include polyesters (e.g., polyethylene terephthalate, polyethylene naphthalate, polybutylene terephalate, and the like), fluorinated layers such as polytetrafluoroethylene (PTFE, e.g., TEFLON), polyamides (e.g., nylon), chlorotrifluoroethylene (ACLAR), polyvinylidene fluoride, as well as copolymers of perflourinated monomers with partially fluorinated monomers such as copolymers of tetrafluoroethylene/hexafluoropropylene/vinylidene fluoride (THV Fluorothermoplastic from Dyneon Company), polyvinylchloride, polyvinylidene chloride (PVDC, e.g., SARAN HB), ethylene vinyl alcohol (EVOH), polyolefins (e.g., polyethylene, high density polyethylene, polypropylene, and combinations thereof). Oriented and biaxially oriented polymers may be particularly preferred.

Particularly preferred barrier constructions include metallic foil barriers such as aluminum foil laminates, HDPE, PET, PETG, PEN laminates of polyester and polyolefin (in particular PET/HDPE or HDPE/PET/HDPE), laminates of PET and EVOH, biaxially oriented nylon, PVDC, Nylon/EVOH/Nylon (OXYSHIELD OUB-R), chlorotrifluoroethylene and laminates thereof, ceramic layer including silicon oxide ($SiO_x$ where x=0.5-2 and preferably 1-2) coated thermoplastics, and ceramic coated PET (CERAMIS available from CCL Container/Tube Division, Oak Ridge, N.J.).

In some embodiments, an applicator may be used to place the device and/or antimicrobial composition in the proper location, for example, on the mucosal surface of a vagina, urethra, nasal cavity, rectum, or the like. Examples of such applicators include, for example, cardboard or plastic tube applicators commonly used for inserting tampons or suppositories.

The compositions described herein can be delivered from various substrates for delivery to the tissue. For example, the compositions can be delivered from a wipe or pad which when contacted to tissue will deliver at least a portion of the composition to the tissue. For application to nasal cavities or urethra the compositions may be provided by a non-woven swab such as a "Q-tip" brand cotton swab, into a foam tip applicator, and the like. The substrate may be used to deliver the composition essentially instantaneously or may be left in contact with the tissue. For example, a substrate in a tubular form could be delivered to the urethra using a suitable applicator and left in the urethra for a period of time prior to catheter insertion. This may be beneficial for the clinician especially in female patients where finding the urethra/meatus can be difficult. For use in the nose the device may be an annular design to allow delivery of the active while allowing the patient to freely breathe through the nose. For delivery of antiseptic to the urethra a solid "plug" may be more useful.

Also, compositions described herein can be coated onto medical devices that contact mammalian tissue (e.g., skin, mucous membranes, wounds, etc.). Examples of such devices include catheters such as urinary tract catheters, nasal gastric tubes, peritoneal dialysis tubes, ventilator equipment inserted into the trachea, and the like.

In certain embodiments, it is highly desirable to have the antimicrobial component of the antimicrobial composition diffuse or migrate into the device. Hence, the device may be rendered antimicrobial and/or has an antimicrobial coating, which remains for an extended period of time, thus preventing biofilm formation on the device. It is also desirable that the composition not deteriorate the integrity of the catheter. For example, many hydrophobic components and penetration agents can rapidly degrade natural latex rubber and must be avoided. This can easily be tested by exposing a catheter to the composition for several hours at 37° C. and testing for weight uptake, as well as the tensile strength. Preferred compositions result in less than 10% loss in tensile strength and have less than 10% weight uptake measured after thoroughly washing the catheter after exposure to the composition. Typically natural rubber latex is the catheter type in use today which is most easily degraded. Other catheter materials in use today include polyurethane elastomer, silicone elastomers, and TEFLON.

Antimicrobial compositions described herein can be formulated for additional controlled release (beyond that provided by the compositions previously discussed) if desired. For example, the antimicrobial and/or enhancer component may be formulated into compatible liposomes, microcapsules, microglobules, microbeads, and/or microspheres such as those made from natural polymers including, but not limited to, polysaccharides, agar, starch and starch derivatives, cellulose and cellulose derivatives, and synthetic polymers such as polyolefins (e.g., polyethylene and polypropylene), polystyrene, polyacrylates, and the like, as well as inorganic materials such as clays and zeolites. The antimicrobial and/or enhancer component may also be formulated into multiple emulsions such as oil-in-water-in-oil emulsions or water-in-oil-in-water emulsions where the oil is an organic oil or a silicone base oil. In addition, water soluble or swellable polymers can be combined with the antimicrobial lipid in a soluble or swollen state, dried, and added to the various compositions to further sustain release. If a prolonged release of the antimicrobial and/or enhancer component is desired it also may be useful to incorporate a hydrophobic component in which the antimicrobial lipid is soluble.

Topical antimicrobial treatment regimens according to the practice of this invention include applying an effective amount of the compositions described herein directly to the infected or at-risk mammalian tissue (particularly, skin or mucous membrane); particularly, the urethran nasal passages that are particularly susceptible to microbial contamination, throat and trachea. Compositions described herein can be delivered using a variety of techniques. Typically, the compositions are delivered to the mammalian tissue (particularly, the skin and/or mucosal tissue) in a manner that allows them to penetrate into the tissue, as opposed to through the tissue into the blood stream. This concentrates the compositions locally at the site in need thereof. This can be accomplished by spraying, dipping, wiping, dropping, pouring, toweling, or the like, onto the area to be treated.

If a composition of the present invention includes certain poloxamer block copolymers of ethylene oxide and propylene oxide generally having greater than 60 mol-% polyethylene oxide (such as those available under the trade names PLURONIC F127 and F108 from BASF Corp.), as well as certain modified cellulose polymers, and is applied topically, for example, thermally induced gelation can occur. Thus, various components can be selected for use in compositions described herein to produce a desired application effect.

The dose and frequency of application will depend on many factors including the condition to be treated, the concentration of antimicrobial lipid and enhancer, the microbe to be killed, etc. Typically, the compositions will be delivered in dosages of at least 10 milligrams per square centimeter ($mg/cm^2$) of tissue, preferably at least 20 $mg/cm^2$ of tissue, more preferably at least 30 $mg/cm^2$ of tissue, and most preferably at least 50 $mg/cm^2$ of tissue, for most external applications. In tubular channels such as the urethra and nasal passages the passage is preferably filled or the composition is applied such that complete contact with the colonized tissue is ensured. Application can be made once, or several (e.g., 2-4) times prior to insertion of the instrument. Preferred compositions work with a single dose and achieve effective microbial reduction in less than 15 minutes, preferably less than about 10 minutes and most preferably in less than about 5 minutes. For decontamination of the nasal passages by simply inserting a gel the gel preferably is capable of melting or liquefying in order to allow the patient to breath through the nose after a short period of time, e.g., less than about 10 minutes.

For many applications the composition should provide lubrication in order to facilitate insertion of an instrument into the canal (e.g., a catheter into a urethra, an endotrahceal tube into a trachea, or a nasal/gastric tube into the nose). By this it is meant that the composition reduces the force of inserting a standard latex Foley catheter over that without the composition and may also reduce the potential for tissue damage. Preferred compositions lubricate the instrument as well as KY Jelly. The compositions preferably wet both the tissue and the instrument.

Objects and advantages of this invention are further illustrated by the following examples, but the particular materials and amounts thereof recited in these examples, as well as other conditions and details, should not be construed to unduly limit this invention.

EXAMPLES

Test Protocols

Urethral Model Antimicrobial Efficacy Test:

The following method is a test for antimicrobial effectiveness of test compositions on inoculated porcine urethral sections.

Inoculum Preparation:

Inoculum was prepared 18-24 hours prior to testing by removing a colony of *E. coli*, ATCC No. 53500 from stock culture and placing this into 9.0 mL Tryptic Soy Broth (TSB). The inoculated broth was mixed on a Vortex mixer and placed in an incubator at 37° C. overnight. On the day of testing, a 1.0 mL aliquot was removed from the overnight-inoculated TSB and placed into 9.0 mL TSB. This was thoroughly mixed on a Vortex mixer and compared to McFarland Standard No. 0.5 (which represents $10^8$ CFU/mL bacterial growth).

Urethra Specimens:

Urethras were harvested from 30-50 kg Yorkshire (farm feeder) pigs (female and male) in an aseptic manner and frozen immediately at −20° C. until use. A section of urethra was thawed slightly prior to testing the treatments to allow the urethras to become flexible, but not soft. The urethra was cut into 1 centimeter segments and immediately sliced in half longitudinally to form 2 sections having a "u" cross-section. The internal diameter varied somewhat with the size of the pig and the location along the urethra. The end near the bladder tends to be a little larger in diameter. Sample replicates were taken from the same section from urethra, i.e., the 2 halves. The urethral sections were warmed to 23° C. until ready to use. The natural flora present on specimens was checked each time a set of samples was tested. In each instance the natural flora was less than about $10^3$ CFU.

Testing:

Nine milliliters of neutralizing broth was added to sterile tubes and these were warmed and maintained at 37° C. The neutralizing broth was Dey Engle (DE) broth purchased as a solid and reconstituted according to directions from VWR Scientific Products, Batavia, Ill. For the hydrogen peroxide containing examples, bovine liver catalase was added (purchased from Sigma Aldrich, Milwaukee, Wis., having an activity of 47,400 units/mL). Twenty microliters (20 µL) was added to 20 mL of the DE broth.

Two 1-cm segment half slices of porcine urethra prepared as stated above were placed onto separate polyester films (1 inch diameter×4 mil thick circles; 2.54 cm diameter×100 µm thick) laying in a sterile Petri dish with the internal surface facing up. The urethra section was inoculated with 10 µl of inoculum onto each piece of urethra. The inoculum was placed in the center of the internal surface of the urethral section. The Petri dish was closed and placed into an incubator set at 37° C. for 30 minutes.

Four-ounce Nasco Whirl-Pak bags (available from VWR Scientific Products, Batavia, Ill.) were inverted and opened so that an inoculated sample (urethra sample and film) easily could be placed inside with a tweezer. A positive control (no treatment) was prepared, in duplicate, to determine the bacteria growth of the inoculum. The samples are incubated at 37° C. for 30 minutes. A negative control (no inoculum) was also prepared, in duplicate, to determine a bacterial base line by placing uninoculated 1 cm urethra in Whirl-Pak bags in oven at 37° C. for 30 minutes. After the inoculum was allowed to adhere to the urethral section for 30 minutes, it was completely covered with 1 mL of the treatment sample within the Whirl Pak bag. The treatment samples were free of any air bubbles. This was accomplished on more viscous samples by centrifuging at the minimum speed necessary to remove the air making certain not to cause physical separation of components in the sample. The Whirl-Pak bag was sealed and returned to the incubator at 37° C. for urethra exposure times of 2, 5 or 30 minutes. Treatments samples were prepared in duplicate.

After incubation the samples were removed from the incubator and a tube of 9.0 mL warm neutralizing broth (37° C.) was dispensed into the Whirl Pak bag containing the inoculated urethral sample smothered in treatment on the polyester disk. This was placed in a Stomacher 80 Circulator (available from Seward Ltd., Norfolk UK) for 2 minutes at high speed. After mixing a 1 mL aliquot was removed from the bag and dispensed into 9.0 mL of letheen (available from Remel, Lenexa, Kans.) broth neutralizer or in DE broth neutralizer for Examples 6, 15, 26, 30, 34, 44-46, 51-58, and 61-62. The sample was then serially diluted two more times. Aliquots (0.10 mL) were plated from the Whirl-Pak bag and each diluted tube onto Tryptic Soy Agar (TSA) plates. This was spread with a sterile hockey stick. The plates are labeled $10^2$, $10^3$, $10^4$, and $10^5$, respectively. An additional 1.0 mL was removed from the Whirl Pak bag, dispensed onto the TSA plates in duplicate and spread with sterile hockey stick. This was labeled as the plate $10^1$. The agar plates were placed in the incubator for 24 hours at 37° C. The plates were removed and the colony forming units (CFUs) were counted at the countable dilution. To calculate the log reduction the following was done: CFU counted on the countable plate was multiplied by the dilution marked on the plate to yield the recovered organisms (e.g., 55 colonies on the $10^3$ plate means there were 55000 CFU recovered). The log 10 recovery was calculated. The log recovery of the treatments was subtracted from the log recovery of the control to give the log reduction. The average log reduction of CFUs is determined by taking an arithmetic average of the log reduction values of the replicates.

Urine Elution Test

When a catheter is inserted into a urethra filled with an antimicrobial lubricant composition of the present invention, said lubricant composition may accumulate inside the catheter, causing a temporary blockage of the flow of urine. The purpose of this test was to evaluate the degree of blockage caused by various formulations.

Preparation of Artificial Urine (Au):

To 1.5 liters of distilled water was added 36.4 grams of urea and mixed until all the crystals were dissolved. Next was added 15.0 grams of sodium chloride, 9.0 grams of potassium chloride and 9.6 grams of sodium phosphate, which was mixed until clear. The pH was checked with indicator paper and adjusted to between pH 6 and 7 with 1N hydrochloric acid or 1N sodium hydroxide. The solution was diluted to 2 liters with water and an additional 4.0 grams of creatine and 100 milligrams of albumin were added.

Urine Elution Test Method:

The artificial urine (AU) was warmed to 37° C. in a water bath. A 50 mL plastic syringe was positioned vertically and held in place with a ring stand and clamp. The plunger was removed from the syringe. Attached to the syringe was a 12.7 cm length of natural rubber latex tubing, 0.32 cm ID, and 0.16 cm thickness. At the end of the rubber tubing was male-male plastic connector. A plastic clamp valve was placed just above the connector. The 50 mL syringe was filled with 40 mL of the warmed AU. The valve was primed by opening and allowing a small amount of AU through the valve and connector. Samples were prepared by taking a second piece of the same type of tubing, 7.6 cm long and filling it with a 2.5 cm plug of example formulation at one end of the tubing. Select examples were also filled and evaluated with plugs of 3.8 cm and 5.1 cm. The plugged end of the second piece of tubing was attached to the plastic connector, just below the clamp valve. The valve was opened and urine elution time was measured in seconds, as the time it took for first amount of fluid to begin to flow out of the tube.

Antimicrobial Efficacy Test

The purpose of this test is to mimic the actual use conditions for many topical antiseptics. In most cases a topical antiseptic is applied to the area, optionally with some rubbing, and allowed to remain in contact and kill any microorganisms present in an essentially static state. In this assay, a composition is spread onto a film to form a uniform coating 10 mil (250 µm) thick, a suspension of bacteria are directly inoculated onto the surface of the composition, after a defined period of time, the inoculated disk is placed in a neutralizing broth, and at least a portion of this is diluted and plated to enumerate the surviving bacterial. It should be noted that just as in the in-vivo condition, this in-vitro method takes into account the ability of the formulation to be wet by tissue or the bacteria/bacterial suspension wetting. In certain compositions the bacterial suspension will wet the composition very well and spread. With other compositions the bacterial suspension may remain as discrete droplets. This is expected to simulate in-vivo performance in wetting tissue and bacterial biofilms. Since preferred compositions of the present invention are ointments this works very well. For less viscous compositions a compatible thickening agent should be incorporated to achieve a viscosity of at least 20,000 cps and preferably at least 50,000 cps.

For all antiseptics used in this assay an initial experiment was conducted to confirm that the neutralization broth was effective at neutralizing the antiseptic while not damaging the microorganisms. In general, to confirm neutralization, 100 µL of inoculum (target organism concentration of 10-100 CFU/mL) was added to 20 mL (for DE neutralizer) or 100 mL (for the Sampling Solution) of warmed (36° C.) neutralizer broth, vortexed, and a sample disk with ointment was dropped into the broth (time zero, t0) and the tube mixed vigorously. This was done using a vortex mixer for the 20 mL samples and by hand shaking for the 100 mL samples. Aliquots (1 mL) in duplicate were pour plated at three time points: (1) immediately (<1 minute), (2) at 30 minutes, and (3) at 60 minutes post-inoculation (all at room temperature). Plating was done using tryptic soy agar (TSA). Plates were incubated at 36° C. for up to 48 hours. Plates were enumerated and CFU/mL calculated. The data was converted to log 10 CFU/mL. Both test samples and a numbers control were run. The numbers control consisted of 100 µL of inoculum added to 20 mL PBW (phosphate buffered water, PBW) to yield an organism concentration of 10-100 CFU/mL. The PBW was prepared as follows: A stock solution was prepared by dissolving 34 g potassium dihydrogenphosphate in 500 mL deionized water. This was adjusted to pH 7.2 using 10N sodium hydroxide and then diluted with deionized water to make exactly 1 liter. The stock solution was filter sterilized and dispensed into a sterile bottle and refrigerated. The PBW was prepared by adding 1.25 mL stock solution to 1 liter deionized water and steam sterilized at 121° C. for 25 minutes. After sterilization, the solution was mixed by swirling to ensure uniformity. A toxicity control was also run by adding 100 µL of inoculum to 20 mL neutralizer broth to yield an organism concentration of 10-100 CFU/mL.

Neutralizer Effectiveness: If the log 10 CFU/mL of the test sample is not more than 0.3 log less than the corresponding Numbers Control, the neutralization will be considered effective.

Neutralizer Toxicity: If the Toxicity Control (TC) is not more than 0.3 log less than the corresponding Numbers Control sample, the sampling solution will be considered non-toxic.

Test Organisms for Antimicrobial Efficacy Test

The test organisms for this assay were methicillin resistant *Staphylococcus aureus*, ATCC 33953 and *E. coli*, ATCC 11229. The initial suspension was prepared by suspending bacterial colonies from overnight growth plates in phosphate-buffered water (PBW). A 0.5 McFarland turbidity standard was used to obtain a cell density of approximately $1.0 \times 10^8$ CFU/mL.

Test Materials for Antimicrobial Efficacy Test

The samples for this assay were spread at room temperature to a uniform thickness of 10 mil (250 µm) using a laboratory knife coater onto a 100 µm thick biaxially oriented clean and 70 wt-% isopropanol sanitized polyester-terephthalate (PET) film. These coated samples were placed in sterile Petri dishes and sealed with Parafilm to prevent evaporation and preserve cleanliness. Bubbles in the formulation were minimized as much as possible. Spread samples containing any volatile solvents such as water were used within 24 hrs of spreading. Test samples were cut from the same PET coated films using a 70 wt-% isopropyl alcohol (IPA) disinfected 23 mm die, as described in the next section. The sample disks were stored in sterile Petri dishes until testing.

Neutralizing Broth: The DE broth was Dey Engle broth purchased as a solid and reconstituted according to directions from Difco Laboratoris, Detroit, Mich. The DE broth was used for all the antiseptics of this invention, except those examples containing triclosan. The Sampling Solution (below) was used to neutralize the examples containing triclosan.

Sampling Solution:

| Component | Concentration (g/liter) | Purchased from |
| --- | --- | --- |
| TWEEN 80 | 90.0 | Sigma Aldrich |
| Lecithin | 10 | Fisher Scientific Company (vegetable derived, 03376-250) |
| Potassium dihydrogen phosphate | 0.40 | Sigma Aldrich |
| Disodiumhydrogen phosphate | 10.1 | Sigma Aldrich |
| TRITON X-100 | 1.0 | Sigma Aldrich |
| Water | 888.5 | |

Inoculum Preparation for Antimicrobial Efficacy Test

The inoculum was serially diluted with phosphate buffered water (PBW) 10,000 fold ($10^{-4}$) to achieve a concentration of $1-5 \times 10^4$ CFU/mL. The inoculum suspension was enumerated at the beginning and end of the test period. The final count was within 0.1 log/mL of the initial count. Each disk was inoculated with between $10^{6.5}$ and $10^{7.5}$ bacteria.

Measurement of Antimicrobial Activity:

After first confirming neutralization, samples were tested for antimicrobial activity using an in vitro model that attempts to simulate in-use conditions. Using aseptic technique and steam sterilized materials (except for the ointments), 23 mm disks of each formulation were cut using a 70 wt-% IPA-disinfected 23 mm die. Two bacteria were tested: *Staphylococcus aureus* (MRSA 33953) and *E. coli* ATCC 11229. Each inoculum was prepared by suspending bacterial colonies from overnight growth plates in phosphate-buffered water (PBW). A 0.5 McFarland turbidity standard was used to obtain a cell density of approximately $1.0 \times 10^8$ CFU/mL. 50 µL of the inoculum was rapidly spotted on the surface of the test ointment (in 8-12 tiny droplets). After the last drop was applied the bacteria were allowed to remain in contact with the ointment for the specified period of time (e.g., 2.5 and 10 minutes). At the end of the exposure time (time bacteria are in contact with the composition) the inoculated disk was dropped into warm (36° C.) Neutralizer Broth (20 mL for DE and 100 mL for Sampling Solution) and mixed vigorously (vortexed using a VWR Vortex Genie 2) for 2 minutes for DE. Two one-hundred fold dilutions were prepared in Neutralizer Broth, and the bacteria enumerated using the pour plate. Plates were incubated at 36° C. for up to 48 hours. Colony Forming Units (CFUs) were counted.

The CFUs for each plate was multiplied by the dilution factor to arrive at CFU/mL, and converted to log 10 CFU/sample. Log 10 CFU/samples of duplicate tests were averaged and the log 10 reduction was calculated. Log reductions were calculated by subtracting the log 10 bacterial recovery of the test materials from the log 10 bacterial recovery of the control (100 μL of inoculum in 20 mL warm D/E neutralizing broth or 100 μL in 100 mL of Sampling Solution or 100 μl in 100 mL of Sampling Solution).

The compositions of the present invention were analyzed for their ability to kill MRSA and *E. coli* at 2.5 and 10 minutes. By comparison Bactroban Nasal ointment in this assay showed essentially no kill of this strain of MRSA at 2.5 min. (The log reduction values were 0.030 and –0.040.) In fact, Bactroban Nasal showed essentially no kill after contact for 2 hours. It is a significant advantage that the compositions of the present invention are able to kill microorganisms rapidly. Preferred compositions achieve at least a 1.5 log reduction in 10 minutes, more preferably at least a 2 log reduction in 10 minutes, and most preferably at least a 3 log reduction in 10 minutes. Particularly preferred compositions of the present invention achieve at least a 1.5 log reduction in 2.5 minutes, more preferably at least a 2 log reduction in 2.5 minutes, and most preferably at least a 3 log reduction in 2.5 minutes for at least one of the two test organisms. Most preferred formulations achieve these log reduction values for both test organisms.

Emergence of Resistance Test

Overnight cultures of each of 30 MRSA isolates and 30 Methicillin Susceptible *Stapyloccus aureus* (MS SA) isolates were grown in Mueller-Hinton broth (MHB) at 35° C. in room air. Bacteria in the broth were concentrated by centrifugation for 15 minutes at 2,200 revolutions per minute (rpm). The spent broth was decanted and replaced with fresh MHB containing 0.5 μL per mL of each of three antimicrobial compositions (Examples 31 (IPA), 32 (IPA), and 33 (IPA)) or 0.125 μg/mL of mupirocin lithium salt (Sigma Aldrich, Milwaukee, Wis.). The cultures were returned to the incubator for 18 hours. Following incubation, each culture was again centrifuged and the bacterial pellet was divided into two aliquots. One aliquot was resuspended in MHB containing fresh antimicrobial compositions at twice the previous concentrations and returned to the incubator for continued exposure.

The second aliquot was screened for MRSA and MSSA by incubation with 2 mL of MHB containing 4 μg/mL of mupirocin or 1,200 μg/mL of Examples 31 (IPA) or 32 (IPA) or 33 (IPA). The resistance screens were incubated overnight at 35° C. in room air. After incubation, each screen was subcultured to fresh MHB and incubated for 4 to 6 hours. Minimum inhibitory concentration (MIC) testing was performed on logarithmically growing bacteria recovered from the screen. This procedure was repeated for 8 days. After 8 days of serial exposure, each bacterial pellet was resuspended in bland MHB and incubated overnight. The MIC of each antimicrobial composition or mupirocin was determined as the $MIC_{90}$ (range) before and daily during serial passage.

Viscosity Test

In the following Examples (except where indicated) viscosity was measured at 23° C. at ambient pressure using a Brookfield LVDV-I$^+$ viscometer equipped with a model D Brookfield heliopath and T spindles B-F. The spindle and speed was chosen for each particular sample such that the viscometer was operating in the middle of its range. All samples were allowed to equilibrate at 23° C. for 24 hours prior to measurement. Preferably the viscosity is taken at the lowest speed possible while staying within 20-80% of the viscometer range and more preferably between 30-70% of the range. In all cases the sample size and container geometry was chosen to ensure that there were no wall effects. By "wall effects" it is meant the viscosity value is not affected by the container and is essentially equivalent to the viscosity taken in an infinitely large container. For this reason lower viscosity samples required a larger sample size to accommodate the larger spindles. The following table outlines preferred spindles for various sample viscosities.

| Sample Viscosity | T Spindle to Use |
|---|---|
| 1,000-100,000 | B |
| 1,000-200,000 | C |
| 5,000-500,000 | D |
| 10,000-1,250,000 | E |
| 500,000-3,000,000 | F |

The viscosity of each sample was taken as the highest relatively stable reading achieved on the first path the spindle traversed using the heliopath adapter.

Dispersibility Test

This method determines the relative ease with which a composition will disperse in warm (37° C.) saline. This method yields a semi-quantitative measure of how well the sample dispersed. All experiments were carried out in glass vials that can hold approximately 20 mL of water. Both qualitative and quantitative measures were used.

Baseline:

A tared vial was filled with 10 mL of saline (0.90% NaCl in deionized water). This was sealed and incubated 30 minutes in a 37° C. water bath. After inverting slowly twice the saline was drained out. The final weight was recorded. This was repeated and an average recorded. The vial retains about 0.26 g saline.

Testing of Examples:

One gram (1.0 g) of formulation is placed in the bottom of a tared vial and covered with 9 mL 37° C. saline. This was sealed and placed in a 37° C. water bath. After 30 minutes the vial was very slowly inverted twice in a period of about 5 seconds/inversion cycle. The sample was checked visually for evidence of sample remaining that was not dispersed. The appearance was recorded. The saline was decanted away making certain to retain any non-dispersed solids/masses using a spatula for retention. Care was taken to not remove any undispersed sample with the spatula. The vial was weighed and the net amount of sample remaining was determined. The percent sample remaining was determined according to the following equation: (sample wt remaining–wt of saline remaining (0.26))/1*100.

A negative number is possible if more of the saline with test sample drains out than did with pure saline. Numbers greater than 100% indicate that most, if not all, of the sample remained undispersed and that the sample may have swelled or otherwise retained saline in the vial.

TABLE 1

| Abrev. (optional) | Trade name | Description | Source | Address |
|---|---|---|---|---|
| | AC 540 | ethylene-acrylic acid copolymer | Allied-Signal | Morristown, NJ |
| | AARLAMOL E | PPG-15 stearyl ether | Uniqema | New Castle, DE |
| LMDO | AMMONYX LMDO | lauramidopropylamine/ Myristamidopropylamine oxide | Stepan Company | Northfield, IL |
| | ARISTOFLEX AVC | Ammonium Acryloyldimethyl taurate/VP Copolymer | Clariant Corp. | Charlotte, NC |
| DOSS | AEROSOL OT-75 | docusate sodium | Cytec IND Inc. | West Patterson, NJ |
| DOSS | COMPLEMIX | Docusate sodium | Cytec IND Inc. | West Paterson, NJ |
| | BE-22 | Behenyl alcohol | M. Michel and Company, Inc. | New York, NY |
| | Benzalkonium chloride | Benzalkonium chloride | Aldrich | Milwaukee, WI |
| | Benzethonium chloride | Benzethonium chloride | Aldrich | Milwaukee, WI |
| | BRIJ 700 | Polyethylene (100) Stearyl Ether | ICI Specialty Chemicals | Wilmington, DE |
| | CAPMUL PG8 | Propylene glycol monocaprylate | ABITEC Corp. | Janesville, WI |
| | CAPMUL PG12 | Propylene glycol monocaprylate | ABITEC Corp. | Janesville, WI |
| | CARBOPOL 941 NF | Polyacrylic acid | BF Goodrich | Clevevland, OH |
| PEG 400 | CARBOWAX 400 | Polyethyleneglycol 400 | DOW/Union Carbide | Danbury, CT |
| PEG 1450 | CARBOWAX 1450 | Higher MW PEG, e.g 1450 | DOW/Union Carbide | Danbury, CT |
| PEG 3350 | CARBOWAX 3350 Flake NF | Higher MW PEG, e.g 3350 | DOW/Union Carbide | Danbury, CT |
| | CARBOWAX WSR N 3000 | 400,000 MW PEG | DOW/Union Carbide | Danbury, CT |
| | CENTROFLEX F | Lecithin | Central Soya | Fort Wayne, IN |
| | CERAPHYL 31 | Lauryl lactate 48% | ISP | Lombard, IL |
| | PELEMOL LL | Lauryl lactate 75% | ISP | Lombard, IL |
| | CERAPHYL 494 | Isocetyl stearate | ISP | Lombard, IL |
| | CERASYNT GMS | Glyceryl stearate | ISP | Lombard, IL |
| | Cetyl palmitate | Cetyl palmitate | Jarchem Industries | Newark, NJ |
| CPC | Cetylpyridinium chloride | Cetylpyridinium chloride | Sigma | St. Louis, MO |
| CTAB | Cetyltrimethyl- ammonium bromide | Cetyltrimethyl- ammonium bromide | Aldrich Chemical | Milwaukee, WI |
| | CRODAFOS SG | PPG-5 ceteth-10 phosphate | Croda Inc. | Parsipanny, NJ |
| CHG | Chlorhexidine gluconate | chlorhexidine gluconate (concentration varies by lot: 18.9%, 18.8%, 18.5%) | MedChem Laboratories | Galena, IL |
| PHMB | COSMOCIL CQ 20% | Polyhexamethylene- biguanide | ICI Americas | Wilmington, DE |
| | CRODAMOL GTCC | glyceryltricaprate/ caprylate | Croda | Parsippany, NJ |
| DIPS | DERMOL DIPS | diisopropyl sebacate | Alzo | Sayreville, NJ |
| DPG LO+ | DIPROPYLENE GYCOL LO+ | dipropylene glycol 99.5% | Dow Chemical Company | Midland, MI |
| DOSS | 50% DOSS | 50% Dioctyl Sodium Sulfosuccinate in PEG-400 | Cytec Industries Inc. | West Paterson, NJ |
| | DOWANOL DB | diethylene glycol butyl ether | Aldrich | Milwaukee, WI |
| EDTA | EDTA disodium | ethylene diamine tetraacetic acid, disodium | Aldrich | Milwaukee, WI |

TABLE 1-continued

GLOSSARY of COMPONENTS

| Abrev. (optional) | Trade name | Description | Source | Address |
|---|---|---|---|---|
| | FINSOLV TN glycerin (glycerol) | $C_{12}$-$C_{15}$ benzoate ester glycerin (glycerol) | Finetex, Inc. Aldrich | Spencer, NC Milwaukee, WI |
| | Glycerin ether | $C_{10}H_{23}$ glycerin ether | Preparation described in Example 83 | |
| | HEALTHSHIELD | Silver Zeolite | Healthshield | W. Hartford, CT |
| | HIPURE 88 | Lactic acid (88%) | Purac America | Lincolnshire, IL |
| | HIPURE 90 | Lactic acid (90%) | Purac America | Lincolnshire, IL |
| | HOSTAPUR SAS 93G | Sodium C14-C17 Sec alkyl sulfonate, 93% solids | Clariant Corp. | Charlotte, NC |
| | HOSTAPUR SAS 60 | Sodium C14-C17 Sec alkyl sulfonate, 60% solids | Clariant Corp | Charlotte, NC |
| $H_2O_2$ | Hydrogen peroxide | Hydrogen peroxide 30.6% | Aldrich Chemical | Milwaukee, WI |
| | INCROQUAT BEHENYL TMS | cationic emulsifying wax | Croda | Parsippany, NJ |
| | IRGASAN DP300 | Triclosan | Ciba | Tarrytown, NY |
| IPA | Isopropyl Alcohol | Isopropanol, reagent grade | VWR International | West Chester, PA |
| IPP | Isopropyl palmitate | Isopropyl palmitate | Sigma Aldrich | St. Louis, MO |
| HPMC M CS | KLUCEL M CS | Hydroxypropyl methylcellulose | Aqualon Division of Hercules Inc. | Wilmington, DE |
| HPMC M Pharma | KLUCEL M Pharma | Hydroxypropyl cellulose, pharma grade | Aqualon Division of Hercules Inc. | Wilmington, DE |
| | Lactic acid (dilute) | Lactic acid (10% in DI water) | diluted from Hipure 88 | — |
| | Lauric acid | Lauric acid | Aldrich Chemical | Milwaukee, WI |
| GML | LAURICIDIN | Glycerol monolaurate | MedChem Laboratories, Inc. | Galena, IL |
| | LUROL ASY | alkyl phosphate | George A. Goulston | Monroe, NC |
| | LUTROL F68 NF | Poloxamer 188 | BASF | Mt. Olive, NJ |
| | LUTROL L44 NF | Poloxamer 124 | BASF | Mt. Olive, NJ |
| M90G | M90G | Methoxy Polyethylene Glycol 400 Methacrylate (EQ 9 mol) | Shin-Nakamura Chemicals | Wakayama City, Japan |
| | MACKAM 50-SB | Lauramidopropyl hydroxysultaine (Cocamidopropyl Hydroxysultaine) | McIntyre Group Ltd. | University Park, IL |
| | Malic Acid | Malic Acid | Aldrich Chemical | Milwaukee, WI |
| | Mandelic Acid | Mandelic Acid | Sigma-Aldrich | St. Louis, MO |
| | Magnesium sulfate | $MgSO_4$ $7H_2O$ | Aldrich Chemical | Milwaukee, WI |
| | Methyl paraben | methyl paraben | Glenn Corp | St. Paul, MN |
| | Mineral oil | mineral oil USP | Paddock Labs | Minneapolis, MN |
| PCMX | OTTASEPT | parachlorometaxylenol | Lonza/Happi | Ramsey, NJ |
| MPEG | PEG 475 | poly(ethyleneglycol) methyl ether methacrylate (MW475) | Sigma Aldrich | St. Louis, MO |
| | 2-phenoxyethanol | 2-phenoxyethanol | Aldrich | Milwaukee, WI |
| CDM | Phospholipid CDM | phosphatidyl PG-dimonium chloride | Uniqema | Patterson, NJ |
| | PHYTOLANE | Squalane | Barnet Products Corp. | Englewood Cliffs, NJ |
| | PLURONIC P-65 | nonionic difunctional block copolymer of polyoxyethylene and polyoxypropylene | BASF Corp. | Mount Olive, NJ |

TABLE 1-continued

GLOSSARY of COMPONENTS

| Abrev. (optional) | Trade name | Description | Source | Address |
|---|---|---|---|---|
| | PLURONIC F-68 | poloxamer 188; mixture of polyoxyethylene and polyoxypropylene; a non-ionic surfactant | BASF Corp. | Mount Olive, NJ |
| | PLURONIC F-127 | poloxamer 407; block copolymer of ethylene oxide/propylene oxide | BASF Corp. | Mount Olive, NJ |
| | (emulsifying) Polymer GG | 80/20 IOA/MPEG (25% polymer in IPP) | Prepared as described below* | St. Paul, MN |
| | Polymer QQ | 40/40/20 SMA/IOA/M90G (25% polymer in IPP) | Prepared as described below* | St. Paul, MN |
| | POLAWAX | Emulsifying wax | Croda | Parsippany, NJ |
| | POLYSTEP B12 | Sodium laureth-4 sulfate | Stepan Company | Northfield, IL |
| PVPI | Povidone Iodine | Providone Iodine USP | International Specialty Products | Wayne, NJ |
| PVP K90 | Polyvinylpyrrolidone K90 | 2-Pyrrolidone, 1 Ethenyl-, Homopolymer | International Specialty Products | Wayne, NJ |
| | propyl paraben | propyl paraben | KIC Chemicals | Armonk, NY |
| | Propylene glycol | 1,2 propanediol | JT Baker | Phillipsburg, NJ |
| | Propylene glycol monocaprate | propylene glycol monocaprate | Uniqema | Patterson, NJ |
| EHL | PURASOLV EHL | 2-ethylhexyl lactate | PURAC America | Lincolnshire, IL |
| | RITA TRICLOSAN | Triclosan | Rita Corp. | Crystal Lake, IL |
| | RITAPRO 300 | emulsifying wax | Rita Chemicals | Woodstock, IL |
| SMA | ROCRYL 330 | Stearyl Methacrylate | Rohm and Haas | Philadelphia, PA |
| DMAEMA Q | SALCARE SC95 | Homopolymer of methacryloyloxyethyl trimethyl ammonium chloride (Polyquaternium 37) | Allied Colloids Inc. | Suffolk, VA |
| | SENSIVA SC 50 | C8 glycerin ether | Schuklke & Mayr GmbH | Norderstedt, Germany |
| | Silver Nitrate | Silver Nitrate | Aldrich | Milwaukee, WI |
| Pet | SNOW WHITE | White Petrolatum USP | Penreco | Karns City, PA |
| NaOH 10N | Sodium Hydroxide | 10N NaOH | Sigma Aldrich | Milwaokee, WI |
| NaOH 5N | Sodium Hydroxide | 5N NaOH | Sigma Aldrich | Milwaokee, WI |
| | Tartaric acid | Tartaric acid | Aldrich Chemical | Milwaokee, WI |
| | TWEEN 20 | Polyoxyethylene-sorbitan monolaurate; Polysorbate 20 | Sigma Aldrich | Milwaokee, WI |
| | White beeswax | White beeswax | Acros Organics | Belgium |
| | VAZO-67 | 2,2'-azobis(2-methylbutanenitrile) | Dupont | Wilmington, DE |

*Emulsifying polymer GG was prepared in the following manner. A mixture of isooctyl acrylate (IOA, 21.6 parts), and MPEG (5.4 parts) [80/20 IOA/MPEG, respectively, weight ratio] was dissolved in ethyl acetate (33 parts) that contained VAZO 67 radical initiator (0.081 part). The solution was contained in a flint glass bottle that was closed with a Teflon-lined metal cap and maintained at 65° C. for 50 hours. Monomer conversion (determined by percent solids measured by loss on drying at 105° C.) was essentially complete at 50 hours. Solvent exchange was accomplished by adding isopropyl palmitate (IPP) to the ethyl acetate solution and stripping the lower boiling ethyl acetate on a ROTOVAP evaporator to obtain a 25 weight percent solution of polymer in IPP.

*Polymer QQ was prepared in the following manner. A mixture of SMA (10.8 parts), IOA (10.8 parts), and M90G (5.4 parts) [80/20, respectively, weight ratio] was dissolved in ethyl acetate (33 parts) that contained VAZO 67 radical initiator (0.081 part). The solution was contained in a flint glass bottle that was closed with a Teflon-lined metal cap and maintained at 65° C. for 50 hours. Monomer conversion (determined by percent solids measured by loss on drying at 105° C.) was essentially complete at 50 hours. Solvent exchange was accomplished by adding isopropyl palmitate (IPP) to the ethyl acetate solution and stripping the lower boiling ethyl acetate on a ROTOVAP evaporator to obtain a 25 weight percent solution of polymer in IPP.

Preparation of Examples

Control Examples C1 and C2

Control compositions of 250 grams each, containing no antimicrobial agents, were prepared using the components shown in Table 2 for each example. Carbowax 1450 PEG was heated in an oven until melted in a first glass container. In a second glass container Glycerin, Carbowax 400 and Aerosol OT-75 DOSS were also heated to 70° C. Contents of the second container were added to the first container, swirled by hand to mix and reheated to 70° C. The composition was removed from the oven and allowed to cool to at least approximately 40° C., while mixing on a roller.

Examples 1-6

Antimicrobial compositions of 250 grams each was were prepared using the components shown in Table 2. The respective antimicrobials: PCMX, Irgasan DP300 (triclosan), lauric acid, or benzalkonium chloride were combined with other components: glycerin, Carbowax 400 and Aerosol OT-75 (or Complemix) in a glass container and heated in an oven at approximately 70° C. Carbowax 1450 PEG was placed in a second glass container heated to its melting point and then added to the first container. The composition was then swirled by hand to mix and then reheated again to 70° C. The composition was allowed to cool on rollers to approximately 40° C. then transferred into jars, and sealed.

The control samples showed no antimicrobial efficacy in 2.5 min against the test organisms. Those examples, prepared in hydrophilic vehicles, had 2.9 log or greater kill in 2.5 minutes for both MRSA (Gram positive) and E. coli (Gram negative) bacteria. Addition of a lactic acid enhancer to Example 5 improved the antimicrobial efficacy against E. coli by greater than 3.7 log when compared to Example 4. Example 5 showed complete kill of E. coli. A combination of a quaternary ammonium compound (benzalkonium chloride) with triclosan at a significantly reduced concentration in Example 3 still provided 3.9 log kill against MRSA in 2.5 minutes and 5.2 log kill against E. coli in 2.5 min. Example 6 shows that an alkyl carboxylic acid in a hydrophilic vehicle is capable of achieving complete kill against both MRSA and E. coli in 2.5 minutes or less.

TABLE 2

| Component | C1 | C2 | 1 | 2 | 3 | 4 | 5 | 6 |
|---|---|---|---|---|---|---|---|---|
| | | | w/w % amount of components | | | | | |
| OTTASEPT (PCMX) | — | — | 2.00 | — | — | — | — | — |
| 2-phenoxyethanol | — | — | 0.50 | 0.50 | — | 0.50 | 0.50 | |
| IRGASAN DP300 | — | — | — | 2.00 | 0.50 | 2.00 | 2.00 | |
| Benzalkonium Chloride | — | — | — | — | 0.13 | — | — | |
| Lauric Acid | | | | | | | | 3.00 |
| HIPURE 88 | — | — | — | — | — | — | 1.00 | 1.00 |
| CARBOWAX 400 | 61.78 | 60.96 | 59.00 | 59.00 | 58.00 | 59.22 | 58.79 | 58.79 |
| CARBOWAX 1450 | 16.75 | 16.53 | 16.00 | 16.00 | 17.00 | 16.2 | 15.96 | 15.96 |
| Glycerin | 21.47 | 21.18 | 20.50 | 20.5 | 20.00 | 20.75 | 20.42 | 20.42 |
| AEROSOL OT-75 (DOSS) | — | 1.33 | 2.00 | 2.00 | — | 1.33 | 1.33 | |
| COMPLEMIX | | | | | | | | 1.00 |
| PLURONIC P-65 | — | — | — | — | 4.37 | — | 0 | |
| Total | 100.0 | 100.0 | 100.0 | 100.0 | 100.0 | 100.0 | 100.0 | 100.0 |
| Antimicrobial efficacy results: | | | | | | | | |
| 2.5 min MRSA test 1 | −0.8 | −0.2 | 6.6* | 3.3 | 3.4 | 6.8* | 5.8 | 6.7* |
| 2.5 min MRSA test 2 | −0.8 | −0.3 | 6.6* | 2.6 | 4.3 | 6.8* | 5.8 | 6.7* |
| Average | −0.8 | −0.3 | 6.6* | 2.9 | 3.9 | 6.8* | 5.8 | 6.7* |
| 2.5 min E coli test 1 | −0.5 | 0.1, 0.9 | 4.7 | 4.2 | 4.5 | 3.1 | 6.9* | 7.0* |
| 2.5 min E coli test 2 | −0.5 | 0.1, 0.7 | 4 | 4.1 | 5.9 | 3.3 | 6.9* | 7.0* |
| Average | −0.5 | 0.5** | 4.4 | 4.1 | 5.2 | 3.2 | 6.9* | 7.0* |

*Complete Kill.
**Average of 2 sets of 2 results.
No testing performed at 10 minutes for MRSA or E coli.

Examples C3, C4, 7-11

Control Examples C3 and C4, containing no antimicrobial agents, as well as antimicrobial compositions, Examples 7-10, were prepared in amounts of 250 grams each (Example 11 was prepared in an amount of 100 grams) using the components shown in Table 3 for each example. Petrolatum was added to a glass container and heated in an oven to approximately 70° C. All other components were added to a second glass container and also heated in an oven at approximately 70° C. Just prior to mixing the contents of the two containers together, AEROSOL OT75 (where applicable) was first added to the second container. The mixture of all components was then mixed using a high shear rotor/stator Silverson homogenizer on high speed for 1 minute. Mixing was continued at low speed using a Gast overhead air mixer with radial flow impeller until just before the composition congealed at approximately 40° C. The compositions were removed from the mixer, poured into jars, and sealed.

Examples 7 and 8 are compositions having a hydrophobic vehicle, with a hydrophilic component and a surfactant. Example 7 had greater than 4.5 log kill efficacy against both MRSA and E. coli at 2.5 min and Example 8 had greater than 4 log kill efficacy against MRSA at 10 min. Example 10 had an additional alphahydroxy acid enhancer, which improved the antimicrobial efficacy against MRSA at both 2.5 and 10 minutes. Examples C3 and C4 are controls which indicate the compositions without triclosan had less than 2 log kill against MRSA and E. coli at 10 min.

Example 12

Example 12, also shown in Table 3, was prepared in the same manner as Examples 7-11, except the IRGASAN DP300 (triclosan) was added to the Petrolatum prior to heating. Example 12 contains no glycerin (hydrophilic) component and did not achieve 2 log kill. Example 8, which had a similar composition to Example 12, did contain glycerin and as mentioned above, Example 8 had greater than 4 log kill efficacy against MRSA at 10 minutes.

in a third glass container. The water was then added to the second container and mixed using a high shear rotor/stator Silverson homogenizer on high speed for 1 minute. The contents of the first container were then added to the new mixture of the second container and again mixed using a high shear rotor/stator Silverson homogenizer on high speed for 1 minute. The composition was allowed to cool on rollers to approximately 40° C. Example 13 is an oil-in-water emulsion containing triclosan which did not achieve 2 log

TABLE 3

| Component | \multicolumn{8}{c}{Example Numbers} | | | | | | | |
|---|---|---|---|---|---|---|---|---|
| | C3 | C4 | 7 | 8 | 9 | 10 | 11 | 12 |
| | \multicolumn{8}{c}{w/w % amount of components} | | | | | | | |
| 2-phenoxyethanol | 0.5 | — | 0.5 | 0.5 | 0.5 | 0.5 | 0.5 | 0.5 |
| Irgasan DP300 | — | — | 2 | 2 | 2 | 2 | 2 | 2 |
| HIPURE 88 | 1 | 1 | — | — | — | 1 | 1 | — |
| Propylene glycol | — | — | — | — | — | — | 20 | — |
| Glycerin | 20 | 20 | 10 | 20 | 20 | 20 | — | — |
| SNOW WHITE | 75.17 | 75.67 | 81.2 | 76.17 | 77.5 | 73.17 | 73.17 | 96.17 |
| COMPLEMIX (DOSS) | 1.33 | 1.33 | — | — | — | — | — | — |
| AEROSOL OT-75 | — | — | 1.3 | 1.33 | — | 1.33 | 1.33 | 1.33 |
| PLURONIC P-65 | 2 | 2 | 5 | — | — | 2 | 2 | — |
| Water | — | — | — | — | — | — | — | — |
| Total | 100 | 100 | 100 | 100 | 100 | 100 | 100 | 100 |
| \multicolumn{9}{c}{Antimicrobial efficacy results:} | | | | | | | | |
| 2.5 min MRSA test 1 | 0.8 | 1.6 | 4.2 | −0.8 | 0 | 2.2 | NT | −1.6 |
| 2.5 min MRSA test 2 | 0.7 | 1.8 | 4.8 | 0.5 | −0.9 | 3.6 | NT | −1.7 |
| Average | 0.8 | 1.7 | 4.5 | −0.2 | −0.5 | 2.9 | NT | −1.6 |
| 2.5 min E coli test 1 | NT | NT | 5.6 | 0.2 | 0.1 | 0.7 | NT | 0 |
| 2.5 min E coli test 2 | NT | NT | 5.3 | 0.2 | −0.2 | 1.3 | NT | 0 |
| Average | — | — | 5.5 | 0.2 | −0.1 | 1 | NT | 0 |
| 10 min MRSA test 1 | 1.6 | 1.7 | NT | 4.9 | 0.3 | 4.6 | NT | 0.9 |
| 10 min MRSA test 2 | 1.4 | 1.7 | NT | 3.3 | 0.4 | 6.8 | NT | 0 |
| Average | 1.5 | 1.7 | — | 4.1 | 0.3 | 5.7 | NT | 0.5 |
| 10 min E coli test 1 | −0.7 | −0.7 | NT | 0.9 | 0.4 | 1.2 | NT | 0.2 |
| 10 min E coli test 2 | −0.7 | 0.1 | NT | 1 | 0.3 | 1.1 | NT | −0.4 |
| Average | −0.7 | −0.3 | — | 0.9 | 0.4 | 1.1 | NT | −0.1 |

NT = not tested

Examples 13-17

Antimicrobial compositions of 250 grams were prepared using the components shown in Tables 3 and 4 for each example. IRGASAN DP300, HIPURE 88 (lactic acid) and glycerin were added to a first glass container and heated to 70° C. in an oven. POLAWAX, mineral oil, INOCROQUAT BEHENYL TMS, 2-pheoxyethanol, lactic acid, EDTA, COMPLEMIX, AEROSOL OT-75 and PLURONIC P-65 were added to a second glass container and also heated to 70° C. in an oven. Water was heated in the oven to 70° C.

kill at 10 minutes for either MRSA or E. coli. As shown in Example 14, addition of an anionic surfactant (DOSS), however, improved the antimicrobial efficacy to 5.3 log against MRSA at 10 minutes. Addition of both an anionic surfactant (DOSS) and an enhancer (lactic acid) improved the antimicrobial efficacy for Example 15 to greater than 7 log at 10 min against MRSA. In Example 16, addition of a chelator (EDTA, 14800 μM), even in the absence of an anionic surfactant, improved the antimicrobial efficacy against MRSA to 4.7 log at 10 minutes. Example 17 had no 2-phenoxyethanol enhancer and did not achieve a 2 log kill at 10 minutes against either MRSA or E. coli.

TABLE 4

| Component | \multicolumn{5}{c}{Example Numbers} | | | | |
|---|---|---|---|---|---|
| | 13 | 14 | 15 | 16 | 17 |
| | \multicolumn{5}{c}{w/w % amount of components} | | | | |
| 2-phenoxyethanol | 0.50 | 0.50 | 0.50 | 0.50 | — |
| IRGASAN DP300 | 2.00 | 2.00 | 2.00 | 2.00 | 2.00 |
| HIPURE 88 (lactic acid) | — | — | 1.00 | — | — |
| EDTA disodium | — | — | — | 0.50 | — |
| Glycerin | 20.00 | 20.00 | 20.00 | 20.00 | 20.00 |
| POLAWAX | 10.00 | 12.00 | 12.00 | 12.00 | 12.00 |
| INCROQUAT BEHENYL TMS | 3.00 | — | — | — | — |

TABLE 4-continued

|  | Example Numbers | | | | |
| --- | --- | --- | --- | --- | --- |
|  | 13 | 14 | 15 | 16 | 17 |
| Component | w/w % amount of components | | | | |
| Mineral oil | 5.00 | 5.00 | 5.00 | 5.00 | 5.00 |
| COMPLEMIX (DOSS) | — | — | — | 1.00 | 1.00 |
| AEROSOL OT-75 (DOSS) | — | 1.33 | 1.33 | — | — |
| Water | 59.50 | 59.17 | 58.17 | 59.00 | 60.00 |
| Total | 100.0 | 100.0 | 100.0 | 100.0 | 100.0 |
| Antimicrobial efficacy results: | | | | | |
| 2.5 min MRSA test 1 | −0.4 | 0.4, 4.3, 0.3 | 1.5 | 1.0 | 0.3 |
| 2.5 min MRSA test 2 | −0.6 | 0.5, 2.9, 0.3 | 2.4 | 1.94, 0.2 | 0.6 |
| Average | −0.5 | 1.5*** | 1.9 | 1.1# | 0.4 |
| 2.5 min *E coli* test 1 | 0.3 | 0.2 | 0.0 | 1.0 | 0.6 |
| 2.5 min *E coli* test 2 | 0.3 | 0.1 | 0.1 | 0.7 | 0.1 |
| Average | 0.3 | 0.2 | 0.0 | 0.8 | 0.4 |
| 10 min MRSA test 1 | 0.7 | 5.1 | 7.2 | 3.6 | 0.3 |
| 10 min MRSA test 2 | 1.4 | 5.5 | 7.2 | 5.8 | 0.8 |
| Average | 1.1 | 5.3 | 7.2 | 4.7 | 0.5 |
| 10 min *E coli* test 1 | −0.5 | 0.6 | 2.8 | 0.9 | NT |
| 10 min *E coli* test 2 | 0.2 | −0.5 | 2.9 | 0.9 | NT |
| Average | −0.2 | 0.0 | 2.9 | 0.9 | — |

***Average of 3 sets of 2
Average of 3 results

Control Examples C5-C6

Control compositions of 250 grams each, containing no antimicrobial agents, were prepared using the components shown in Table 5 for each example. CARBOWAX 1450 PEG was heated in an oven until melted in a first glass container. In a second glass container Glycerin, CARBOWAX 400 and AEROSOL OT-75 DOSS were also heated to 70° C. Contents of the second container were added to the first container, swirled by hand to mix and reheated to 70° C. The composition was removed from the oven and allowed to cool to at least approximately 40° C., while mixing on a roller.

Examples 18-26

Antimicrobial compositions of 125 grams were prepared using the components shown in Tables 5 and 6. For examples 18-23, the antiseptic component: Silver Zeolite, phospholipid CDM, IRGASAN DP300, benzethonium chloride, or benzalkonium chloride was combined with PLURONIC P-65 and glycerin in a first glass container and heated to 70° C. in an oven. CARBOWAX 1450 was heated to melting in a separate container then added to the first container along with the remaining components, swirled by hand to mix and then reheated to 70° C. in the oven. The composition was removed from the oven allowed to cool to approximately 40° C., while mixing on rollers, then transferred into jars and sealed. Examples 24-25, which contained PHMB, and example 26, which contained CHG, were prepared as described above with the exception that there was no initial heating required and these antiseptics were added after all other components were combined.

Examples 18-26 comprised hydrophilic vehicles containing a mixture of PEG compounds and glycerin. Example 18 and 19 incorporated Phospholipid CDM, an antimicrobial quaternary ammonium compound. The antimicrobial efficacy against both MRSA and *E. coli* was greater than 3 log at 2.5 minutes for Example 18. Example 19 further incorporated EDTA as an enhancer. Despite the anionic nature of this enhancer, it increased the antimicrobial efficacy of this quaternary ammonium compound. Example 19 killed 3.9 log MRSA and 7.1 log(complete kill) against *E. coli* at 2.5 minutes. Examples 20 and 23 contained the antimicrobial quaternary ammonium compounds benzethonium chloride and benzalkonium chloride respectively. These compositions exhibited greater than 2 log kill against MRSA and *E. coli* after 2.5 minutes exposure. Example 22 used a combination of a quaternary ammonium compound (benzalkonium chloride) and a phenolic antiseptic (triclosan), both at relatively low concentration, and exhibited 3.9 log kill against MRSA and 5.2 log kill against *E. coli* after 2.5 minutes exposure. Example 21 used a silver/zeolite complex (HEALTHSHIELD). The composition did not achieve 2 log kill against either MRSA or *E. coli* after a 2.5 minutes exposure possibly because the silver is not released rapidly enough. In contrast, Example 27 (below), which used silver nitrate, achieved 6.3 log kill against MRSA and 4.8 log kill against *E. coli* after a 2.5 min. exposure. Examples 24 and 25 used PHMB at 0.2 and 5% respectively. These compositions achieved complete kill (6.8 log) against MRSA and at least 4.8 log kill against *E. coli* after a 10 min. exposure. Example 26 incorporated 1.9% total CHG (18.9% solution× 10.4 w/w %=1.9%) and this composition killed 3.1 log MRSA and 6.1 log *E. coli* after a 2.5 min. exposure.

Example 27

An antimicrobial composition of 250 grams was prepared using the components shown in Table 6. CARBOWAX 1450 was preheated to melting (approximately 65° C.), in an oven, in a glass container. All other components, except silver nitrate, were combined with the CARBOWAX 1450 and swirled by hand to mix. The composition was allowed to cool to approximately 50° C. and then the silver nitrate was added. The solution was allowed to further cool to approximately 40° C., and then transferred to storage jars protected from light.

TABLE 5

| Component | C5 | C6 | 18 | 19 | 20 | 21 | 22 | 23 |
|---|---|---|---|---|---|---|---|---|
| | \multicolumn{8}{c}{w/w % amount of components} | | | | | | | | |
| HEALTHSHIELD | — | — | — | — | — | 3.00 | — | — |
| Phospholipid CDM | — | — | 3.00 | 3.00 | — | — | — | — |
| 2-phenoxyethanol | — | — | — | — | 0.50 | — | — | — |
| IRGASAN DP300 | — | — | — | — | — | — | 0.50 | — |
| Benzethonium Chloride | — | — | — | — | 0.30 | — | — | — |
| Benzalkonium Chloride | — | — | — | — | — | — | 0.13 | 2.50 |
| EDTA | — | — | — | 0.50 | — | — | — | — |
| CARBOWAX 400 | 61.78 | 60.96 | 59.00 | 58.50 | 59.00 | 57.00 | 58.00 | 59.00 |
| CARBOWAX1450 | 16.75 | 16.53 | 16.00 | 16.00 | 17.20 | 15.00 | 17.00 | 16.00 |
| Glycerin | 21.47 | 21.18 | 20.00 | 20.00 | 20.00 | 20.00 | 20.00 | 20.50 |
| PLURONIC P-65 | — | — | 2.00 | 2.00 | 3.00 | 5.00 | 4.40 | 2.00 |
| AEROSOL OT-75 | — | 1.33 | — | — | — | — | — | — |
| Total | 100.0 | 100.0 | 100.0 | 100.0 | 100.0 | 100.0 | 100.0 | 100.0 |
| \multicolumn{9}{c}{Antimicrobial efficacy results:} | | | | | | | | |
| 2.5 min MRSA test 1 | −0.8 | −0.2 | 3.2 | 3.9 | 2.1 | 0.0 | 3.4 | 6.6 |
| 2.5 min MRSA test 2 | −0.8 | −0.3 | 3.2 | 3.8 | 2.2 | 0.1 | 4.3 | 5.6 |
| Average | −0.8 | −0.3 | 3.2 | 3.9 | 2.1 | 0.0 | 3.9 | 6.1 |
| 2.5 min E coli test 1 | −0.5 | 0.1, 0.9 | 3.5 | 7.1* | 4.8 | 0.5 | 4.5 | 5.0 |
| 2.5 min E coli test 2 | −0.5 | 0.1, 0.9 | 4.3 | 7.1* | 5.0 | 0.2 | 5.9 | 5.4 |
| Average | −0.5 | 0.5** | 3.9 | 7.1* | 4.9 | 0.3 | 5.2 | 5.2 |
| 10 min MRSA test 1 | NT | NT | NT | NT | NT | 1.5 | NT | NT |
| 10 min MRSA test 2 | NT | NT | NT | NT | NT | 0.6 | NT | NT |
| Average | — | — | — | — | — | 1.1 | — | — |
| 10 min E coli test 1 | NT | NT | NT | NT | NT | 0.1 | NT | NT |
| 10 min E coli test 2 | NT | NT | NT | NT | NT | 0.2 | NT | NT |
| Average | — | — | — | — | — | 0.2 | — | — |

*Complete Kill.
**Average of 2 sets of 2 results.

TABLE 6

| Component | 24 | 25 | 26 | 27 |
|---|---|---|---|---|
| | \multicolumn{4}{c}{w/w % each components} | | | |
| Silver Nitrate | — | — | — | 0.50 |
| PHMB (COSMOCIL CQ 20%) | 0.20 | 5.00 | — | — |
| CHG 18.5% | — | — | 10.42 | — |
| CARBOWAX 400 | 58.19 | 57.00 | 55.34 | 58.55 |
| CARBOWAX 1450 | 16.56 | 15.00 | 15.01 | 15.41 |
| Glycerin | 20.06 | 18.00 | 19.23 | 20.54 |
| PLURONIC P-65 | 5.00 | 5.00 | — | 5.00 |
| Total | 100.0 | 100.0 | 100.0 | 100.0 |
| \multicolumn{5}{c}{Antimicrobial efficacy results:} | | | | |
| 2.5 min MRSA test 1 | 1.2 | 2.1 | 3.0 | 5.8 |
| 2.5 min MRSA test 2 | 1.4 | 1.1 | 3.1 | 6.8 |
| Average | 1.3 | 1.6 | 3.1 | 6.3 |
| 2.5 min E coli test 1 | 2.5 | 2.5 | 7.1 | 3.9 |
| 2.5 min E coli test 2 | 2.1 | 4.1 | 5.1 | 5.8 |
| Average | 2.3 | 3.3 | 6.1 | 4.8 |
| 10 min MRSA test 1 | 6.8* | 6.8* | NT | NT |
| 10 min MRSA test 2 | 6.8* | 6.8* | NT | NT |
| Average | 6.8* | 6.8* | — | — |
| 10 min E coli test 1 | 4.5 | 4.4 | NT | NT |
| 10 min E coli test 2 | 5.1 | 5.5 | NT | NT |
| Average | 4.8 | 4.9 | — | — |

*Complete Kill.

Examples 28-31

Antimicrobial compositions of 120 grams each were prepared using the components shown in Table 7 for each example. Petrolatum was added to a first glass container and heated in an oven to approximately 70° C. All other components were added to a second glass container and also heated in an oven at approximately 70° C. The mixture of components in the second container was then added to the first container and then further mixed using a high shear rotor/stator Silverson homogenizer on high speed for 1 minute. Mixing was continued at low speed using a Gast overhead air mixer with radial flow impeller until just before the composition congealed at approximately 40° C. The compositions were removed from the mixer, poured into jars, and sealed.

Examples 28-31 were formulated in a hydrophobic vehicle. Example 28 incorporated CHG as the antiseptic and glycerin as a hydrophilic component and achieved 4.4 and 7.1 log kill against MRSA and E. coli respectively after a 2.5 min. exposure. Examples 29 and 30 had Phospholipid CDM as the antiseptic and glycerin as a hydrophilic component. Example 29 further incorporated a surfactant, PLURONIC P-65. The antimicrobial efficacy of Example 29 was 4.2 log and 2.9 log kill against MRSA and E. coli, respectively. The antimicrobial efficacy of Example 30 was 5.7 log and 6.3 log against MRSA and E. coli, respectively.

Examples 32-33

Examples 32-33, also shown in Table 7, were prepared in the same manner as Examples 28-31, above, except the benzalkonium chloride was added to the Petrolatum prior to heating. Examples 28-33 use petrolatum as the hydrophobic vehicle.

Example 32, which incorporated glycerin as a hydrophilic component achieved complete kill against both MRSA and E. coli after a 2.5 min. exposure. Example 33 which did not incorporate a hydrophilic component did not achieve 2 log kill for either MRSA nor E. coli after a 2.5 min exposure.

TABLE 7

| Components | \multicolumn{6}{c}{Example Numbers} |
|---|---|---|---|---|---|---|
| | 28 | 29 | 30 | 31 | 32 | 32 |
| | \multicolumn{6}{c}{w/w % amount of components} |
| Phospholipid CDM | — | 3.00 | 3.00 | 3.00 | — | — |
| Benzalkonium Chloride | — | — | — | — | 2.50 | 2.50 |
| CHG 18.5% | 11.11 | — | — | — | — | — |
| Glycerin | 16.00 | 25.00 | 25.00 | — | 25.00 | — |
| SNOW WHITE | 67.90 | 70.00 | 72.00 | 95.00 | 70.50 | 95.50 |
| PLURONIC P-65 | 5.00 | 2.00 | — | 2.00 | 2.00 | 2.00 |
| Total | 100.0 | 100.0 | 100.0 | 100.0 | 100.0 | 100.0 |
| \multicolumn{7}{c}{Antimicrobial efficacy results:} |
| 2.5 min MRSA test 1 | 4.2 | 4.6 | 4.8 | 0.6 | 6.7* | 1.9 |
| 2.5 min MRSA test 2 | 4.5 | 3.7 | 6.6 | 0.8 | 6.7* | 1.7 |
| Average | 4.4 | 4.2 | 5.7 | 0.7 | 6.7* | 1.8 |
| 2.5 min *E coli* test 1 | 7.1* | 2.5, 2.6 | 5.7 | 0.7 | 6.7* | 0.7 |
| 2.5 min *E coli* test 2 | 7.1* | 3.5, 3.0 | 7.0 | 0.9 | 6.7* | 1.4 |
| Average | 7.1* | 2.9** | 6.3 | 0.8 | 6.7* | 1.1 |

No antimicrobial efficacy testing was performed at 10 minutes for MRSA or *E coli*.
*Complete kill.
**Average of two sets of two results.

Examples C7, C8 and 34-35

Control examples C7 and C8, containing no antiseptic and CHG antimicrobial compositions, examples 34 and 35, were prepared in amounts of 250 grams using the components shown in Table 8 for each example. Petrolatum was used as a hydrophobic vehicle and added to a first glass container and heated in an oven to approximately 70° C. All other components were added to a second glass container and also heated in an oven at approximately 70° C. The mixture of components in the second container was then added to the first container and then further mixed using a high shear rotor/stator Silverson homogenizer on high speed for 1 minute. Mixing was continued at low speed using a Gast overhead air mixer with radial flow impeller until just before the composition congealed at approximately 40° C. The compositions were removed from the mixer, poured into jars, and sealed.

Examples 34 and 35 used CHG as the antiseptic component. Note that the CHG was incorporated as a solution in water. Examples C7 and C8 were the vehicle controls. Example 34 had 2.5 log kill and 4.8 log kill against MRSA and *E. coli* respectively after 2.5 minutes exposure.

Examples 36-38

Antimicrobial compositions of 120 grams each were prepared using the components shown in Table 8. Petrolatum was added to a first glass container and heated in an oven to approximately 70° C. All other components except CHG were added to a second glass container and heated in an oven at approximately 50° C. The contents of the second container were added to the first container while hand swirling the container to mix. CHG was then added and the mixture was swirled by hand to mix.

Note that CHG, the antiseptic component, was incorporated as a solution in water. Several enhancers were evaluated including lactic acid/propyl paraben and a DOWANOL ether. All three Examples 36-38 achieved at least 2.5 log kill against both MRSA and *E. coli* after a 10-minute exposure.

TABLE 8

| Components | \multicolumn{7}{c}{Example Numbers} |
|---|---|---|---|---|---|---|---|
| | C7 | C8 | 34 | 35 | 36 | 37 | 38 |
| | \multicolumn{7}{c}{w/w % amount of components} |
| CHG 18.5% | — | — | 11.11 | 10.58 | 10.58 | 10.60 | 10.60 |
| glycerin | — | 20.00 | 20.00 | — | 20.00 | 20.00 | 20.00 |
| Propylene glycol | 20.00 | — | — | — | — | — | — |
| SNOW WHITE | 78.00 | 78.00 | 66.89 | 87.40 | 67.02 | 62.40 | 57.40 |
| PLURONIC P-65 | 2.00 | 2.00 | 2.00 | 2.00 | 2.00 | 2.00 | 2.00 |
| HIPURE 88 | — | — | — | — | 0.20 | — | — |
| propyl paraben | — | — | — | — | 0.20 | — | — |
| DOWANOL DB | — | — | — | — | — | 5.00 | 10.00 |
| Total | 100.0 | 100.0 | 100.0 | 100.0 | 100.00 | 100.00 | 100.00 |
| \multicolumn{8}{c}{Antimicrobial efficacy results:} |
| 2.5 min MRSA test 1 | 1.6 | −0.1 | 2.6 | NT | 2.0 | NT | NT |
| 2.5 min MRSA test 2 | 1.8 | −0.1 | 2.4 | NT | 2.5 | NT | NT |
| Average | 1.7 | −0.1 | 2.5 | — | 2.2 | — | — |
| 2.5 min *E coli* test 1 | NT | −0.1 | 5.0 | NT | NT | NT | NT |
| 2.5 min *E coli* test 2 | NT | −0.1 | 4.5 | NT | NT | NT | NT |
| Average | — | −0.1 | 4.8 | — | — | — | — |
| 10 min MRSA test 1 | NT | NT | NT | 3.6 | 3.7 | 3.1 | 2.3 |
| 10 min MRSA test 2 | NT | NT | NT | 3.3 | 3.0 | 3.0 | 2.4 |
| Average | — | — | — | 3.5 | 3.3 | 3.1 | 2.3 |
| 10 min *E coli* test 1 | NT | NT | NT | NT | 3.9 | 2.9 | 2.5 |
| 10 min *E coli* test 2 | NT | NT | NT | NT | 2.4 | 2.9 | 2.6 |
| Average | — | — | — | — | 3.2 | 2.9 | 2.6 |

Examples C9, 39-43

Control example C9, containing no antiseptic and examples of antimicrobial compositions of 120 grams each were prepared using the components shown in Table 9. Water, glycerin and LUROL ASY were added to a glass container and heated in an oven to approximately 70° C. Examples 39 and 42-43 were pH adjusted with sodium hydroxide to approximately 4.5. All the remaining components were added to a second glass container, which was swirled by hand and heated in an oven to approximately 110° C. The contents of the first container were then added to the second container and then mixed using a high shear rotor/stator Silverson homogenizer on high speed for approximately 1-2 minutes. Each composition was placed in a steam bath and mixed at low speed using a Gast overhead air mixer with radial flow impeller. For Examples 39-43, CHG was then added, followed by high-speed shear mixing for approximately 1-2 minutes, again using the Silverson homogenizer. Mixing continued until the composition was less than 40° C., using the Gast overhead air mixer.

These examples are water in oil emulsions. Examples 41-43, which incorporated an anionic phosphate surfactant (LUROL ASY), all achieved at least 3 log kill against one of the test organisms. Examples 42 and 43 further incorporated lactic acid and achieved greater than 6 log kill against *Staphylococcus epidermidis*.

Examples 44-49

Antimicrobial compositions of 250 grams were prepared using the components shown in Table 10. A mixture of POLAWAX, mineral oil, INCROQUAT BEHENYL TMS and CENTROFLEX F were added to a first container and heated to 70° C. in an oven. Water was heated in to 70° C. in a separate container. The water was added to the first container and finally CHG or COSMOCIL CQ was also added. Each composition was mixed using a high shear rotor/stator Silverson homogenizer on high speed for 1 minute.

These examples are oil in water emulsions comprising CHG or PHMB as antiseptics. Example 44 which did not incorporate lecithin achieved 6.7 and 7 log kill against MRSA and *E. coli* at 2.5 min. Example 45 (2% total CHG) incorporated lecithin. The lecithin partially inactivated the CHG decreasing the efficacy against both MRSA and *E. coli* significantly. Example 47 (only 0.1% total CHG), despite the low level of CHG was able to kill 2.5 log *E. coli* after a 10 min exposure. Example 48 was very similar to Example 47 except that it contained lecithin. The CHG was clearly neutralized by the lecithin as indicated by essentially no antimicrobial efficacy and further due to the observation of heavy bacterial growth in the sample after standing. The sample was not intentionally inoculated. Example 49 had an elevated level of CHG (0.5% total CHG) but due to the presence of lecithin still had less than 0.5 log kill against the test organisms.

TABLE 9

| Components | C9 | 39 | 40 | 41 | 42 | 43 |
|---|---|---|---|---|---|---|
| | \multicolumn{6}{c}{Example Numbers} |
| | \multicolumn{6}{c}{w/w % amount of components} |
| CHG 18.5% | — | 10.64 | 10.64 | 10.64 | 15.93 | 15.92 |
| CRODAMOL GTCC | — | — | — | — | 34.93 | 34.92 |
| Emulsifying polymer GG | 14.00 | 14.00 | 14.00 | 14.00 | — | — |
| Polymer QQ | — | — | — | — | 13.97 | 13.97 |
| Glycerin | — | — | 20.00 | 20.00 | — | — |
| AC540 | 1.50 | 1.50 | 1.50 | 1.50 | 1.50 | 1.50 |
| ARLAMOL E | — | — | 3.00 | 3.00 | 2.99 | 2.99 |
| DERMOL DIPS | 35.00 | 35.00 | 35.00 | 35.00 | — | — |
| LUROL ASY | — | — | — | 2.00 | 2.00 | 2.00 |
| HIPURE 88 | — | 1.00 | — | — | — | — |
| Lactic acid 10% in water | — | — | — | — | 0.21 | 0.24 |
| PLURONIC P-65 | — | — | — | — | 1.00 | 1.00 |
| Water | 49.50 | 37.86 | 15.86 | 13.86 | 27.48 | 27.48 |
| Total | 100.0 | 100.0 | 100.0 | 100.0 | 100.0 | 100.0 |
| | \multicolumn{6}{c}{Antimicrobial efficacy results:} |
| 2.5 min MRSA test 1 | 0.0 | 0.0 | 0.6 | 1.3 | NT | NT |
| 2.5 min MRSA test 2 | −0.2 | −0.1 | 0.6 | 1.1 | NT | NT |
| Average | −0.1 | 0.0 | 0.6 | 1.2 | — | — |
| 10 min MRSA test 1 | 0.3 | 1.7 | 0.8 | 1.7 | NT | NT |
| 10 min MRSA test 2 | 0.3 | 2.1 | 0.8 | 1.6 | NT | NT |
| Average | 0.3 | 1.9 | 0.8 | 1.7 | — | — |
| 10 min *E coli* test 1 | 0.2 | 0.2 | 1.6 | 2.4 | NT | NT |
| 10 min *E coli* test 2 | 0.7 | 0.3 | 1.6 | 3.9 | NT | NT |
| Average | 0.4 | 0.2 | 1.6 | 3.2 | — | — |
| 10 min *Staph Epi* test 1 | NT | NT | NT | NT | 5.5 | 6.8* |
| 10 min *Staph Epi* test 2 | NT | NT | NT | NT | 6.8 | 6.8* |
| Average | — | — | — | — | 6.2 | 6.8* |

*E coli* testing at 2.5 minutes was not performed.
*Complete Kill

TABLE 10

| Components | 44 | 45 | 46 | 47 | 48 | 49 |
|---|---|---|---|---|---|---|
| | \multicolumn{6}{c}{w/w % amount of components} | | | | | |
| PHMB (COSMOCIL CQ 20%) | — | — | 10.00 | — | — | — |
| CHG 18.5% | 11.11 | 11.11 | — | 0.53 | 0.50 | 2.50 |
| POLAWAX | 10.00 | 10.00 | 10.00 | 10.00 | 10.00 | 10.00 |
| INCROQUAT BEHENYL TMS | 3.00 | 3.00 | 3.00 | 3.00 | 3.00 | 3.00 |
| Mineral oil | 5.00 | 5.00 | 5.00 | 5.00 | 5.00 | 5.00 |
| CENTROFLEX F | — | 4.00 | — | — | 4.00 | 4.00 |
| Water | 70.89 | 66.89 | 72.00 | 81.47 | 77.50 | 75.50 |
| Total | 100.0 | 100.0 | 100.0 | 100.00 | 100.0 | 100.0 |
| \multicolumn{7}{c}{Antimicrobial efficacy results:} | | | | | | |
| 2.5 min MRSA test 1 | 6.7* | 4.1 | 5.6, 4.2 | 0.8 | 0.8 | 0.5 |
| 2.5 min MRSA test 2 | 6.7* | 4.3 | 6.6, 5.3 | 0.8 | 0.3 | 0.1 |
| Average | 6.7* | 4.2 | 5.4 | 0.8 | 0.5 | 0.3 |
| 2.5 min *E coli* test 1 | 7.0* | 3.0 | 5.2 | NT | NT | 0.4 |
| 2.5 min *E coli* test 2 | 7.0* | 2.9 | 5.8 | NT | NT | 0.4 |
| Average | 7.0* | 2.9 | 5.5 | — | — | 0.4 |
| 10 min MRSA test 1 | NT | NT | 6.8 | 1.3 | NT | NT |
| 10 min MRSA test 2 | NT | NT | 5.2 | 1.4 | NT | NT |
| Average | — | — | 6.0 | 1.4 | — | — |
| 10 min *E coli* test 1 | NT | NT | NT | 2.5 | NT | 0.4 |
| 10 min *E coli* test 2 | NT | NT | NT | 2.5 | NT | 0.2 |
| Average | — | — | — | 2.5 | — | 0.3 |

*Complete kill.

Examples C10, 50

Control Example C10 and antimicrobial composition Example 50 were prepared in quantities of 250 grams, using the components shown in Table 11. Benzethonium chloride (Example 50, only) was combined with CERAPHYL 494 in a container and heated in an oven to approximately 80° C. PLURONIC P-65 and AC 540 were added to the container, which was briefly swirled by hand and then further heated in an oven to approximately 110° C. The composition was removed from the oven, swirled by hand and allowed to cool without stirring.

Example 50 used CERAPHYL1 494 as the hydrophobic vehicle and achieved complete kill against MRSA at 2.5 and 10 min and 4.4 log kill against *E. coli* after 10 min. exposure.

TABLE 11

| Components | C10 | 50 |
|---|---|---|
| | w/w % amount of components | |
| Benzethonium Chloride | — | 4.00 |
| AC540 | 6.00 | 6.00 |
| PLURONIC P-65 | 2.00 | 2.00 |
| CERAPHYL 494 | 92.00 | 88.00 |
| Total | 100.0 | 100.0 |
| Antimicrobial efficacy results: | | |
| 2.5 min MRSA test 1 | −0.1 | 6.4* |
| 2.5 min MRSA test 2 | −0.1 | 6.4* |
| Average | −0.1 | 6.4* |
| 10 min MRSA test 1 | −0.1 | 6.4* |
| 10 min MRSA test 2 | 0.1 | 6.4* |
| Average | 0.0 | 6.4* |
| 10 min *E coli* test 1 | 0.7 | 1.9 |
| 10 min *E coli* test 2 | 0.5 | 6.9 |
| Average | 0.6 | 4.4 |

*E coli* testing at 2.5 minutes was not performed.
*Complete Kill

Examples 51-52

Antimicrobial compositions of 100 grams were prepared using the components shown in table 12. Povidone-iodine USP was added to glycerin in a glass container and heated to 70° C. in an oven briefly until it was dissolved. CARBOWAX 400 and CARBOWAX 1450 were added to the beaker, swirled by hand to mix and reheated to 70° C. in the oven to melt the PEG 1450. The composition was removed from the oven allowed to cool to approximately 40° C., while mixing on rollers, then transferred into jars and sealed.

TABLE 12

| Component | 51 | 52 |
|---|---|---|
| | w/w % amount of components | |
| CHG 18.5% | — | — |
| Povidone-Iodine USP (PVPI) | 5.0 | 5.0 |
| HIPURE 90% | — | 1.0 |
| CARBOWAX 400 | 58.65 | — |
| CARBOWAX 1450 | 15.90 | — |
| Glycerin | 20.45 | — |
| Dipropylene Glycol | — | 90.0 |
| PVP K90 | — | 4.0 |
| Total | 100.0 | 100.0 |
| Antimicrobial efficacy results on Porcine Urethra: | | |
| *E coli* Log red. After 30 min #1 | 1.8 | 2.3 |
| *E coli* Log red. After 30 min #2 | 1.7 | 1.6 |
| Average test results Log red. | 1.7 | 1.9 |
| Inoculum | 5.95 | 5.95 |

Example 53

An antimicrobial composition of 91 grams was prepared using the components shown in Table 13. LAURICIDIN, white petrolatum, FINSOLV TN, AEROSOL OT, and propylene glycol monocaprate were combined and heated in a glass vessel on a hot plate to 80° C., while continuing to mix by stirring until all components were dissolved and the mixture was clear. The mixture was cooled to approximately 55° C. and the remaining components: glycerin, triclosan, methyl paraben and water were added individually. The composition was stirred continuously while being allowed to cool to form a thick lubricous ointment.

Example 54

An antimicrobial composition of approximately 100 grams was prepared using the components shown in Table 13. All the components were combined and heated to approximately 80° C. The formulation was cooled while stirring to form an oinment, which was poured, into a glass jar. Upon further cooling, the oinment became more viscous.

Example 55

An antimicrobial composition of approximately 49 grams was prepared using the components shown in Table 13. All the components were combined and heated to approximately 60° C. to form a clear solution. The formulation was cooled to about 40° C., while stirring and poured into a glass jar. Upon further cooling, the oinment solidified to form a white hydrophilic ointment.

TABLE 13

| Component | Example Numbers | | |
|---|---|---|---|
| | 53 | 54 | 55 |
| | w/w % amount of components | | |
| IRGASAN (triclosan) | 1.61 | 1.06 | 0.95 |
| LAURICIDIN | 5.50 | 9.98 | 1.58 |
| 2-phenoxyethanol | — | — | 1.09 |
| CARBOWAX (PEG) 400 | — | — | 51.95 |
| CARBOWAX (PEG) 3350 | — | — | 31.93 |
| Glycerin USP | 19.96 | — | — |
| FINSOLV TN, C12-C15 Alkyl benzoate | 4.36 | — | — |
| Methyl paraben | 0.14 | — | — |
| Cetyl palmitate | — | 0.79 | — |
| Squalane | — | 0.70 | — |
| Behenyl alcohol | — | 1.64 | — |
| LUTROL F68 NF | — | — | 2.99 |

TABLE 13-continued

| Component | Example Numbers | | |
|---|---|---|---|
| | 53 | 54 | 55 |
| | w/w % amount of components | | |
| LUTROL L44 NF | — | — | 5.09 |
| Propylene glycol monocaprylate | 3.48 | 9.91 | 4.06 |
| Propylene glycol USP | — | 2.60 | — |
| SNOW WHITE Petrolatum | 55.54 | 72.61 | — |
| AEROSOL OT-75 (DOSS) | 1.09 | 0.72 | 0.38 |
| Water | 8.32 | — | — |
| Total | 100.0 | 100.0 | 100.0 |
| Antimicrobial efficacy results on Porcine Urethra: | | | |
| *E coli* Log red. After 30 min #1 | 5.81* | 5.81* | 5.81* |
| *E coli* Log red. After 30 min #2 | 5.81* | 5.81* | 5.81* |
| Average test results Log red. | 5.81 | 5.81 | 5.81 |
| Inoculum | 5.81 | 5.81 | 5.81 |

*Complete kill.

Examples 56-59, 62-66

Aqueous Examples 56-59, and 62-66 were prepared in 100-gram quantities using the components listed in Tables 14 and 15. Water and any surfactants (COMPLEMIX DOSS and/or PLURONIC F68) were mixed together, followed by the addition of any hydrophillic components (glycerin and dipropylene glycol), if present. To this mixture was added a polymeric thickener (KLUCEL M CS, CARBOWAX, SALCARE SC95, CARBOPOL 941 NF, or ARISTOFLEX AVC). Once the polymeric thickener was dissolved, an enhancer (lactic acid or EDTA) was added, followed by the antiseptic component (LAURICIDIN, chlorhexidine, povidone-iodine, hydrogen peroxide or triclosan) and the composition was mixed well.

Examples 60 and 61

Aqueous Examples 60 and 61 were prepared in 100 gram quantities using the components from Table 14. In both Examples the triclosan was predissolved in dipropylene glycol and heated to 75° C. All other components were combined in a separate container, neutralized to approximately pH 7 with sodium hydroxide, and heated to 75° C. The two mixtures were then combined, mixed well and allowed to cool to room temperature.

TABLE 14

| Component | Example Numbers | | | | | |
|---|---|---|---|---|---|---|
| | 56 | 57 | 58 | 59 | 60 | 61 |
| | w/w % amount of components | | | | | |
| Lauracidin | — | — | — | 4.5 | — | — |
| Povidone-Iodine USP | 5.0 | 5.0 | 5.0 | — | — | — |
| IRGASAN (triclosan) | — | — | — | — | 0.5 | 1.0 |
| Lactic Acid 90% | 1.0 | 1.0 | 1.0 | — | 1.0 | 1.0 |
| EDTA | — | — | — | 0.25 | — | — |
| Glycerin | — | — | — | 20.0 | — | — |
| Dipropylene Glycol LO+ | — | — | — | — | 10.0 | 10.0 |
| KLUCEL M CS | — | 3.0 | — | 3.0 | — | — |
| CARBOWAX WSR N 3000 | 2.0 | — | — | — | — | — |
| SALCARE SC95 | — | — | 3.0 | — | — | — |
| CARBOPOL 941NF | — | — | — | — | 1.5 | 1.5 |
| Complemix DOSS | 0.5 | 0.5 | 0.5 | 0.5 | 0.5 | 0.5 |
| PLURONIC F-68 (POLOXAMER 188) | — | — | — | 6.0 | 2.0 | 2.0 |
| Water | 91.5 | 90.5 | 90.5 | 65.75 | 84.50 | 84.00 |
| Total | 100.0 | 100.0 | 100.0 | 100.0 | 100.0 | 100.0 |

TABLE 14-continued

| | Example Numbers | | | | | |
|---|---|---|---|---|---|---|
| | 56 | 57 | 58 | 59 | 60 | 61 |
| Component | w/w % amount of components | | | | | |
| Antimicrobial efficacy results on Porcine Urethra: | | | | | | |
| E coli Log red. After 30 min #1 | 2.48 | 1.23 | 1.24 | 0.78 | 5.95* | 5.95* |
| E coli Log red. After 30 min #2 | 1.14 | 1.30 | 2.41 | 1.12 | 5.95* | 5.95* |
| Average test results Log red. | 1.81 | 1.27 | 1.83 | 0.95 | 5.95 | 5.95 |
| Inoculum | 5.95 | 5.95 | 5.95 | 5.95 | 5.95 | 5.95 |

*Complete Kill.

TABLE 15

| | Example Numbers | | | | |
|---|---|---|---|---|---|
| | 62 | 63 | 64 | 65 | 66 |
| Component | w/w % amount of components | | | | |
| CHG 18.5% | — | 2.0 | — | 2.0 | 2.0 |
| Hydrogen Peroxide 30% | — | — | 10.0 | — | — |
| IRGASAN DP300 (triclosan) | 2.0 | — | — | — | — |
| HIPURE 90% | 1.0 | 0.25 | 1.0 | 0.25 | — |
| KLUCEL M CS (HPMC) | — | 3.0 | 3.0 | 3.0 | 3.0 |
| ARISTOFLEX AVC | 1.0 | — | — | — | — |
| COMPLEMIX DOSS | 0.5 | — | — | — | — |
| PLURONIC F-68 | 2.0 | 2.0 | 2.0 | — | — |
| Water | 93.50 | 92.75 | 84.00 | 94.75 | 95.00 |
| Total | 100.0 | 100.0 | 100.0 | 100.0 | 100.0 |
| Antimicrobial efficacy results on Porcine Urethra | | | | | |
| E coli Log red. After 30 min #1 | 5.95* | 1.33 | 1.76 | 1.07 | 1.21 |
| E coli Log red. After 30 min #2 | 5.95* | 2.24 | 2.55 | 1.05 | 1.38 |
| Average test results Log red. | 5.95 | 1.79 | 1.16 | 1.06 | 1.30 |
| Inoculum | 5.95 | 5.95 | 5.95 | 5.95 | 5.95 |

*Complete Kill.

Examples 67-68

Antimicrobial compositions were prepared using the components shown in Table 16, with test results shown in Table 17. White petrolatum was heated in a beaker to at least approximately 82° C. In another beaker, glycerin and DOSS were heated until the DOSS was dissolved and this solution was allowed to cool to approximately 82° C. Next, the contents of the first beaker were mixed with the contents of the second beaker with a mixing propeller. Mixing was continued until the mixture cooled to 71° C. at which point the GML was added and mixing continued as the mixture continued to cool. When the mixture had cooled to about 54° C., the lactic acid was added and mixing continued until the composition was about to congeal. Just before the composition congealed at approximately 43° C., the composition was removed from the mixer and poured into ointment jars.

TABLE 16

| | w/w % amount of components | | | | |
|---|---|---|---|---|---|
| Example No. | GML | Lactic Acid (88) | DOSS (100%) | Glycerin | SNOW WHITE |
| 67 | 3.02 | 1.11 | 0.97 | 9.82 | 85.08 |
| 68 | 3.01 | 1.13 | 0.00 | 10.00 | 85.86 |

TABLE 17

| | MRSA (log reduction) | | | E. coli (log reduction) | | |
|---|---|---|---|---|---|---|
| Example No. | After 2 minutes | After 5 minutes | After 10 minutes | After 2 minutes | After 5 minutes | After 10 minutes |
| 67 | 3.02 | 3.84 | 6.47 | 3.59 | 5.25 | 5.29 |
| 68 | <3.02 | 3.02 | 3.14 | 2.88 | 3.54 | 3.16 |

The results for Examples 67 and 68 indicate that the full formulation of Example 67 had good kill against both MRSA (Gram positive) and E. coli (Gram negative) organisms. The log reduction was in excess of 3.5 logs after 5 minutes and 5 logs after 10 minutes. Elimination of the surfactant from the formulation (Example 68) resulted in a significant reduction in antimicrobial efficacy.

Examples 69-73

Antimicrobial compositions were prepared as described in Examples 67-68 using the components shown in Table 18, with test results shown in Tables 19 and 20. Mandelic acid was ground into a fine powder using a mortar and pestle and added to the glycerin and DOSS and heated to about 88° C. for Examples 69 and 70 or added directly to the hot, molten petrolatum at about 82° C. for Examples 71 and 72.

TABLE 18

| | w/w % amount of components | | | | |
|---|---|---|---|---|---|
| Example No. | GML | Mandelic Acid | DOSS (100%) | Glycerin | SNOW WHITE |
| 69 | 3.00 | 1.00 | 1.00 | 10.00 | 85.00 |
| 70 | 3.03 | 0.92 | 0.00 | 10.11 | 85.94 |
| 71 | 3.00 | 1.00 | 1.00 | 0.00 | 95.00 |
| 72 | 3.00 | 1.00 | 0.00 | 0.00 | 96.00 |
| 73 | 2.97 | 0.90 | 0.00 | 0.96 | 95.17 |

TABLE 19

| | MRSA (log reduction) | | | E. coli (log reduction) | | |
|---|---|---|---|---|---|---|
| Example No. | After 2 minutes | After 5 minutes | After 10 minutes | After 2 minutes | After 5 minutes | After 10 minutes |
| 69 | 3.6 | 5.7 | 5.9 | 4.0 | 5.6 | 6.1 |
| 70 | 2.8 | 3.9 | 4.3 | 5.7 | 5.6 | 6.0 |
| 71 | 5.0 | 5.8 | 5.4 | 5.4 | 5.8 | 6.3 |
| 72 | 2.4 | 2.6 | 3.6 | 3.2 | 3.3 | 3.7 |
| 73 | 2.3 | 3.1 | 4.1 | 4.0 | 3.9 | 4.7 |

TABLE 20

| Example No. | Pseudomonas ae. (log reduction) | | |
|---|---|---|---|
| | After 2 minutes | After 5 minutes | After 10 minutes |
| 69 | 4.4 | 6.4 | 6.5 |
| 70 | 3.3 | 4.2 | 5.1 |
| 71 | 4.0 | 4.6 | 5.7 |
| 72 | 2.9 | 2.9 | 3.2 |
| 73 | 2.9 | 3.6 | 3.9 |

Example 69 contained a hydrophilic component (glycerin) and surfactant (DOSS) in addition to the antimicrobial lipid (GML) and enhancer (mandelic acid). This sample had the best antimicrobial activity overall, achieving greater than 5.9 log reduction against all three organisms at 10 minutes. Example 70 contained no surfactant (no DOSS), which led to a decrease in activity over Example 69. Example 71 which contained no hydrophilic component had decreased activity over Example 69 but the effect was not as great as elimination of the surfactant. Example 72 containing no hydrophilic component or surfactant showed relatively poor antimicrobial activity. Addition of only 1% hydrophilic component (Example 73) showed an improvement in antimicrobial activity.

Example 74

An antimicrobial composition was prepared using the components listed in Table 21, with test results shown in Tables 22 and 23. GML, isopropyl isosterate, beeswax and FINSOLV TN were combined in a beaker, heated and stirred with a propeller mixer until a clear solution was obtained. Stirring was continued while cooling the solution to about 48° C. when the lactic acid was added. Stirring and cooling continued until the temperature was 43° C. when the composition was removed from the mixer and poured into the ointment jar.

TABLE 21

| | w/w % amount of components | | | | |
|---|---|---|---|---|---|
| Example No. | GML | Lactic acid (88%) | White Beeswax | Isopropyl isosterate | FINSOLV TN |
| 74 | 10.00 | 1.00 | 20.00 | 29.00 | 40.00 |

TABLE 22

| | MRSA (log reduction) | | | E. coli (log reduction) | | |
|---|---|---|---|---|---|---|
| Example No. | After 2 minutes | After 5 minutes | After 10 minutes | After 2 minutes | After 5 minutes | After 10 minutes |
| 74 | >6.3 | >6.3 | >6.3 | 7.3 | 7.3 | 7.3 |

TABLE 23

| | Pseudomonas ae. (log reduction) | | |
|---|---|---|---|
| Example No. | After 2 minutes | After 5 minutes | After 10 minutes |
| 74 | 8.0 | 8.0 | 8.0 |

The results indicated that the antimicrobial lipid plus enhancer in a non-petrolatum-based ointment had an exceptional kill rate of MRSA, E. coli, and Pseudomonas ae.

Examples 75-82

Antimicrobial Compositions were prepared as described in Examples 67-68 using the components shown in Table 24, with test results shown in Table 25. The surfactants were added like DOSS in Example 67.

TABLE 24

| | w/w % amount of components | | | | | | |
|---|---|---|---|---|---|---|---|
| Example No. | GML | Lactic acid | Glycerin | Surfactant | | Component | |
| | | | | Type | Amt. | Type | Amt. |
| 75 | 3.00 | 1.00 | 10.00 | CRODAFOS SG | 2.00 | Pet | 84.00 |
| 76 | 3.00 | 1.00 | 10.00 | DOSS (100%) | 2.00 | Pet | 84.00 |
| 77 | 3.00 | 1.00 | 10.00 | POLYSTEP B12 | 2.00 | Pet | 84.00 |
| 78 | 3.00 | 1.00 | 10.00 | MACKAM 50-SB | 2.00 | Pet | 84.00 |
| 79 | 3.00 | 1.00 | 10.00 | HOSTAPUR SAS 93G | 2.00 | Pet | 84.00 |
| 80 | 3.00 | 1.00 | 10.00 | LMDO | 2.00 | Pet | 84.00 |
| 81 | 3.00 | 1.00 | 10.00 | DOSS (100%) | 2.00 | PEG 400 | 84.00 |
| 82 | 3.00 | 1.00 | 10.00 | HOSTAPUR SAS 60 | 2.00 | Pet | 84.00 |

TABLE 25

| | MRSA (log reduction) | | | E. coli (log reduction) | | |
|---|---|---|---|---|---|---|
| Example No. | After 2 minutes | After 5 minutes | After 10 minutes | After 2 minutes | After 5 minutes | After 10 minutes |
| 75 | 6.41 | 6.17 | 6.41 | 5.29 | 5.56 | 2.65 |
| 76 | 3.33 | 3.38 | 6.17 | 5.85 | 5.54 | 6.14 |
| 77 | 5.74 | 6.41 | 5.88 | 3.49 | 4.34 | 6.11 |
| 78 | 4.18 | 5.05 | 5.90 | 2.63 | 2.80 | 4.47 |
| 79 | 5.73 | 6.11 | 6.11 | 6.03 | 6.23 | 6.23 |
| 80 | 3.45 | 5.16 | 5.78 | 2.69 | 3.40 | 4.05 |
| 81 | 6.11 | 6.11 | 6.11 | 6.23 | 6.23 | 6.23 |
| 82 | 5.73 | 5.02 | 6.22 | 6.07 | 6.17 | 6.17 |

Examples 75, 79, 81, and 82 had exceptional kill rates (>5 logs) after only 2 minutes against both MRSA and E. coli. The surfactants in these examples were anionic (sulfate, sulfonate, and phosphate). Example 77 also had very a good kill rate; however, the ethoxylation on this surfactant may have contributed to the lower efficacy shown against E. coli at the 2-minute and 5-minute time intervals. Example 76 contained DOSS, which had an exceptional kill rate (>6 logs) against both MRSA and E. coli after 10 minutes of exposure. Examples 78 and 80 contained zwitterionic and amine oxide surfactants, respectively, and the kill rate, while still good, was not as good as that of the anionic surfactants.

Example 83

The preparation of the $C10H_{23}$ Glycerin Ether was a two step process. First isopropylidene glycerol was prepared by adding 100 grams (g) glycerol, 400 mL acetone, 0.65 g p-toluenesulfonic acid, and 50 g of 3 Å molecular sieves to a 1-liter NALGENE bottle with a cap. Rolling the bottle on a roller for 24 hours mixed the contents of the bottle. Next 0.95 g potassium carbonate ($K_2CO_3$) was added to the contents. The mixture was filtered, passed through an activated alumina column, concentrated on a rotary evaporator, and distilled using a water aspirator to pull a vacuum (boiling point (bp) approximately 100° C.). The final product was then used to prepare glycerol ether.

Second 1-liter round-bottomed flask was purged with nitrogen and 500 mL xylene, 42 g isopropylidene glycerol, and 53.5 g potassium hydroxide (KOH) were added to the flask. The reaction flask was fitted with an overhead stirrer and a Dean-Stark trap. The contents were heated at reflux for approximately 15 hrs with azeotropic removal of $H_2O$. While continuing to heat at reflux, 61.4 g decyl bromide in 100 mL xylene was added dropwise to the reaction. After the addition was completed, the reaction was heated an additional 24 hrs at reflux. The contents were cooled, transferred to a separatory funnel, washed with deionized water 5 times using 100 mL of water each time, dried over magnesium sulfate ($MgSO_4$), filtered and concentrated on a rotarevaporator. The final product was distilled at reduced pressure (boiling point (bp) was approximately 136° C. at 0.5 millimeter (mm) Hg).

An antimicrobial composition was prepared using the components in Table 26, with test results shown in Table 27. The white petrolatum was heated to approximately 93° C. and the DOSS and the glyceryl ether were added to it while stirring using a mixing propeller. The mixture was stirred while being held at 93° C. until a clear solution was formed. The mixture was allowed to start cooling with continuous stirring. When the mixture reached approximately 65° C. the glycerin was added and the cooling and stirring continued. When the mixture reached approximately 49° C. the lactic acid was added and cooling and stirring continued until the composition was about to congeal (approximately 38° C.) and then it was poured into an ointment jar.

TABLE 26

| | w/w % amount of components | | | | |
|---|---|---|---|---|---|
| Example No. | HIPURE 88 | $C_{10}H_{23}$ glycerin ether | 100% DOSS | Glycerin | SNOW WHITE |
| 83 | 1.13 | 1.46 | 1.02 | 10.07 | 88.94 |

TABLE 27

| | MRSA (log reduction) | | | E. coli (log reduction) | | |
|---|---|---|---|---|---|---|
| Example No. | After 2 minutes | After 5 minutes | After 10 minutes | After 2 minutes | After 5 minutes | After 10 minutes |
| 83 | 3.16 | 3.70 | 4.51 | 4.68 | 5.88 | 5.47 |

The results for Example 83 indicated that over 3 log reductions after 2 minutes of exposure and over 4.5 log reductions after 10 minutes of exposure occurred for both MRSA and E. coli using an antimicrobial glycerin ether in combination with a enhancer (alpha-hydroxy acid).

Example 84

An antimicrobial composition was prepared using the components in Table 28, as described for Examples 67 and 68 but propylene glycol monocaprate was substituted for GML. Antimicrobial Kill test results shown in Table 29.

TABLE 28

| | w/w % amount of components | | | | |
|---|---|---|---|---|---|
| Example No. | HIPURE 88 | Propylene glycol monocaprate | 100% DOSS | Glycerin | SNOW WHITE |
| 84 | 1.12 | 3.01 | 1.00 | 9.92 | 84.95 |

TABLE 29

| | MRSA (log reduction) | | | E. coli (log reduction) | | |
|---|---|---|---|---|---|---|
| Example No. | After 2 minutes | After 5 minutes | After 10 minutes | After 2 minutes | After 5 minutes | After 10 minutes |
| 84 | 6.54 | 6.54 | 6.54 | 5.64 | 5.88 | 5.88 |

The results for Example 84 indicated that the antimicrobial composition containing propylene glycol monocaprate and an enhancer (lactic acid, an alpha-hydroxy acid) achieved an exceptional kill rate against MRSA (over 6 log reduction in 2 minutes) as well as an exceptional kill rate against E. coli (over 5.5 log reduction in 2 minutes).

Viscosity Test Results

The viscosity test results of select antimicrobial compositions are shown in Table 30. These were tested at approximately 23° C. (72° F.) in accordance with the Viscosity Test method.

TABLE 30

| VISCOSITY RESULTS | |
|---|---|
| Example No. | Viscosity cP × 1000 |
| 4 | 68,000 |
| 5 | 101,000 |
| 6 | 131,400 |
| 12 | 1,090,000 |
| 14 | 19,560 |
| 15 | 32,400 |
| 45 | 108,400 |
| 46 | 120,800 |
| 52 | 23,810 |
| 56 | <500 |
| 57 | 104,100 |
| 59 | 5,125 |
| 60 | 150,300 |
| 61 | 53,000 |
| 62 | 11,050 |
| 63 | 15,430 |
| C1 | 60,000 |
| C2 | 70,000 |

Dispersibility Testing

The ability of the antimicrobial compositions to disperse easily into saline (0.9 wt % NaCl) was evaluated according to the Dispersibility Test for multiple Examples. The results are summarized in Table 31. The results indicated that samples in hydrophilic or aqueous vehicles disperse quite well generally having less than 31% sample remaining and most often completely dispersing. Examples with a viscous hydrophobic vehicle, such as petrolatum, showed lower dispersibility. In addition, several of the aqueous Examples thickened with hydroxypropylmethylcellulose (KLUCEL) showed low dispersibility.

Urethra Model Antimicrobial Testing

The ability of the antimicrobial compositions to kill E. coli adhered to the inner surface of porcine urethra sections was evaluated according to the Urethra Model Antimicrobial Test for multiple Examples. The results are summarized in Table 31.

TABLE 31

Urethra Model Antimicrobial Testing

| Example Number | log red. #1 | log red. #2 | Average log reduction | Starting inoculum level | Dispersibility Results Wt (g) + | Wt % ++ | Observations |
|---|---|---|---|---|---|---|---|
| 4 | 5.81 | 5.81 | 5.81 | 5.81 | 0.18 | −8 | opaque, completely dispersed |
| 5 | 5.81 | 5.81 | 5.81 | 5.81 | 0.31 | 5 | opaque, completely dispersed |
| 6 | 1.81 | 1.78 | 1.8 | 5.95 | — | — | NT |
| 10 | 5.81 | 5.81 | 5.81 | 5.81 | 1.27 | 101 | slightly opaque, large gelatinous mass |
| 11 | 5.81 | 5.81 | 5.81 | 5.81 | 1.14 | 88 | slightly opaque, large gelatinous mass |
| 14 | 5.81 | 5.81 | 5.81 | 5.81 | 0.34 | 8 | partially dispersed, small solids |
| 15 | 5.81 | 5.81 | 5.81 | 5.81 | 0.36 | 10 | completely dispersed, small solids |
| 23 | 5.93 | 5.93 | 5.93 | 5.93 | 0.28 | 2 | clear, completely dispersed |
| 26 | 5.81 | 5.81 | 5.81 | 5.81 | 0.31 | 5 | clear, completely dispersed |
| 27 | 1.73 | 0.98 | 1.36 | 5.95 | 0.25 | −1 | completely dispersed |
| 29 | 0.13 | 0.46 | 0.3 | 5.93 | 1.21 | 95 | clear, large gelatinous mass |
| 30 | 2.22 | 2.15 | 2.19 | 5.93 | 1.24 | 98 | clear, large gelatinous mass |
| 31 | 0.16 | −0.02 | 0.07 | 5.93 | 1.33 | 107 | clear, large gelatinous mass |
| 32 | 3.19 | 5.93 | 4.56 | 5.93 | 1.24 | 98 | clear, large gelatinous mass |
| 33 | 0.01 | 0.17 | 0.09 | 5.93 | 1.41 | 115 | clear, large gelatinous mass |
| 34 | 4.41 | 5.95 | 5.18 | 5.95 | 1.15 | 89 | slightly opaque, large gelatinous mass |
| 44 | 5.81 | 5.81 | 5.81 | 5.81 | 1.05 | 79 | completely dispersed, small solids |
| 45 | 0.42 | 0.01 | 0.22 | 5.81 | 0.57 | 31 | completely dispersed, small solids |
| 46 | 5.81 | 5.81 | 5.81 | 5.81 | 0.48 | 22 | partially dispersed, small solids |
| 51 | 1.76 | 1.69 | 1.73 | 5.95 | — | — | NT |
| 52 | 2.28 | 1.59 | 1.94 | 5.95 | 0.34 | 8 | completely dispersed |
| 53 | 5.81 | 5.81 | 5.81 | 5.81 | — | — | NT |
| 54 | 5.81 | 5.81 | 5.81 | 5.81 | — | — | NT |
| 55 | 5.81 | 5.81 | 5.81 | 5.81 | — | — | NT |
| 56 | 2.48 | 1.14 | 1.81 | 5.95 | 0.43 | 17 | completely dispersed |
| 57 | 1.23 | 1.3 | 1.27 | 5.95 | 0.7 | 44 | some small solids remained |
| 58 | 1.24 | 2.41 | 1.83 | 5.95 | 0.52 | 26 | dispersed |
| 59 | 0.78 | 1.12 | 0.95 | 5.95 | 0.63 | 37 | dispersed |
| 60 | 5.95 | 5.95 | 5.95 | 5.95 | 0.29 | −3 | completely dispersed |
| 61 | 5.95 | 5.95 | 5.95 | 5.95 | 0.23 | −3 | completely dispersed |
| 62 | 5.95 | 5.95 | 5.95 | 5.95 | 0.26 | 0 | dispersed |
| 63 | 1.33 | 2.24 | 1.79 | 5.95 | 1.31 | 105 | almost dissolved |
| 64 | 1.76 | 2.55 | 2.16 | 5.81 | 0.19 | −7 | completely dissolved |
| 65 | 1.07 | 1.05 | 1.06 | 5.95 | 1.29 | 103 | Undipersed solid remained |
| 65 | 1.21 | 1.38 | 1.3 | 5.95 | 1.47 | 121 | Undipersed solid remained |
| C5 | 0.46 | 0.38 | 0.42 | 5.95 | 0.2 | −6 | clear, completely dispersed |
| C6 | 0.88 | 1.29 | 1.08 | 5.81 | 0.24 | −2 | clear, completely dispersed |
| C7 | 1.05 | 1.15 | 1.1 | 5.81 | 1.24 | 98 | clear, large gelatinous mass |

TABLE 31-continued

Urethra Model Antimicrobial Testing

| Example Number | Average log red. #1 | log red. #2 | log reduction | Starting inoculum level | Dispersibility Results Wt (g) + | Wt % ++ | Observations |
|---|---|---|---|---|---|---|---|
| K-Y Jelly* | 0.17 | 0.18 | 0.17 | 5.95 | | | |
| Lidocaine 2%** | −0.03 | 0.14 | 0.06 | 5.93 | | | |

Dispersibility Results:
+ Weight remaining (grams)
++ Percent remaining %
*K-Y Brand Jelly distributed by Personal Products Co., Skillman, NJ was obtained from Target, Minneapolis MN. This product along with Target Brand Lubricating jelly (Target Corp.) were analyzed for the concentration of preservative. This was done by dissolving the samples in methanol/water (60/40) and analyzing by HPLC. Samples were run in duplicated. The results indicate that the KY brand jelly contained an average of 440 ppm (0.044%) chlorhexidine gluconate (CHG) and the Target brand jelly contained an average of 445 ppm CHG.
**URO-JET: Lidocaine hydrochloride Jelly USP, 2% manufactured by International Medication Systems Ltd., South El Monte, CA.

The results of the Urethra Model Antimicrobial Testing indicate that commercially available widely used catheter lubricants such as KY brand lubricating jelly have essentially no antimicrobial activity (less than 0.20 log reduction). This is due to the very low concentration (preservative level) of the CHG. Similarly the 2% lidocaine jelly, which has been used as an intraurethral lubricating anaesthetic has no antimicrobial activity (less than 0.10 log reduction). Placebo Example C5 containing no antiseptic had an average log reduction of less than 0.50 log. Several of the test antimicrobial compositions that used a viscous hydrophobic vehicle (petrolatum) did not show significant log reduction after 30 minutes of exposure to the composition. Addition of a hydrophilic component, such as glycerin, however, improves the efficacy considerably. This effect can be seen by comparing Examples 30-31 and 32-33. The compositions comprising a hydrophobic vehicle and triclosan as an antiseptic had very good antimicrobial activity showing complete kill (see Examples 11 and 10). Example 34 comprising CHG in a hydrophobic vehicle with a hydrophilic component and surfactant component also had very good antimicrobial activity (greater than 5 log kill). All of the antimicrobial compositions in aqueous and/or hydrophilic vehicles had greater than or equal to about 1 log kill after 30 minute exposure except Example 45. Example 45 showed poor antimicrobial activity due to incorporation of lecithin in the sample containing CHG. A similar composition without lecithin (Example 44) showed complete kill. Every triclosan containing Example showed complete kill (greater than 5 log kill).

Examples 85-86

Antimicrobial compositions were prepared using the percentages of components shown in Table 32. Surfactants (COMPLEMIX, BRIJ 700 and MACKAM SB-50) were mixed with water until dissolved. Then lactic acid and malic acid were then added and dissolved. KLUCEL M CS(HPMC M CS) was added slowly into the mixture while stirring with an overhead stirrer until a gel was formed. Remaining components were then added and mixed well.

Examples 87-89

Antimicrobial compositions were prepared using the percentages of components shown in Table 32. Triclosan was predissolved in dipropylene glycol (DGP LO+) with POLAWAX (if present) while heating to 70° C. Water, also heated to 70° C., was added, followed by COMPLEMIX and PLURONIC F68 (if present). Lactic acid was then added to Example 88. The solutions were allowed to cool while mixing on a roller. CARBOPOL 941 NF was added by sifting into Example 89, followed by 4.29 mL of 5N NaOH.

TABLE 32

| | Example Numbers | | | | |
|---|---|---|---|---|---|
| | 85 | 86 | 87 | 88 | 89 |
| Component | w/w % amount of components | | | | |
| PVPI | 5.00 | 5.00 | — | — | — |
| 2-phenoxyethanol | — | — | 0.50 | — | — |
| IRGASAN DP300 | — | — | 2.00 | 1.00 | 1.00 |
| HIPURE 90 | 5.00 | 5.00 | — | 1.00 | — |
| Malic acid | 2.00 | 2.00 | — | — | — |
| Glycerin | — | — | 20.00 | — | — |
| DPG LO+ | — | — | — | 20.00 | 20.00 |
| KLUCEL M CS | 3.00 | 3.00 | — | — | — |
| POLAWAX | — | — | 12.00 | 12.00 | — |
| CARBOPOL 941 NF | — | — | — | — | 1.50 |
| COMPLEMIX (DOSS) | 0.50 | — | 1.00 | 0.50 | 0.25 |
| BRIJ 700 | — | 0.75 | — | — | — |
| MACKAM SB-50 | — | 2.50 | — | — | — |
| PLURONIC F-68 | — | — | — | — | 2.00 |
| NaOH 5N | 0.91 | 0.91 | — | — | 4.29 mL |
| Water | 83.59 | 80.84 | 64.50 | 65.50 | 75.25 |
| Total | 100.0 | 100.0 | 100.0 | 100.0 | 100.0 |
| Antimicrobial efficacy results: Urethra kill at 5 minutes | | | | | |
| Ave. Log reduction E coli | 0.7 | 0.5 | 0.9 | 0.5 | 6.3* |

Example 89: amount of 5N NaOH is in units of mL
* Complete kill.

Examples 90-91

Antimicrobial compositions were prepared using the percentages of components shown in Table 33. Surfactant (PLURONIC P-65) was mixed with water until dissolved. Then glycerin was added and dissolved. KLUCEL M CS(HPMC M CS) was added slowly into the mixture while stirring with an overhead stirrer until a gel was formed. Remaining components were then added and mixed well.

Examples 92-95

Antimicrobial compositions were prepared using the percentages of components shown in Table 33. PLURONIC F-68 was dissolved in water. POLAWAX (if present) and were then added and dissolved. KLUCEL M CS(HPMC M CS) was added slowly into the mixture while stirring with an overhead stirrer until a gel was formed. Remaining components were then added and mixed well.

TABLE 33

| Components | Example Numbers | | | | | |
|---|---|---|---|---|---|---|
| | 90 | 91 | 92 | 93 | 94 | 95 |
| | w/w % amount of components | | | | | |
| CHG 18.8% | — | — | 10.64 | 5.32 | 10.64 | 5.32 |
| Benzalkonium Chloride | 2.50 | 1.50 | — | — | — | — |
| Glycerin | 10.00 | 10.00 | — | — | — | — |
| KLUCEL M CS | 3.00 | 3.00 | — | — | 3.00 | 3.00 |
| POLAWAX | — | — | 12.00 | 12.00 | — | — |
| PLURONIC P-65 | 2.00 | 2.00 | — | — | — | — |
| PLURONIC F-68 | — | — | 1.00 | 1.00 | 2.00 | 2.00 |
| Water | 82.50 | 83.50 | 76.36 | 81.68 | 84.36 | 89.68 |
| Total | 100.0 | 100.0 | 100.0 | 100.0 | 100.0 | 100.0 |
| Viscosity cps at 23° C. | 50460 | 51120 | — | — | — | — |
| Antimicrobial efficacy results: | | | | | | |
| Urethra kill at 2 minutes Ave. Log reduction** *E coli* (ATCC 53500) | 5.6 | 5.6 | — | — | — | — |
| Urethra kill at 5 minutes Ave. Log reduction *E coli* (ATCC 11229) | 6.3* | 6.3* | 6.3* | 6.3* | 6.3* | 6.3* |

*Complete kill.
**6.1 Log Innoculation

Example 96

An antimicrobial composition was prepared using the percentages of components shown in Table 34. Triclosan and 2-phenoxyethanol were predissolved in dipropylene glycol (DGP LO+) while heating to 70° C. Water, also heated to 70° C., was added, followed by COMPLEMIX and PLURONIC F-68. The mixture was allowed to cool while mixing on a roller. Finally, CARBOPOL 941 NF was added by sifting into the well mixed composition.

Examples 97-98

Antimicrobial compositions were prepared using the percentages of components shown in Table 34. PLURONIC F-68 was dissolved in water. Tartaric acid and glycerin was added and mixed. KLUCEL M CS was added slowly into the mixture while stirring with an overhead stirrer until a gel was formed. The remaining components were then added and mixed well.

Examples 99

Control C11, 100

Antimicrobial compositions and Control C11 were prepared using the percentages of components shown in Table 34. PLURONIC F-127 was dissolved in chilled (4° C.) water. The following components (if present) COMPLEMIX, BRIJ 700, MACKAM 50-SB, EDTA, malic acid, and lactic acid were then added and mixed well. The remaining components were then added and mixed well.

Example 101

An antimicrobial composition was prepared using the percentages of components shown in Table 34. Water and surfactant PLURONIC P-65 were mixed. Glycerin was then added and mixed. KLUCEL M CS was added slowly into the mixture while stirring with an overhead stirrer until a gel was formed. The remaining components were then added and mixed well.

TABLE 34

| Component | Example Numbers | | | | | | |
|---|---|---|---|---|---|---|---|
| | 96 | 97 | 98 | 99 | C11 | 100 | 101 |
| | w/w % amount of components | | | | | | |
| CAPMUL PG8 | — | 5.00 | — | — | — | — | — |
| CAPMUL PG12 | — | — | 5.00 | — | — | — | — |
| PVPI | — | — | — | — | — | 5.00 | — |
| IRGASAN DP300 | 0.30 | — | — | 0.30 | — | — | — |
| 2-phenoxyethanol | 0.5 | — | — | — | — | — | — |
| Benzethonium Chloride | — | — | — | — | — | — | 2.00 |
| HIPURE 90 | — | — | — | — | — | 5.00 | — |
| Tartaric acid | — | 0.50 | 0.50 | — | — | — | — |
| Malic acid | — | — | — | — | — | 2.00 | — |
| EDTA | — | — | — | 0.50 | 0.50 | — | — |
| Glycerin | — | 10.00 | 10.00 | — | — | — | 10.00 |
| DPG LO+ | 10.00 | — | — | — | — | — | — |
| KLUCEL M CS | — | 3.00 | 3.00 | — | — | — | 3.00 |
| CARBOPOL 941 | 1.5 | — | — | — | — | — | — |
| COMPLEMIX | 0.50 | — | — | 0.50 | 0.50 | — | — |
| BRIJ 700 | — | — | — | — | — | 0.75 | — |
| MACKAM 50-SB | — | — | — | — | — | 2.50 | — |
| PLURONIC F-127 | — | — | — | 18.00 | 18.00 | 18.00 | — |
| PLURONIC P-65 | — | — | — | — | — | — | 2.00 |
| PLURONIC F-68 | 2.00 | 2.00 | 2.00 | — | — | — | — |

TABLE 34-continued

| Component | Example Numbers | | | | | | |
|---|---|---|---|---|---|---|---|
| | 96 | 97 | 98 | 99 | C11 | 100 | 101 |
| | w/w % amount of components | | | | | | |
| NaOH 5N | — | — | — | — | — | 0.91 | — |
| Water | 85.20 | 79.50 | 79.50 | 80.70 | 81.00 | 65.84 | 83.00 |
| Total | 100.0 | 100.0 | 100.0 | 100.0 | 100.0 | 100.0 | 100.0 |
| Viscocity (cps) 23° C. | — | — | — | 96 | 70 | 150 | 49,200 |
| Appearance | — | — | — | liquid | liquid | liquid | viscous |
| Urethra kill 2 min. Ave. Log reduction* E coli (ATCC 53500) | 2.2 | 2.5 | 0.6 | 0.4 | 0.2 | 2.0 | 0.0 |
| Urethra kill 5 min. Ave. Log reduction E coli (ATCC 11229) | 0.3 | 6.3 | 0.3 | — | — | — | — |

*6.1 Log Innoculation

Examples 102-107

Antimicrobial compositions were prepared using the percentages of components shown in Table 35. PLURONIC F-127 was dissolved in chilled (4° C.) water. The following components (if present) BRIJ 700, MACKAM 50-SB, PLURONIC F-68 and EDTA were added and mixed. The remaining components were then added and mixed well.

Example 108

An antimicrobial composition was prepared using the percentages of components shown in Table 35. COMPLEMIX was dissolved in water. ARISTOFLEX was then dissolved in the solution with thorough mixing by rolling the container on a roller. Finally, hydrogen peroxide was added to the mixture.

TABLE 35

| Component | Example Numbers | | | | | | |
|---|---|---|---|---|---|---|---|
| | 102 | 103 | 104 | 105 | 106 | 107 | 108 |
| | w/w % amount of components | | | | | | |
| Benzethonium Chloride | 2.00 | — | — | — | 2.00 | — | — |
| CAPMUL PG8 | — | 5.00 | — | — | — | 5.00 | — |
| CAPMUL PG12 | — | — | 5.00 | — | — | — | — |
| PVPI | — | — | — | 5.00 | — | — | — |
| 2-phenoxyethanol | — | — | — | — | 1.00 | — | — |
| $H_2O_2$ (30.6%) | — | — | — | — | — | — | 13.33 |
| EDTA | — | 0.50 | 0.50 | — | — | 0.50 | — |
| Glycerin | 10.00 | 10.00 | 10.00 | — | 10.00 | 10.00 | — |
| ARISTOFLEX AVC | — | — | — | — | — | — | 1.5 |
| COMPLEMIX | — | — | — | — | — | — | 0.5 |
| BRIJ 700 | — | — | — | 0.75 | — | — | — |
| MACKAM 50-SB | — | — | — | 1.25 | — | — | — |
| PLURONIC F-127 | 18.00 | 18.00 | 18.00 | 18.00 | 18.00 | 18.00 | — |
| PLURONIC F-68 | — | 2.00 | 2.00 | — | — | 2.00 | — |
| Water | 70.00 | 64.50 | 64.50 | 75.00 | 69.00 | 64.5 | 84.67 |
| Total | 100.0 | 100.0 | 100.0 | 100.0 | 100.0 | 100.0 | 100.0 |
| Viscocity (cps) | 190 | >240k | >240k | 276 | — | — | >240k |
| Appearance | liquid | viscous foamy | Viscous | liquid | clear viscous | foamy gel | viscous foamy |
| Urine Elution (sec) 2.5 cm plug | — | — | — | — | 1.5 | >3 min | — |
| Urethra kill 2 min. Ave. Log reduction* E coli (ATCC 53500) | 2.8 | 1.5 | 1.6 | 2.2 | 1.6 | — | 0.5 |

*6.1 Log Innoculation

Examples 109-113

Antimicrobial compositions were prepared using the percentages of components shown in Table 36. Water and surfactants (COMPLEMIX, PLURONIC F-68, PLURONIC P-65, or TWEEN 20) were mixed together, followed by the addition of hydrophillic components (glycerin and dipropylene glycol), if present. KLUCEL M CS was added slowly into the mixture while stirring with an overhead stirrer until a gel was formed. The remaining components were then added and mixed well.

TABLE 36

| Components | 109 | 110 | C12 | 111 | 112 | 113 |
|---|---|---|---|---|---|---|
| | \multicolumn{6}{c}{w/w % amount of components} | | | | | |
| CAPMUL PG8 | — | — | — | — | — | 5.00 |
| CHG 18.8% | — | — | — | 10.64 | — | — |
| IRGASAN DP300 | — | — | — | — | 0.30 | — |
| 2-phenoxyethanol | — | — | — | 1.00 | 1.00 | — |
| Benzalkonium Chloride | 2.00 | 2.00 | — | — | — | — |
| EDTA | — | — | — | — | — | 0.50 |
| Glycerin | — | 10.00 | — | — | — | — |
| DPG LO+ | 10.00 | — | 10.00 | — | 10.00 | 10.00 |
| KLUCEL M CS | 3.00 | 3.00 | 3.00 | 3.00 | — | 3.00 |
| CARBOPOL 941 NF | — | — | — | — | 1.50 | — |
| COMPLEMIX | — | — | — | — | 0.50 | — |
| PLURONIC P-65 | 2.00 | 2.00 | 2.00 | — | — | — |
| PLURONIC F-68 | — | — | — | 1.00 | 2.00 | 2.00 |
| TWEEN 20 | — | — | — | 1.00 | — | — |
| Water | 83.00 | 83.00 | 85.00 | 83.36 | 84.70 | 79.50 |
| Total | 100.0 | 100.0 | 100.0 | 100.0 | 100.0 | 100.0 |
| Appearance | clear gel | Cloudy dispersion | clear gel | clear gel | clear gel | viscous foamy gel |
| Urine Elution (sec) 2.5 cm plug | 10.6 | 28.0 | 52.0 | 30.0 | 2.5 | 2.0 |
| Antimicrobial efficacy results: | | | | | | |
| Urethra kill at 2 minutes Ave. Log reduction* *E coli* (ATCC 53500) | 1.1 | 5.0 | −0.2 | 1.2 | 2.6 | −0.1 |

*6.1 Log Innoculation

Examples 114-119

Antimicrobial compositions were prepared using the percentages of components shown in Table 37. Water and any surfactants (COMPLEMIX, BRIJ 700, MACKAM 50-SB, or PLURONIC P-65) were mixed together, followed by the addition of glycerin (if present). KLUCEL M CS was added slowly into the mixture while stirring with an overhead stirrer until a gel was formed. The remaining components were then added and mixed well.

TABLE 37

| Components | 114 | 115 | 116 | 117 | 118 | 119 |
|---|---|---|---|---|---|---|
| | \multicolumn{6}{c}{w/w % amount of components} | | | | | |
| PVPI | — | 5.00 | 5.00 | 5.00 | 5.00 | — |
| IRGASAN DP300 | — | — | — | — | — | — |
| 2-phenoxyethanol | 1.00 | — | — | 1.00 | — | 1.00 |
| Benzethonium Chloride | — | — | — | — | — | 2.00 |
| HIPURE 90 | — | 5.00 | 5.00 | 5.00 | 3.00 | — |
| Tartaric acid | — | — | — | — | 1.00 | — |
| Malic acid | — | 2.00 | 2.00 | 2.00 | — | — |
| EDTA | 0.50 | — | — | — | — | — |
| Glycerin | — | — | — | — | — | 10.00 |
| KLUCEL M CS | 3.00 | 3.00 | 3.00 | 3.00 | 3.00 | 3.00 |
| COMPLEMIX | 0.50 | — | — | — | — | — |
| BRIJ 700 | — | 0.75 | 0.75 | 0.75 | 0.75 | — |
| MACKAM 50-SB | — | 2.50 | 2.50 | 2.50 | 2.50 | — |
| PLURONIC P-65 | — | — | — | — | — | 2.00 |

TABLE 37-continued

| | Example Numbers | | | | | |
|---|---|---|---|---|---|---|
| | 114 | 115 | 116 | 117 | 118 | 119 |
| Components | w/w % amount of components | | | | | |
| NaOH 5N | — | 0.60 | 0.30 | 0.30 | 0.30 | — |
| Water | 95.00 | 81.15 | 81.45 | 80.45 | 84.45 | 82.00 |
| Total | 100.0 | 100.0 | 100.0 | 100.0 | 100.0 | 100.0 |
| Appearance | — | Iodine gel | Iodine gel | Iodine gel | Iodine gel | Clear gel |
| Urine Elution (sec) 2.5 cm plug | 2.0 | 2.5 | 6.0 | 8.0 | 11.5 | 30.0 |
| Antimicrobial efficacy results: | | | | | | |
| Urethra kill at 2 min. Ave. Log reduction* E coli (ATCC 53500) | −0.0 | 1.3 | 3.2 | 2.9 | 1.3 | 3.3 |

*6.1 Log Innoculation

Examples 120-123

Antimicrobial compositions were prepared using the percentages of components shown in Table 38. Water and PLURONIC P-65 were mixed together, followed by the addition of dipropylene glycol. KLUCEL M CS was added slowly into the mixture while stirring with an overhead stirrer until a gel was formed. The remaining components were then added and mixed well.

TABLE 38

| | Example Numbers | | | | | |
|---|---|---|---|---|---|---|
| | 120 | 121 | 122 | 123 | KY Jelly | UROJET |
| Components | w/w % amount of components | | | | | |
| Benzalkonium Chloride | 2.00 | 2.00 | 2.00 | 2.00 | — | — |
| DPG LO+ | 10.00 | 10.00 | 10.00 | 10.00 | — | — |
| KLUCEL M CS | 3.00 | 2.75 | 2.50 | 3.25 | — | — |
| PLURONIC P-65 | 2.00 | 2.00 | 2.00 | 2.00 | — | — |
| Water | 83.00 | 83.25 | 83.50 | 82.75 | — | — |
| Total | 100.0 | 100.0 | 100.0 | 100.0 | 100.0 | 100.0 |
| Viscocity at 23° C. | — | — | — | 193,200 | — | — |
| Appearance | clear thick gel | clear thick gel | clear thick gel | clear thick gel | clear thick gel | clear thick gel |
| Urine Elution (sec) 2.5 cm plug | 23.7 | 17.4 | 11.3 | 45.1 | 37.5 | 1.4 |
| Antimicrobial efficacy results: | | | | | | |
| Urethra kill at 2 min. Ave. Log reduction* E coli (ATCC 53500) | 0.0 | — | — | — | — | — |

*6.1 Log Innoculation

Examples 124-127

Antimicrobial compositions were prepared using the percentages of components shown in Table 39. Water and PLURONIC P-65 were mixed together, followed by the addition of dipropylene glycol. KLUCEL M CS was added slowly into the mixture while stirring with an overhead stirrer until a gel was formed. The remaining components were then added and mixed well.

Control Examples C13-C16

Control compositions were prepared using the percentages of components shown in Table 39. PLURONIC F-127 was dissolved chilled (4° C.) water. PLURONIC F-68 (if present) was then dissolved into the chilled aqueous solution. Dipropylene glycol was added to the solution and mixed well.

TABLE 39

| | Example Numbers | | | | | | | |
|---|---|---|---|---|---|---|---|---|
| | 126 | 127 | 128 | 129 | C13 | C14 | C15 | C16 |
| Component | w/w % amount of components | | | | | | | |
| Benzalkonium Chloride | 2.00 | 2.00 | 2.00 | 2.00 | — | — | — | — |
| DPG LO+ | 10.00 | 10.00 | 10.00 | 10.00 | 10.00 | 10.00 | 10.00 | 10.00 |

TABLE 39-continued

|  | Example Numbers | | | | | | | |
|---|---|---|---|---|---|---|---|---|
| Component | 126 | 127 | 128 | 129 | C13 | C14 | C15 | C16 |
| | w/w % amount of components | | | | | | | |
| KLUCEL M Pharma | 3.00 | 2.75 | 2.50 | 3.25 | — | — | — | — |
| PLURONIC F-127 | — | — | — | — | 18.00 | 18.00 | 16.00 | 14.00 |
| PLURONIC P-65 | 2.00 | 2.00 | 2.00 | 2.00 | — | — | — | — |
| PLURONIC F-68 | — | — | — | — | — | 2.00 | — | — |
| Water | 83.00 | 83.25 | 83.50 | 82.75 | 70.00 | 72.00 | 74.00 | 76.00 |
| Total | 100.0 | 100.0 | 100.0 | 100.0 | 100.0 | 100.0 | 100.0 | 100.0 |
| Viscocity (cps) | 155,600 | 105,600 | 74,880 | >240K | >240K | >240K | >240K | >240K |
| Appearance | clear, viscous gel | clear, viscous gel | Liquid at 23° C., almost solid at 37° C. | liquid at 23° C., almost solid at 37° C. | liquid at 23° C., almost solid at 37° C. | liquid at 23° C., almost solid at 37° C. | liquid | liquid |
| Urine Elution (sec) 2.5 cm plug | 22.6 | 21.0 | 15.3 | 64.2 | <1 | 1.3 | 1.0 | — |
| Urine Elution (sec) 3.8 cm plug | 64.0 | 31.5 | 35.9 | 1.0 | 1.0 | — | — | — |
| Urine Elution (sec) 5.1 cm plug | 121.6 | 58.0 | 47.0 | 1.0 | 1.0 | — | — | — |
| Antimicrobial efficacy results: | | | | | | | | |
| Urethra kill 2 min. Ave. Log reduction* MRSA (ATCC 33593) | 3.6** | 3.6** | 3.6** | 3.6** | — | — | — | — |

*5.6 Log Innoculation.
**No bacteria were recovered. The kill was between 3.6 and 5.6 log.

Control Examples C17-C18

Control compositions were prepared using the percentages of components shown in Table 40. Polyvinylpyrrolidone K$_{90}$ was dispersed in water with rapid overhead stirring. Dipropylene glycol was then added to the dispersion, followed by PLURONIC P-65 and the compositions were mixed well.

Examples 128-131

Antimicrobial compositions were prepared using the percentages of components shown in Table 40. Water and PLURONIC P-65 were mixed together, followed by the addition of dipropylene glycol. KLUCEL M CS was added slowly into the mixture while stirring with an overhead stirrer until a gel was formed. The remaining components were then added and mixed well.

TABLE 40

|  | Example Numbers | | | | | |
|---|---|---|---|---|---|---|
| Components | C17 | C18 | 128 | 129 | 130 | 131 |
| | w/w % amount of components | | | | | |
| CPC | — | — | 2.00 | 1.00 | — | — |
| CTAB | — | — | — | — | 2.00 | 1.00 |
| DPG LO+ | 10.00 | 10.00 | 10.00 | 10.00 | 10.00 | 10.00 |
| KLUCEL M CS | — | — | 3.00 | 3.00 | 3.00 | 3.00 |
| PVP K90 | 2.00 | 2.50 | — | — | — | — |
| PLURONIC P-65 | 2.00 | 2.00 | 2.00 | 2.00 | 2.00 | 2.00 |
| Water | 86.00 | 85.5 | 83.00 | 84.00 | 83.00 | 84.00 |
| Total | 100.0 | 100.0 | 100.0 | 100.0 | 100.0 | 100.0 |
| Viscocity at 23° C. | — | — | 139,200 | 144,200 | 164,900 | 128,600 |
| Appearance | clear thick gel | clear thick gel | clear thick gel | clear thick gel | — | — |
| Urine Elution (sec) 2.5 cm plug | — | — | 30.5 | 36.3 | 45.5 | 33.8 |
| Antimicrobial efficacy results: | | | | | | |
| Urethra kill at 2 min. Ave. Log reduction* E coli (ATCC 53500) | — | — | 3.6** | 1.0 | −0.9 | −0.1 |

*5.6 Log Innoculation.
**No bacteria were recovered. The kill was between 3.6 and 5.6 log Lipid Ester Examples Examples 132-137 and C19

Antimicrobial compositions were prepared using the components shown in Table 41. For the formulation that contains IPA, the procedure was as follows. DOSS, PLURONIC P65 and lipid ester were added to IPA and mixed to dissolve forming a solution. Next, EDTA was added to water and the mixture stirred until EDTA dissolved. Then the ester containing IPA solution was added to the resulting water solution to form the test formulation. For formulations that do not contain IPA, the mixing procedure was the same as described in Example 1. All of the formulations in Table 3 contained 10% PLURONIC in addition to the components listed with water making up the remaining portion of the formulation.

TABLE 41

| Example No. | Lipid Ester | Ester purity by GC | Components (w/w %) | | | |
|---|---|---|---|---|---|---|
| | | | Ester | IPA | DOSS | EDTA |
| 132 | Lauryl Lactate (Ceraphyl 31) | 48% | 3.0 | 10.0 | 1.0 | 0.2 |
| 133 | Lauryl Lactate (Pelemol LL) | 75% | 3.0 | 10.0 | 1.0 | 0.2 |
| 134 | Lauryl Lactate (Pelemol LL) | 75% | 3.0 | — | — | — |
| 135 | 2-ethylhexyl lactate | Nd | 3.0 | 10 | 1.0 | 0.2 |
| 137 | 2-ethylhexyl lactate | Nd | 3.0 | — | — | — |
| C19 | None | Na | — | 10 | 1.0 | 0.2 |

Nd—not determined.
Na—not applicable

The compositions of Examples 134-138 were evaluated using the Antimicrobiol Kill Test and the results are shown in Tables 42a-42c.

TABLE 42a

Antimicrobial Kill Test Results

| Example Number | Log Reduction of S. aureus (ATCC 33593) Initial inoculum 7.95 log | | |
|---|---|---|---|
| | After 1 minute | After 3 minutes | After 5 minutes |
| 133 | 4.6 | 4.2 | 6.0 |
| 134 | <2.4* | <2.4* | <2.41* |
| 135 | 4.3 | 6.0 | 6.0 |
| 136 | <2.4* | <2.4* | 3.4 |
| C19 | <2.0* | <2.0* | <2.0* |

*High initial inoculums and lack of antimicrobial activity in the time length tested resulted in colony counts too numerous to count even on the highest dilution plate. This prevented an exact log reduction from being determined. Approximately 2 Log was the lower limit of detection.

TABLE 42b

Antimicrobial Kill Test Results

| Example Number | Log Reduction of E. coli (ATCC11229) Initial inoculum 7.59 log | | |
|---|---|---|---|
| | After 1 minute | After 3 minutes | After 5 minutes |
| 132 | <2.0* | <2.0* | <2.0* |
| 135 | 5.6 | 5.6 | 5.6 |
| C19 | <2.0* | <2.0* | <2.0* |

*See discussion after Table 42a concerning limits of exact log reduction determination.

TABLE 42c

Antimicrobial Kill Test Results

| Example Number | Log Reduction of E. coli (ATCC11229) Initial inoculum 5.81 log | | | |
|---|---|---|---|---|
| | After 1 minute | After 3 minutes | After 5 minutes | After 10 minutes |
| 133 | <0.3* | <0.3* | <0.3* | 0.4 |
| 134 | <0.3* | <0.3* | <0.3* | <0.3* |
| 136 | 1.5 | 3.6 | 3.4 | 3.8 |

*See discussion after Table 42a concerning limits of exact log reduction determination.

Subject Acceptability of Placebo on Human Nasal Mucosal Tissue—First Panel Evaluation A panel of 10 normal healthy volunteers of either gender over 18 years of age evaluated a component composition without active antiseptic to determine acceptability and to develop evaluation methodology for future evaluations.

The compositions evaluated are shown in Table 43.

TABLE 43

| Composition | Components (weight percent) | | | | | |
|---|---|---|---|---|---|---|
| | Lactic Acid USP | Glycerin USP | Docuate sodium USP (50%) | White petrolatum USP | PEG 400 NF | PEG 3350 NF |
| W | 1.00 | 10.00 | 2.00 | 87.00 | 0.00 | 0.00 |
| X | 1.00 | 20.00 | 2.00 | 0.00 | 59.00 | 18.00 |

Test Procedure

A dose was 0.5 mL of Composition W or X applied using a preloaded 1 mL plastic syringe. The volunteers applied the first dose to their nares after viewing a demonstration of the technique. The volunteers applied a second and third dose during Day 1.

One-half of the volunteers (5) were dosed with Composition W and one-half of the volunteers were dosed with Composition X on Day 1 and given a Rhinoscopic Examination of Nares before and after application on Day 1 and after 24 hours on Day 2. On Day 8 those volunteers dosed with Composition W on Day 1 received Composition X and those dosed with Composition X on Day 1 received Composition W. They were given a Rhinoscopic Examination of Nares before and after application on Day 8 and after 24 hours on Day 9.

Volunteers completed a questionnaire on Day 1 and on Day 9.

Results:

All 10 volunteers successfully completed both periods of the study. Descriptive analysis was provided for each categorical variable in the study.

Composition W was preferred by 10/10 of the volunteers. Five of ten volunteers could not complete all three application of Composition X. They cited stinging, burning and runny noses as primary reasons. Composition X caused more rhinorrhea than Composition W. Volunteers using Composition X felt they could use the ointment for a shorter period of time than with Composition W. Composition W could be felt to remain in the nasal vestibule longer (mean 218 minutes) than Composition X (mean 145 minutes). This may indicated that formulations based on water soluble hydrophilic vehicles, such as PEG, may be more irritating on other sensitive tissues such as the urethra.

Subject Acceptability of Placebo on Human Nasal Mucosal Tissue—Second Panel Evaluation A second panel evaluation was done to determine acceptability of essentially anhydrous ointments based hydrophobic vehicles containing lactic acid or mandelic acid. The criteria for the panel were the same as for the first panel. The compositions evaluated are given in Table 44.

TABLE 44

| | Components (weight percent) | | | | |
|---|---|---|---|---|---|
| Composition | Lactic Acid USP | Mandelic Acid | DOSS USP (50%) | Glycerin USP | White petrolatum USP |
| Y | 1.00 | 0.00 | 2.00 | 10.00 | 87.00 |
| Z (emulsion) | 0.00 | 1.00 | 2.00 | 10.00 | 87.00 |

The test procedure was the same as that used for the first panel except a cotton swab was used to apply the composition rather than a tube.

Results:

Both ointments were acceptable with minimal, if any, side effects. The preference for the two ointments was fairly equally divided. Four of ten volunteers expressed a slight preference for the mandelic acid composition, three of ten volunteers expressed a slight preference for the lactic acid composition, and three of ten volunteers noticed no difference between the compositions.

Each volunteer applied 0.5 mL of composition; however, approximately 0.1 gram was routinely left on the swab. Therefore the dose was about 0.2 mL per nares. The time that the ointments remained in the volunteers' noses varied between volunteers, but there were indications that the ointment remained in place up to 24 hours. Two volunteers reported that the ointment appeared to accumulate from application to application. The absence of discomfort in a sensitive tissue such as the anterior nares may indicate that similar compositions would be acceptable for intraurethral application or application to other sensitive tissue.

The feel of the ointment in the nose and smell were the most noticed characteristics of both ointments, but the characteristics were all in the acceptable range.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of delaying the onset of an infection caused by a microbial organism in an internal cavity of a subject, the method comprising: contacting at least a portion of the interior surface of an opening leading to the internal cavity with an antimicrobial composition; and subsequently at least partially inserting an instrument into the opening, wherein the antimicrobial composition comprises:
   an effective amount of an antimicrobial component comprising an antiseptic present in an amount of at least 0.1 weight percent based on the total weight of the composition; and
   a surfactant component distinct from the antimicrobial component, wherein the surfactant component is present in an amount of at least 0.1 wt-% based on the total weight of the composition, and the surfactant component comprises an anionic surfactant, zwitterionic surfactant, poloxamer surfactant, amine oxide surfactant, or combinations thereof;
   wherein the opening is a urethra, and the cavity is a bladder;
   wherein a surfactant incorporated into an iodophor is not considered the surfactant component, but is part of the antimicrobial component; and
   wherein the antimicrobial composition is placed on at least 1 cm deep of the interior surface of the opening leading to the internal cavity.

2. The method of claim 1 wherein the antimicrobial composition further comprises a vehicle comprising less than 1 wt-% water.

3. The method of claim 1 wherein the antimicrobial composition further comprises a second active agent distinct from the antimicrobial component.

4. The method of claim 1 wherein the antimicrobial composition further comprises:
   at least 0.20 wt-% of an enhancer component comprising an alpha-hydroxy acid, a beta-hydroxy acid, a chelating agent, a (C1-C4)alkyl carboxylic acid, a (C6-C12)aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof.

5. The method of claim 1 wherein the antimicrobial composition further comprises:
   a hydrophilic vehicle other than water.

6. A method of delaying the onset of an infection caused by a microbial organism in an internal cavity of a subject, the method comprising: contacting at least a portion of the interior surface of an opening leading to the internal cavity with an antimicrobial composition; and subsequently at least partially inserting an instrument into the opening, wherein the antimicrobial composition comprises:
   an effective amount of an antimicrobial component comprising an antiseptic present in an amount of at least 0.1 weight percent based on the total weight of the composition;
   a surfactant component distinct from the antimicrobial component and present in a total amount of at least 0.1 wt-% based on the total weight of the composition, and the surfactant component comprises an anionic surfactant, zwitterionic surfactant, poloxamer surfactant, amine oxide surfactant, or combinations thereof;
   wherein the composition has a viscosity of at least 1,000 cps at 23° C.;
   wherein the opening is a urethra, and the cavity is a bladder;
   wherein a surfactant incorporated into an iodophor is not considered the surfactant component, but is part of the antimicrobial component; and
   wherein the antimicrobial composition is placed on at least 1 cm deep of the interior surface of the opening leading to the internal cavity.

7. The method of claim 1 or claim 6 wherein the antiseptic comprises an antimicrobial lipid, a phenolic antiseptic, a cationic antiseptic, iodine and/or an iodophor, a peroxide antiseptic, an antimicrobial natural oil, or combinations thereof.

8. The method of claim 1 or claim 6 wherein the instrument is selected from the group consisting of urinary catheters and surgical instruments.

9. The method of claim 1 or claim 6 wherein residual antimicrobial efficacy is provided to the surface to which the antimicrobial composition is applied.

10. The method of claim 1 or claim 6 wherein the instrument is treated with the same or different antimicrobial composition prior to the inserting step.

11. The method of claim 1 or claim 6 wherein the pH of the composition is less than 7.

12. The method of claim 1 or claim 6 wherein the external tissue surrounding the opening is treated with the same or different antimicrobial composition prior to the inserting step.

13. The method of claim 7 wherein the antiseptic comprises a cationic antiseptic.

14. The method of claim 1, wherein the surfactant component comprises zwitterionic surfactant, amine oxide surfactant, or combinations thereof.

15. The method of claim 6, wherein the surfactant component comprises zwitterionic surfactant, amine oxide surfactant, or combinations thereof.

16. The method of claim 1, wherein the antimicrobial composition is a liquid.

17. The method of claim 1, wherein contacting at least a portion of the interior surface of an opening leading to the internal cavity comprises filling the urethral passage with the composition.

18. The method of claim 1, wherein contacting at least a portion of the interior surface of an opening leading to the internal cavity with the antimicrobial composition comprises placing the antimicrobial composition at least one centimeter deep into the urethra and in an amount that is at least 10 milligrams antimicrobial composition per square centimeter of urethral tissue.

19. The method of claim 1, wherein contacting at least a portion of the interior surface of an opening leading to the internal cavity with the antimicrobial composition comprises allowing the composition to reside on the internal surface for at least 10 seconds before at least partially inserting an instrument into the opening.

20. The method of claim 1, wherein contacting at least a portion of the interior surface of an opening leading to the internal cavity with the antimicrobial composition comprises allowing the composition to reside on the internal surface for at least 30 seconds before at least partially inserting an instrument into the opening.

21. The method of claim 1, wherein the instrument is not coated with the antimicrobial composition.

\* \* \* \* \*